United States Patent
Sosnowski et al.

(10) Patent No.: US 6,613,563 B1
(45) Date of Patent: Sep. 2, 2003

(54) VIRAL VECTORS WITH MODIFIED TROPISM

(75) Inventors: Barbara A. Sosnowski, Coronado, CA (US); Andrew Baird, San Diego, CA (US); Glenn F. Pierce, Rancho Santa Fe, CA (US); David T. Curiel, Birmingham, AL (US); Joanne T. Douglas, Huntsville, AL (US); Buck E. Rogers, Birmingham, AL (US)

(73) Assignees: Selective Genitcs, Inc., San Diego, CA (US); UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/039,060

(22) Filed: Mar. 13, 1998

Related U.S. Application Data

(60) Provisional application No. 60/040,782, filed on Mar. 14, 1997, and provisional application No. 60/065,265, filed on Nov. 10, 1997.

(51) Int. Cl.$^7$ .................. C12N 15/00; C07H 21/04; A61K 39/42; A61K 39/395; C07K 1/00
(52) U.S. Cl. ................. 435/320.1; 536/23.1; 536/23.5; 424/130.1; 424/147.1; 530/350
(58) Field of Search ................ 514/1, 2, 44; 435/320.1; 536/23.1, 23.5; 424/130.1, 147.1; 530/350

(56) References Cited

U.S. PATENT DOCUMENTS

| | | | | |
|---|---|---|---|---|
| 5,191,067 A | * | 3/1993 | Lappi et al. ................. | 530/399 |
| 5,332,671 A | | 7/1994 | Ferrara et al. ........... | 435/240.1 |
| 5,612,318 A | * | 3/1997 | Weichselbaum et al. ...... | 514/44 |
| 5,723,287 A | * | 3/1998 | Russell et al. ................. | 435/5 |

FOREIGN PATENT DOCUMENTS

| | | | |
|---|---|---|---|
| WO | WO 94/10323 | * | 5/1994 |
| WO | WO 94/26892 | | 11/1994 |
| WO | WO 95/26412 | | 10/1995 |
| WO | WO 97/05266 | | 2/1997 |

OTHER PUBLICATIONS

Sosnowski et al., The Journal Biological Chemistry, vol. 271(52), pp. 33647–33653, Dec. 1996.*
E. Marshal, Science, vol. 269, pp. 1052–1053, Aug. 25, 1995.*
Nabel et al., Annals New York Academy of Sciences, 714:247–252, Apr. 1994.*
Douglas et al., Nature Biotechnology, vol. 14, pp. 1574–1578, Nov. 1996.*
Ketteler et al., American J. of Physiology, vol. 267, No. 2, part 2, p. F197–F207, 1994.*
Verma et al., Nature, vol. 389, p. 239–242, Sep. 1997.*
Eck et al., Goodman & Gilman's The Pharmacological Basis of Therapeutics, Ninth Edition, McGraw–Hill, New York, Chapter 5: Gene–Based Therapy, p. 77–101, 1996.*
Douglas et al., "Targeted gene delivery by tropism–modified adenoviral vectors," *Nature Biotechnology 14*: 1574–1578, 1996.
Finch et al., "Human KGF is FGF–Related with Properties of a Paracrine Effector of Epithelial Cell Growth," *Science 245*(4919): 752–755, 1989.
Goldman et al., "Targeted Gene Delivery to Kaposi's Sarcoma Cells via the Fibroblast Growth Factor Receptor," *Cancer Research 57*: 1447–1451, 1997.
Hoganson et al., FGF2 retargeted adenoviral vectors mediate increased gene transfer, *Cancer Gene Therapy4*(6Conf. Suppl.): O–45, 1997.
Krasnykh et al., "Generation of Recombinant Adenovirus Vectors with Modified Fibers for Altering Viral Tropism," *Journal of Virology 70*(10): 6839–6846, 1996.
Michael et al., "Addition of a short peptide ligand to the adenovirus fiber protein," *Gene Therapy 2*: 660–668, 1995.
Miller et al., "Targeting adenoviral gene delivery to the epidermal growth factor receptor," *Cancer Gene Therapy 4* (6 Conf. Suppl.): P–95, 1997.
Reynolds et al., "Enhanced gene transfer to vascular endothelium using retargeted adenoviral vector," *Cancer Gene Therapy 4* (6 Conf. Suppl.): P–94, 1997.
Sosnowski et al., "Targeting DNA to Cells with Basic Fibroblast Growth Factor (FGF2)," *The Journal of Biological Chemistry 271*(52): 33647–33653, 1996.
Watkins et al., "Targeting adenovirus–mediated gene delivery with recombinant antibodies," *Immunotechnology* (1996 Keystone Meeting on Exploring and Exploiting Antobody and Ig Superfamily Combining Sites: Taos, New Mexico, USA) 2(4): 307, 1996.

* cited by examiner

*Primary Examiner*—Shin-Lin Chen
(74) *Attorney, Agent, or Firm*—Seed Intellectual Property Law Group PLLC

(57) ABSTRACT

The present invention relates to gene therapy. In particular, therapeutic agents, therapeutic gene products, and compositions are disclosed. Various systems and methods useful in targeting and delivering non-native nucleotide sequences to specific cells are disclosed, wherein virus-antibody-ligand conjugates are used to facilitate targeting and delivery.

7 Claims, 21 Drawing Sheets

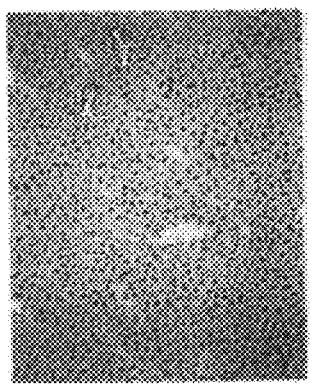 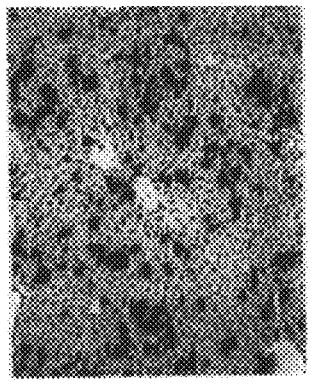 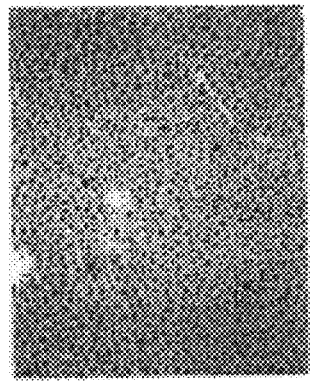
*Fig. 8A*  *Fig. 8B*  *Fig. 8C*

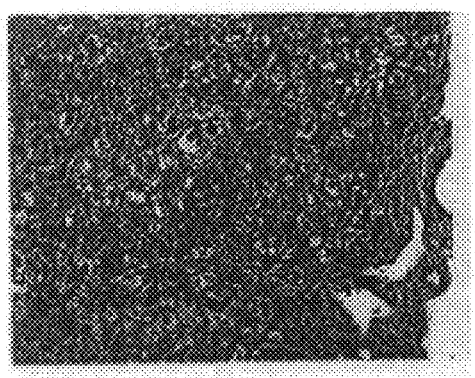 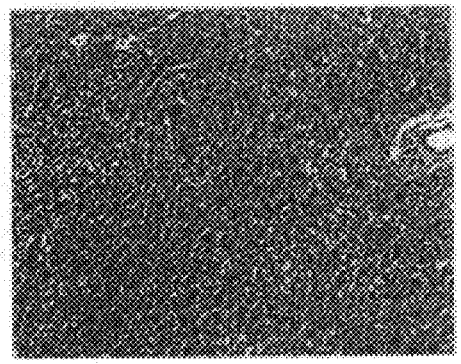
*Fig. 10A*   *Fig. 10B*

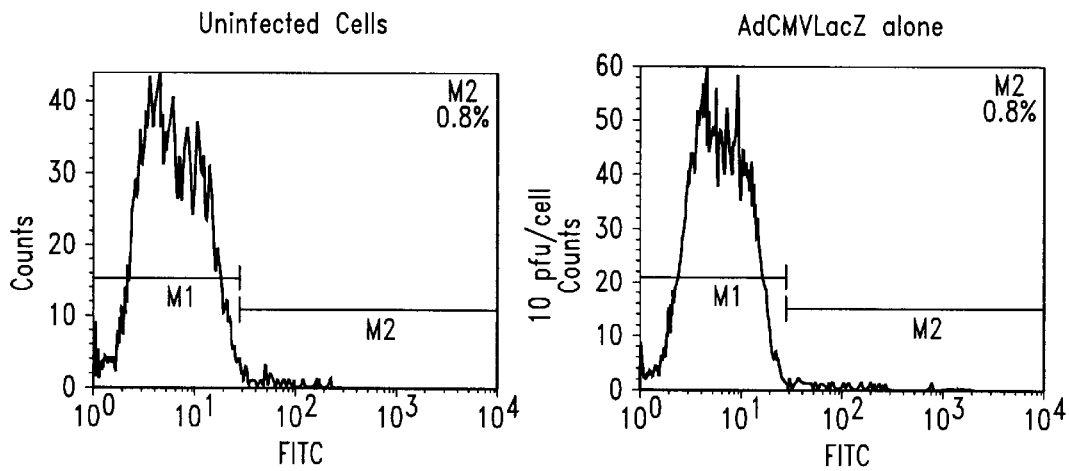
*Fig. 18A*  *Fig. 18B*
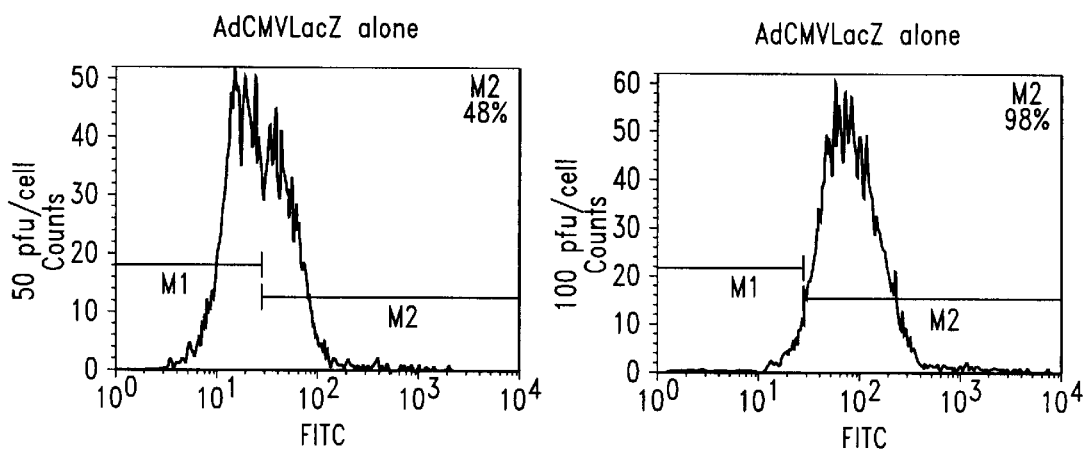
*Fig. 18C*  *Fig. 18D*

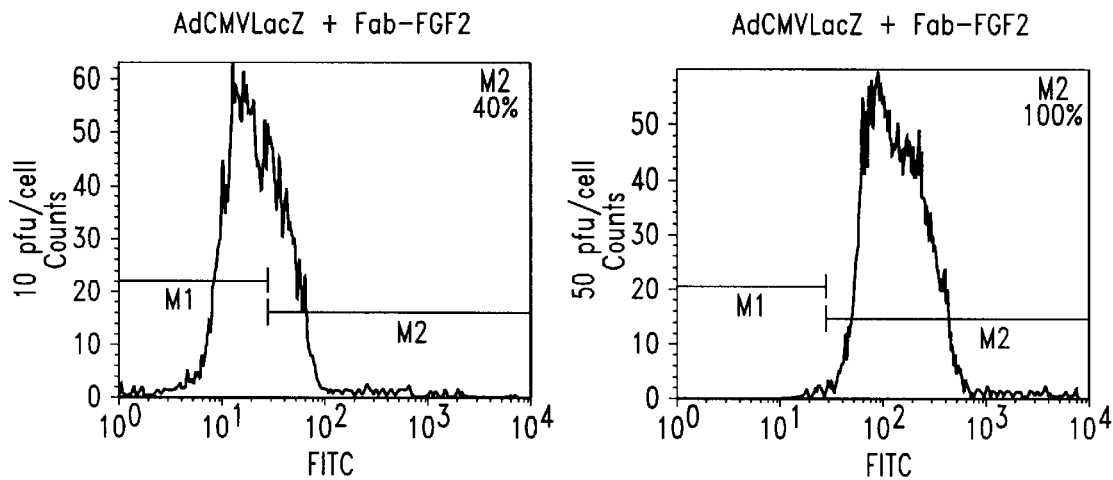
*Fig. 18E*  *Fig. 18F*
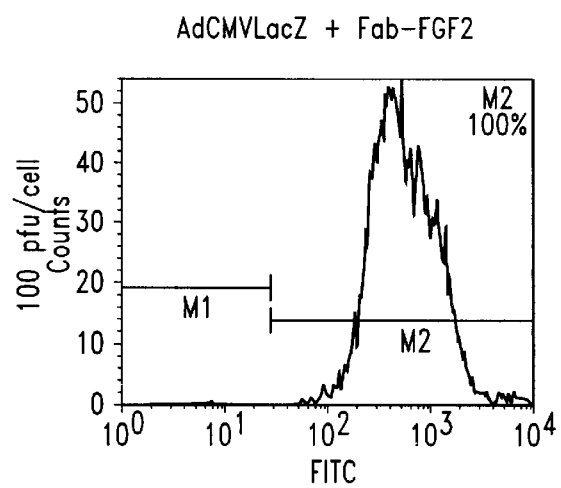
*Fig. 18G*

SEQUENCE LISTING

<160> NUMBER OF SEQ ID NOS: 6

<210> SEQ ID NO 1
<211> LENGTH: 35
<212> TYPE: DNA
<213> ORGANISM: Artificial Sequence
<220> FEATURE:
<223> OTHER INFORMATION: Sense Primer

<400> SEQUENCE: 1

-continued

```
atatagaatt ctgtgactac tgaggacaca gccac                          35

<210> SEQ ID NO 2
<211> LENGTH: 35
<212> TYPE: DNA
<213> ORGANISM: Artificial Sequence
<220> FEATURE:
<223> OTHER INFORMATION: Antisense Primer

<400> SEQUENCE: 2
atatacatat gttttttcag ctccagcttg gtccc                          35

<210> SEQ ID NO 3
<211> LENGTH: 17
<212> TYPE: DNA
<213> ORGANISM: Artificial Sequence
<220> FEATURE:
<223> OTHER INFORMATION: Oligonucleotide

<400> SEQUENCE: 3
aggagtgtct gctaacc                                              17

<210> SEQ ID NO 4
<211> LENGTH: 24
<212> TYPE: DNA
<213> ORGANISM: Artificial Sequence
<220> FEATURE:
<223> OTHER INFORMATION: Oligonucleotide

<400> SEQUENCE: 4
ttctaaatcg gttaccgatg actg                                      24

<210> SEQ ID NO 5
<211> LENGTH: 9
<212> TYPE: PRT
<213> ORGANISM: Artificial Sequence
<220> FEATURE:
<223> OTHER INFORMATION: Polypeptide capable of targeting receptors such
      as the CR2 receptor

<400> SEQUENCE: 5

Glu Asp Pro Gly Phe Phe Asn Val Glu
 1               5

<210> SEQ ID NO 6
<211> LENGTH: 11
<212> TYPE: PRT
<213> ORGANISM: Artificial Sequence
<220> FEATURE:
<223> OTHER INFORMATION: Polypeptide capable of targeting receptors such
      as the CR2 receptor

<400> SEQUENCE: 6

Glu Asp Pro Gly Lys Gln Leu Tyr Asn Val Glu
 1               5                  10
```

VIRAL VECTORS WITH MODIFIED TROPISM

CROSS-REFERENCE TO RELATED APPLICATIONS

This application claims the benefit of U.S. Provisional Application Ser. Nos. 60/040,782 and 60/065,265, filed Mar. 14, 1997 and Nov. 10, 1997, respectively. The disclosures of these applications are incorporated herein in their entirety by reference thereto.

TECHNICAL FIELD

The present invention relates to gene therapy. In particular, therapeutic agents and methods useful in targeting and delivering genes more efficiently to particular cells are disclosed, wherein re-targeted, tropism-modified viral vectors presenting ligand on the surface and including a nucleotide sequence encoding a therapeutic gene product are used to facilitate targeting and delivery.

BACKGROUND OF THE INVENTION

The primary impediment to the transfer of non-native or foreign DNA into mammalian cells is that the genetic material must be transported across multiple cellular barriers before it enters the host cell nucleus and initiates gene expression. Previously established methods have utilized artificial means to introduce DNA into the cell although these methods are associated with significant cell toxicity (Graham et al., *Virology* 52:456–467 (1973); Felgner et al, *PNAS USA* 84:7413–7417 (1987)).

More recently, enhanced transfer of DNA conjugates into cells has been achieved with adenovirus, a human DNA virus which readily infects various cell types (Horwitz, Adenoviridae and their replication, in *Virology*, Fields and Knipe, eds., Raven Press, NY (1990) pp. 1679–1740). Since adenovirus efficiently disrupts the membranes of endocytic vesicles, co-internalization of the virus with the DNA conjugate allows rapid transfer of the conjugate into the cell cytoplasm before it can be subjected to lysosomal degradation. The fact that adenovirus exhibits selective tropism has also been exploited to reconstitute these cells in vivo with the human cystic fibrosis transmembrane conductance regulator (CFTR) (Rosenfeld et at., *Cell* 68:143–155 (1992)) and the alpha 1-antitrypsin genes (Rosenfeld et al., *Science* 252:431–434 (1991)).

A number of features make adenoviruses very attractive for gene delivery applications. Knowledge of the adenovirus genetic system is fairly extensive, including the viral life cycle, DNA replication, transcription and RNA processing, and regulation of virus gene expression. In addition, the size of the adenovirus (Ad) genome allows relatively easy manipulation of the viral DNA while still having the capacity for insertion of most cDNAs into the viral genome. Additional advantages of adenovirus vectors include their ability to infect both dividing and nondividing cells efficiently, to induce high-level foreign protein expression without replication or integration of the viral genome, and to grow to high yields when propagated in an appropriate complementing cell line.

If a target tissue lacks sufficient levels of adenovirus attachment receptors to mediate viral adsorption, however, this may also be a barrier to efficient gene transfer. Infection by most viruses requires viral attachment to its host cell receptor. Adenovirus attaches to its host cell receptor via its fiber protein (see, e.g., Wickham et al., *Cell* 73:309–319 (1993)).

The Ad fiber protein is a long, trimeric protein that protrudes from the surface of the virion. At the distal end of the fiber protein is a knob-like C-terminus that interacts with an unidentified cellular receptor present on HeLa and other epithelial-derived carcinoma cell lines (see, e.g., Defer et al., *J. Virol.* 64:3661–3673 (1990)). The receptor, generally identified as FibR, is assumed to be expressed by cells that are the normal targets for adenovirus infection.

Thus, reduced gene delivery to certain tissues may well result from a low expression of the adenovirus receptor (FibR). A lack of functional receptors is thus likely to be directly correlated with dramatic reductions in gene transfer efficiency.

In general, adenoviral vectors possess the capacity for in vivo gene transfer that are critical to effective gene therapy. Following administration of the adenovirus vector, three distinct, sequential steps are required for expression of the therapeutic gene in target cells: (1) attachment of the adenovirus vector to specific receptors on the surface of the target cell; (2) internalization of the virus; and (3) transfer of the gene to the nucleus where it can be expressed. Thus, any attempt to modify the tropism of an adenovirus vector—that is, its native ability to target its cognate receptor must reserve its ability to perform these three functions efficiently.

Investigators have met with greater or lesser success in this regard. For example, the methodology proposed by Krasnykh et al. (*J. Virol.* 70: 6839–46 (1996) generates recombinant adenovirus with chimeric fibers having a fiber shaft from one Ad serotype and a knob from another, thereby altering the adenovirus' receptor recognition profile. (Also see Gall et al., *J. Virol.* 70:2116–2123 (1996), which describes an Ad 5/7 capsid chimera.) However, such constructs would appear to have limited utility, as they still rely on the less-than-ubiquitous (and less-than-efficient) Ad receptors for targeting. Moreover, Ad vectors that rely upon Ad receptors for targeting (and putative internalization) are not able to target as wide a variety of cells as one might wish, and depending on the nature of the chimeric fiber, any alterations in its conformation may have a negative impact on targeting and/or delivery.

Further, the modifications described in the aforementioned articles do not alter viral tropism in a manner that enhances viral targeting or increases trafficking to the nucleus, contrary to what is disclosed herein. In addition, the art fails to disclose targeting and delivery constructs and systems that achieve the unexpectedly high level of "infectivity" and expression shown herein. Finally, the constructs and methods of the present invention successfully achieved delivery of therapeutic agents to cells that are normally resistant to viral-mediated delivery.

In view of the aforementioned problems, the design and construction of the within-disclosed vectors and conjugates provides a novel and elegant solution, as described further herein. The use of the recombinant sequences and vectors of this invention to mediate the transfer of foreign genes into recipient cells both in vitro and in vivo overcomes the limitations of the above-described gene transfer systems. This invention utilizes recombinant constructs which confer the advantages of targeting via the fibroblast growth factor receptor upon adenovirus—in place of the adenovirus usual targeting via fiber protein—and thus represents an improved method for gene therapy as well as for therapeutic applications involving delivery of a gene.

BRIEF SUMMARY OF THE INVENTION

In contrast to the disadvantages of using intact adenovirus, modified adenovirus vectors requiring a helper plasmid or virus, or so-called replication-deficient adenovirus, the use of recombinant adenovirus-derived vectors according to the present invention provides certain advantages for gene delivery. In particular, adenoviral vectors having their native tropism modified or ablated, which are then re-targeted via a targeting ligand, are disclosed herein as advantageous for a variety of gene therapy applications.

The Ad-derived vectors of the present invention possesses all of the functional properties required for gene therapy including binding to specific cell receptors and penetration of endocytic vesicles. They further include those in which all or part of the fiber head or tail is replaced with—or conjugated to—a ligand-encoding gene. Use of the vectors and conjugates disclosed herein allows one to target a wide variety of cells and to deliver therapeutic agents—irrespective of whether those agents are proteins, polypeptides, nucleotide sequences, or some other molecular species—directly into specific target cells.

The presently-disclosed constructs, systems and methods afford a level of flexibility in therapeutic approaches not seen with other systems and methods. Therefore, the vectors, systems and methods of the present invention are ideal for use in a wide variety of therapeutic applications.

Therefore, in one embodiment, the present invention provides a tropism-modified adenoviral vector system that specifically targets cells expressing a preselected receptor, comprising an antibody or fragment thereof that binds an adenoviral capsid protein; a targeting ligand that binds the preselected receptor; and an adenovirus containing a nucleic acid molecule that encodes a therapeutic gene product under the control of a promoter; wherein the ligand is conjugated to the antibody or fragment thereof and wherein the antibody or fragment thereof is bound to the adenovirus. In one variation, the ligand is conjugated to the antibody or fragment thereof as a fusion, e.g., a fusion-sF$_v$. In another variation, the promoter is a tissue-specific promoter.

In another embodiment, a tropism-modified adenoviral vector is provided wherein the targeting ligand is a polypeptide reactive with an FGF receptor. In one variation, the polypeptide reactive with an FGF receptor is an antibody or fragment thereof. In another variation, the antibody is a single-chain antibody. In one alternative embodiment, the antibody is 11A8. In another, the polypeptide reactive with an FGF receptor is selected from the group consisting of FGF-1, FGF-2, FGF-3, FGF-4, FGF-5, FGF-6, FGF-7, FGF-8, FGF-9, FGF-11, FGF-13, FGF-14, FGF-15, and molecules having 20% or greater homology to any of the foregoing. In still another embodiment, the polypeptide reactive with an FGF receptor is FGF-2. Yet another variation provides that the targeting ligand is selected from the group consisting of a polypeptide reactive with a VEGF receptor, a polypeptide reactive with a PDGF receptor, and a polypeptide reactive with an EGF receptor.

In other variations of the disclosed invention, the surface-presented ligand is a polypeptide reactive with a cell-surface receptor; growth factor receptors are one class of receptors contemplated within the scope of the present invention. Another class of receptors contemplated within the scope of the invention includes receptors for Her-2/neu or erbB2. Thus, a polypeptide reactive with a cell-surface receptor according to the present invention includes antibodies or fragments thereof, including single-chain antibodies, which react with receptors for Her-2/neu or erbB2.

The present invention also discloses embodiments wherein the native tropism of the viral vector is modified; in still other embodiments, the native tropism of the viral vector is ablated. In various preferred embodiments, the vector is an adenoviral vector. The adenoviral vector is readily selected from any of the adenovirus serotypes, as well.

In a further aspect of the present invention, a tropism-modified vector is disclosed wherein the therapeutic gene product is a cytocide or a prodrug. In one set of related embodiments, the cytocide is a ribosome inactivating protein. In other variations, the gene product is thymidine kinase, cytosine deaminase, or nitroreductase.

According to various embodiments of the present invention, the therapeutic gene product enhances cellular proliferation. In one variation, the therapeutic gene product is a biologically active protein or polypeptide that augments or complements an endogenous protein. In another variation, the therapeutic gene product enhances cellular differentiation. In still another variation, the therapeutic gene product is a molecule which enhances tissue repair or regeneration. Yet another variation provides that the therapeutic gene product is a molecule which stimulates a protective immune response.

The present invention further discloses a variety of pharmaceutical compositions. In one embodiment, a pharmaceutical composition of the present invention comprises a physiologically acceptable buffer and a tropism-modified adenoviral vector presenting a ligand on its surface, wherein the vector includes a nucleic acid molecule encoding a therapeutic gene product under the control of a promoter. In one variation, the ligand is a polypeptide reactive with an FGF receptor. In various alternative embodiments, the polypeptide reactive with an FGF receptor is selected from the group consisting of FGF-1, FGF-2, FGF-3, FGF-4, FGF-5, FGF-6, FGF-7, FGF-8, FGF-9, FGF-11, FGF-13, FGF-14, and FGF-15. In one preferred variation, the polypeptide reactive with an FGF receptor is FGF-2. In other embodiments, the polypeptide reactive with an FGF receptor is an antibody or fragment thereof. In one alternative variation, the antibody is a single-chain antibody. In another variation, the antibody is 11A8.

In other variations of the disclosed invention, the surface-presented ligand is a polypeptide reactive with a cell-surface receptor; growth factor receptors are one class of receptors contemplated within the scope of the present invention. Another class of receptors contemplated within the scope of the invention includes receptors for Her-2/neu or erbB2. Thus, a polypeptide reactive with a cell-surface receptor according to the present invention includes antibodies or fragments thereof, including single-chain antibodies, which react with receptors for Her-2/neu or erbB2.

In various aspects of the present invention, the ligand is genetically fused with an adenoviral capsid protein. In others, the ligand is chemically conjugated to an adenoviral capsid protein. In one variation, the ligand is conjugated to an antibody or fragment thereof that binds a viral capsid protein. In another variation, the ligand is conjugated to the antibody or fragment thereof as a fusion, e.g., a fusion-sc-F$_v$.

Other variations contemplate that the therapeutic gene product is selected from the group consisting of protein, ribozyme and antisense. In one alternative embodiment, the therapeutic gene product is a cytocide. Exemplary cytocides include ribosome-inactivating proteins. In another embodiment, the therapeutic gene product is a prodrug. Exemplary prodrugs include thymidine kinase, cytosine deaminase, or nitroreductase. Other embodiments disclose a wide variety of therapeutic gene products, including products that replace or repair defective, improperly regulated, or nonfunctional genes. In various alternative embodiments, therapeutic gene products within the context of the present invention stimulate wound healing, tissue repair, connective tissue growth, angiogenesis, or the amelioration of ischemia, to name a few examples. In other embodiments, therapeutic gene products treat, interfere with or block a disease process, such as hyperproliferation of cells, tumor growth, metastasis, and the like.

Thus, the present invention also discloses a variety of treatment methods. In one embodiment, the invention contemplates a method of treating tumors, comprising administering a pharmaceutical composition comprising a physiologically acceptable buffer and a tropism-modified adenoviral vector presenting a ligand on its surface, wherein the vector includes a nucleotide sequence encoding a therapeutic gene product under the control of a promoter, wherein the therapeutic gene product is selected from the group consisting of E-cadherin, BGP, Rb, p53, CDKN2/P16/ MTS1, PTEN/MMAC1, APC, p33ING1, Smad4, maspin, VHL, WT1, Men1, NF2, MXI1, and FHIT. The invention also provides methods of treating ischemia, comprising administering a pharmaceutical composition comprising a physiologically acceptable buffer and a tropism-modified adenoviral vector presenting a ligand on its surface, wherein the vector includes a nucleotide sequence encoding a therapeutic gene product under the control of a promoter, wherein the therapeutic gene product is selected from the group consisting of IGF, TGFβ1, TGFβ2, TGFβ3, HGF, VEGF 121, VEGF 165, FGF1, FGF2, FGF4, FGF5, PDGF-A, and PDGF-B.

In still other variations, the invention provides methods of treating connective tissue injury, comprising administering a pharmaceutical composition comprising a physiologically acceptable buffer and a tropism-modified adenoviral vector presenting a ligand on its surface, wherein the vector includes a nucleotide sequence encoding a therapeutic gene product under the control of a promoter, wherein the therapeutic gene product is selected from the group consisting of PTH, BMP1, BMP2, BMP3, BMP4, BMP5, BMP6, BMP7, BMP8, BMP10, BMP11, mammalian BMP, and Xenopus BMP. An alternative method comprises the administration of a pharmaceutical composition comprising a physiologically acceptable buffer and a tropism-modified adenoviral vector presenting a ligand on its surface, wherein the vector includes a nucleotide sequence encoding a therapeutic gene product under the control of a promoter, wherein the therapeutic gene product is selected from the group consisting of Bovine VEGF, VEGF, VEGF-B, VEGF-C, Angiopoietin-1, Angiogenin, IGF-1, IGF-II, HGF, PDGF A, PDGF B, TGFB1, TGFB2, and TGFB3.

The present invention also discloses various methods of treating malignancies, including cancer. In one such embodiment, a method of treating cancer is disclosed, comprising contacting the cancer cells with a pharmaceutical composition comprising a physiologically acceptable buffer and a tropism-modified adenoviral vector presenting a ligand on its surface, wherein the vector includes a nucleotide sequence encoding a therapeutic gene product under the control of a promoter, wherein the therapeutic gene product is selected from the group consisting of HSVTK, VZVTK, nitroreductase, and cytosine deaminase; and contacting the cancer cells with a substrate. In various embodiments, the substrate is a molecule that is acted upon to produce a molecule that is cytotoxic or cytostatic to the cancer cells.

In the various disclosed methods, the ligand is a polypeptide reactive with a specific cellular receptor; various polypeptides useful in this regard are recited hereinabove. In various preferred embodiments, the receptor is an FGF receptor. In one variation, the polypeptide reactive with an FGF receptor is FGF-2. In other variations, the polypeptide reactive with an FGF receptor is selected from the group consisting of FGF-1, FGF-2, FGF-3, FGF-4, FGF-5, FGF-6, FGF-7, FGF-8, FGF-9, FGF-11, FGF-13, FGF-14, and FGF-15.

In one alternative embodiment, the ligand is an antibody or a fragment thereof In another embodiment, the antibody is a single-chain antibody. In yet another variation, the ligand is conjugated to an antibody or fragment thereof that binds a viral capsid protein. In various embodiments, the viral capsid protein is adenovirus fiber protein—for example, an adenovirus knob protein. In yet other embodiments, the ligand may be chemically conjugated to a protein on the surface of a viral vector or may be attached to the capsid as a component of a fusion protein.

In various methods disclosed herein, the therapeutic gene product is selected from the group consisting of protein, ribozyme and antisense. In one alternative embodiment, the therapeutic gene product is a cytocide. Exemplary cytocides include ribosome-inactivating proteins. In another embodiment, the therapeutic gene product is a prodrug. Exemplary prodrugs include thymidine kinase, nitroreductase, and cytosine deaminase. Other embodiments disclose a wide variety of therapeutic gene products, including products that replace or repair defective, improperly regulated, or nonfunctional genes. In various alternative embodiments, therapeutic gene products within the context of the present invention stimulate wound healing, tissue repair, connective tissue growth, angiogenesis, or the amelioration of ischemia, to name a few examples. In other embodiments, therapeutic gene products treat, interfere with or block a disease process, such as hyperproliferation of cells, tumor growth, metastasis, and the like.

These and other aspects of the present invention will become evident upon reference to the following detailed description and attached drawings. In addition, various articles and documents are referenced herein to provide further details regarding various procedures, compositions, molecules, and the like. It is expressly to be understood that the disclosures of all publications referred to herein are incorporated by reference in their entirety as though fully set forth herein.

BRIEF DESCRIPTION OF THE DRAWINGS

FIG. 3 illustrates enhanced AdCMVHSVtk/GCV cell killing in KSY-1 and KS-SLK cells by Fab-FGF2 conjugate. The effect of GCV on AdCMVHStk-transfected cells was assessed in the presence or absence of the conjugate and expressed as a percentage of cells surviving compared to the cell not exposed to GCV (i.e., -GCV). Viable cells in duplicate wells were counted, in triplicate, after trypan blue exclusion. On the vertical axis, the % of cells surviving is shown, in both FIGS. 3A and 3B.

FIG. 5 shows the results of SDS-PAGE of Fab-FGF2 under non-reducing conditions. Equal amounts (2 ug) of FGF2 (lane 2), Fab (lane 3), or Fab-FGF2 (lane 4) were applied to the gel and compared to the molecular weight standards (lane 1, in thousands) by staining with Coomassie blue.

FIG. 6 shows functional validation of the Fab-FGF2 conjugate.

FIG. 7 illustrates the results of in vitro infection of a panel of cell lines using the Fab-FGF2 conjugate.

FIGS. 8A-C illustrate the expression of β-galactosidase in the liver of mice after treatment with Adβgal or FGF2-Adβgal. In FIG. A, no Xgal stained cells in the liver of C57B1/6 mice treated with excipient are seen. In FIG. 8B, numerous Xgal stained hepatocytes are present in the liver of C57B1/6 mice treated with Adβgal at a dosage of 2×10$^{10}$ pfu per mouse, i.v. In FIG. 8C, treatment with FGF2-Adβgal at 2×10$^{10}$ pfu per mouse, i.v. transduces very few hepatocytes.

FIGS. 10A and 10B illustrate the histopathology of the liver of mice after treatment with Adβgal or FGF2-Adβgal. Hematoxylin and eosin stained paraffin sections of the liver of C57B1/6 mice treated with either Adβgal, 2×10e10 pfu, i.v. (FIG. 10A); or FGF2-Adβgal, 2×10e10 pfu, i.v. (FIG. 10B). Extensive hepatocellular necrosis and inflammatory infiltrate present in the liver of mice treated with Adβgal. There is nearly complete abrogation of hepatocellular necrosis in the liver of mice treated with FGF-2Adβgal. Also, very little inflammatory infiltrate is observed.

FIGS. 18A–18G show the flow cytometry analysis of β-galactosidase transduction. HUVECs infected at 10, 50 or 100 pfu/cell with AdCMVLacZ or AdCMVLacZ+Fab-FGF. Determination of gene expression 48 hours later by FDG staining and flow cytometry analysis. Representative profiles are shown, positive signal indicated by M2 gate.

DETAILED DESCRIPTION OF THE INVENTION

Figure 1:
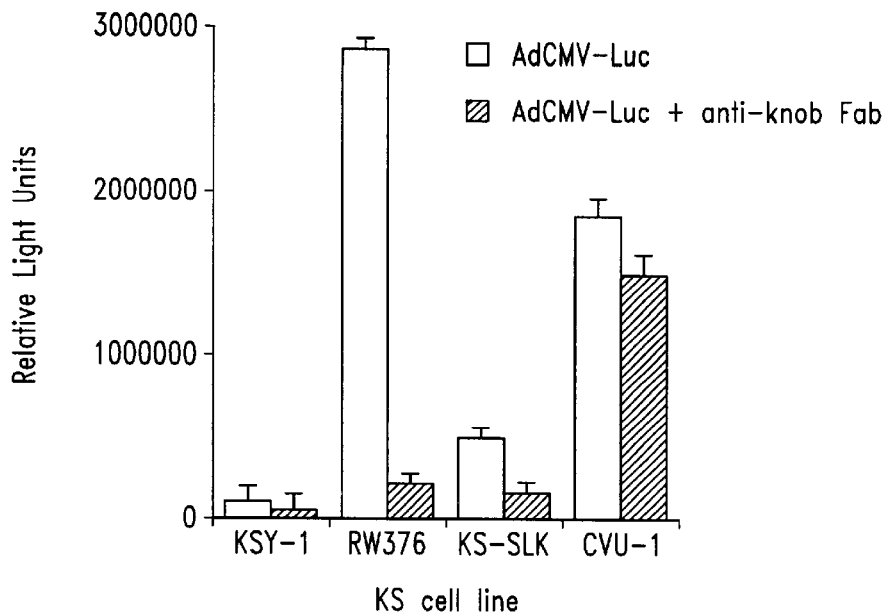
FIG. 1 shows a comparison of AdCMV-Luc transduction for four KS cell lines. KS cells were incubated with recombinant adenovirus expressing luciferase in the absence or presence of a Fab fragment blocking adenoviral knob-mediated infection. Experiments were performed in triplicate. Relative light units (RLU) are shown on the vertical axis; across the horizontal axis, the following cell lines are indicated: KSY-1; RW376; KS-SLK; and CVU-1. The open (colorless) bar represents AdCMV-Luc, while the closed (dark) bar represents AdCMV-Luc+anti-knob Fab.
Figure 2:
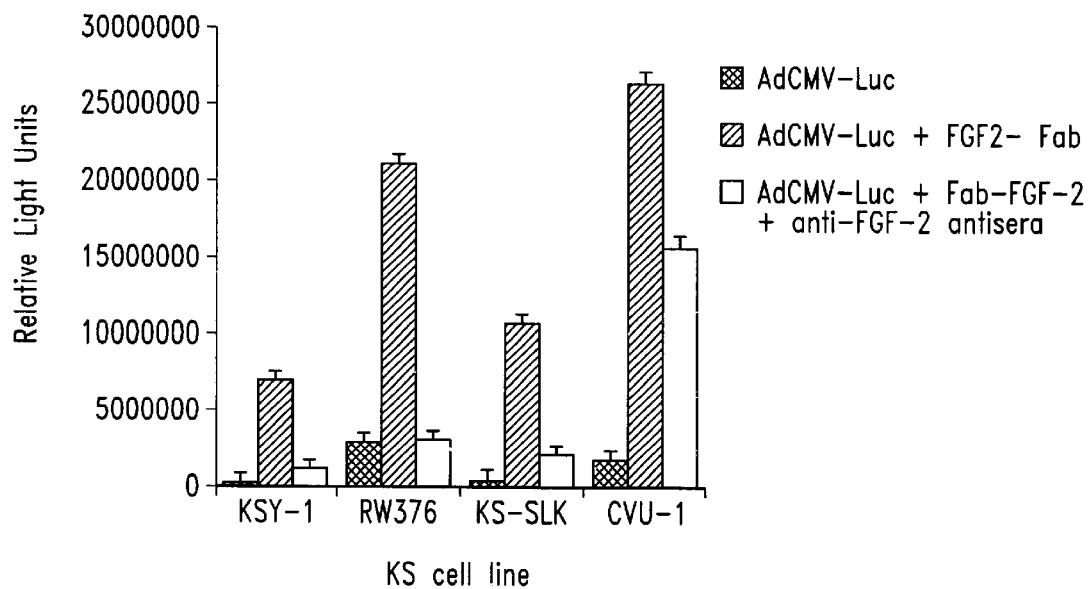
FIG. 2 shows the enhanced AdCMV-Luc infectivity of KS cell lines by Fab-FGF2 conjugate. The enhanced infectivity of the Ad-conjugate complex was assessed in the presence and absence of anti-FGF2 antisera. Relative light units (RLU) are plotted on the vertical axis, while the relevant KS cell lines—KSY-1, RW376, KS-SLK, and CVU-1—are indicated on the horizontal axis. The closed bars represent AdCMV-Luc; stippled bars represent AdCMV-Luc+Fab-FGF2; and the open (colorless) bars represent AdCMV-Luc+ Fab-FGF2+anti-FGF2 antisera.

Many of the findings and results disclosed herein are quite unexpected. For example, we have found that FGF retargeting of an adenovirus—i e., altering the tropism of an adenovirus using a fibroblast growth factor—significantly enhances targeting efficiency and nuclear trafficking of the Ad vector well above that seen when the vector retains its native Ad tropism. In addition, we observed that FGF retargeting increases the infectability of adenovirus in various cells—e.g., cells expressing Kaposi's sarcoma—compared to the use of native Ad tropism alone. Interestingly, we found this to be true even in those cell lines that were resistant to Ad infection.

Third, we found that the use of FGF retargeted vectors enhances potency; FGF-retargeted vectors deliver and promote the expression of a therapeutic gene to more target cells and in each cell so targeted. Fourth, the vectors of the present invention are significantly less toxic to the liver and are less immunogenic than are other Ad vectors. Finally, we observed that retargeting the viral vector retargeted with FGF induces cytotoxicity to specific cell types when therapeutic gene sequences (e.g cytotoxic sequences, such as HSV-tk) are delivered; FGF retargeted vectors are thus able to transduce cells which are normally insensitive to Ad infection.

Thus, the FGF-retargeted vectors and related compositions and methods of the present invention are unexpectedly and significantly superior to other gene therapy vectors, particularly viral vectors. And while the retargeting of Ad vectors has been described herein as exemplary, it should be appreciated that other viral and non-viral vectors may benefit from the retargeting strategies disclosed herein.

Therefore, the present invention makes it feasible to engineer and produce novel constructs and vectors that are able to package and deliver effective amounts of therapeutic agents or nucleic acid sequences encoding same for efficacious use in a variety of therapeutic applications, without endangering the subject to whom they are administered.

A. Definitions

Prior to setting forth the invention, it will be helpful to an understanding thereof to define certain terms used herein. The "amino acids," which occur in the various amino acid sequences appearing herein, are identified according to their well known three letter or one letter abbreviations. The nucleotides, which occur in the various DNA fragments, are designated with the standard single letter designations used routinely in the art.

As used herein, to "bind to a receptor" refers to the ability of a ligand to specifically recognize and detectably bind to a receptor, as assayed by standard, e.g., in vitro, assays.

As used herein, a "conjugate" refers two or more molecules that are linked together. The molecules may be conjugated directly or through a linker, such as a peptide, or they may be held together via ionic or other intermolecular forces. A conjugate may be produced by chemical coupling methods or by recombinant expression of chimeric DNA molecules to produce fusion proteins.

A "cytocide-encoding agent" is a nucleic acid molecule that encodes a product that results in cell death and generally acts by inhibiting protein synthesis. Such a product may act by cleaving rRNA or ribonucleoprotein, inhibiting an elongation factor, cleaving mRNA, or other mechanism that reduces protein synthesis to a level such that the cell cannot survive. The product may be a protein, ribozyme, antisense, and the like. The nucleic acid molecule may contain additional elements besides the cytocide gene. Such elements include a promoter, enhancer, splice site, transcription terminator, poly(A) signal sequence, bacterial or mammalian origin of replication, selection marker, and the like.

"Heparin-binding growth factor" refers to any member of a family of heparin-binding growth factor proteins, in which at least one member of the family binds heparin. Preferred growth factors in this regard include fibroblast growth factor (FGF), vascular endothelial growth factor (VEGF), and heparin binding EGF-like factor (HBEGF). Such growth factors encompass isoforms, peptide fragments derived from a family member, splice variants, and single or multiple exons, some forms of which may not bind heparin.

"Nucleic acid binding domain" (NABD) refers to a molecule, usually a protein, or peptide (but may also be a polycation) that binds nucleic acids, such as DNA or RNA. An NABD may bind to single or double strands of RNA or DNA or mixed RNA/DNA hybrids. The nucleic acid binding domain may bind to a specific sequence or bind irrespective of the sequence.

As used herein, "nucleic acid" refers to RNA or DNA that is intended for internalization into a cell and includes, but is not limited to, DNA encoding a therapeutic protein, a cytotoxic protein, a prodrug, a ribozyme, a deoxyribozyme, or antisense, the complement of these NAs, an antisense nucleic acid, and other such molecules. Reference to nucleic acids includes duplex DNA, single-stranded DNA, RNA in any form, including triplex, duplex or single-stranded RNA, anti-sense RNA, polynucleotides, oligonucleotides, single nucleotides, chimeras, and derivatives thereof. Nucleic acids may be composed of the well-known deoxyribonucleotides and ribonucleotides (i.e., the bases adenosine, cytosine, guanine, thymidine, and uridine). As well, various other nucleotide derivatives, non-phosphate backbones or phosphate-derived backbones may be used. For example, because normal phosphodiester oligonucleotides (referred to as PO oligonucleotides) are sensitive to DNA- and RNA-specific nucleases, oligonucleotides resistant to cleavage, such as those in which the phosphate group has been altered to a phosphotriester, methylphosphonate, or phosphorothioate may be used (see U.S. Pat. No. 5,218,088).

As used herein, "receptor-binding internalized ligand" or "ligand" refers to any peptide, polypeptide, protein or non-protein, such as a peptidomimetic, that is capable of binding to a cell-surface molecule and internalization. Within the context of this invention, the receptor-binding internalized ligand is conjugated to a nucleic acid binding domain, either as a fusion protein or through chemical conjugation, and is used to deliver a neuronal therapeutic-encoding agent to a cell. In one aspect, the ligand is directly conjugated to a nucleic acid molecule, which may be further complexed with a nucleic acid binding domain. Such ligands include growth factors, cytokines, antibodies, hormones, and the like.

As used herein, a "targeted agent" is a chemical agent that is usually a nucleic acid molecule, but that may also be a protein, a carbohydrate, a lipid or any other class of chemical agent that is internally delivered to a cell by a receptor-binding internalized ligand, and upon internalization alters or affects cellular metabolism, growth, activity, viability or other property or characteristic of the cell.

As used herein, a "therapeutic nucleic acid" describes any nucleic acid molecule used in the context of the invention that effects a treatment, generally by modifying gene transcription or translation. It includes, but is not limited to, the following types of nucleic acids: nucleic acids encoding a protein, antisense RNA, DNA intended to form triplex molecules, protein binding nucleic acids, and small nucleotide molecules. A therapeutic nucleic acid may be used to effect genetic therapy by serving as a replacement for a defective gene, or by encoding a therapeutic product, such as a tumor-suppressing agent, prodrug, proliferation enhancer, or cytocide, to name a few examples. The therapeutic nucleic acid may contain all or a portion of a gene and may function by recombining with DNA already present in a cell, thereby replacing or complementing a defective portion of a gene. It may also encode a portion of a protein and exert its effect by virtue of co-suppression of a gene product.

As used herein, "operative linkage" or operative association of two nucleotide sequences refers to the functional relationship between such sequences. Nucleotide sequences include, but are not limited to, DNA encoding a product, DNA encoding a signal sequence, promoters, enhancers, transcriptional and translational stop sites, and polyadenylation signals. For example, operative linkage of DNA encoding a therapeutic gene product to a promoter refers to the physical and functional relationship between the DNA and the promoter such that transcription of the DNA is initiated from the promoter by an RNA polymerase that specifically recognizes, binds to, and transcribes the DNA.

As used herein, the phrase "polypeptide reactive with an FGF receptor" refers to any polypeptide that specifically interacts with an FGF receptor (e.g. the high affinity FGF receptor), and is transported into the cell by virtue of its interaction with the FGF receptor.

As used herein, a "prodrug" is a compound that metabolizes or otherwise converts an inactive, nontoxic compound to a biologically, pharmaceutically, therapeutically, or toxic active form of the compound. A prodrug may also be a pharmaceutically inactive compound that is modified upon administration to yield an active compound through metabolic or other processes. By virtue of knowledge of pharmacodynamic processes and drug metabolism in vivo, once a pharmaceutically active compound is known inactive forms of the compound may be synthesized or isolated (see, e.g., Nogrady, *Medicinal Chemistry A Biochemical Approach*, Oxford University Press, New York, pages 388–392, 1985).

As used herein, "receptor-binding internalized ligand" or "ligand" refers to any peptide, polypeptide, protein or non-protein, such as a peptidomimetic, that is capable of binding to a cell-surface molecule and internalizing. Within the context of this invention, the receptor-binding internalized ligand may be conjugated to a viral capsid protein, either as a fusion protein or through chemical conjugation, either directly or indirectly (e.g. via a bispecific antibody). By way of further example, the ligand may be conjugated to the antibody or fragment thereof as a fusion, e.g., a fusion-$sF_v$. Receptor-binding internalized ligands may thus be used to deliver therapeutic product-encoding agents to cells. Such ligands include growth factors, cytokines, antibodies, hormones, and the like.

A "wound site" as used herein is defined as any location in the host that arises from traumatic tissue injury, or alternatively, from tissue damage either induced by, or resulting from, surgical procedures.

B. Viral Vectors With Altered Tropism

Viruses—particularly adenoviruses—have not often been considered to be ideal candidates for clinically-useful vectors, as their native tropism causes them to be quite infective, as well as highly immunogenic and toxic. These principal difficulties, as well as others which relate to the virus' native tropism, have been encountered by others of skill in the art—and those difficulties have not been successfully overcome.

For example, the native forms of most (if not all) viral and retroviral vectors—that is, vectors possessing their native tropism—are unable to efficiently target potential host cells. This low targeting efficiency may be due to the failure of cells to express the appropriate receptors or to express sufficient quantities of those receptors. In many instances, failure of the vector to escape the endosome to reach the nucleus is a relevant factor, as well.

Merely altering the tropism of a vector, without more, may not be sufficient to overcome the foregoing problems, however. For example, Douglas et al. described a method for ablating native Ad tropism while conferring new tropism through the use of an anti-knob antibody which was conjugated to folic acid for targeting Ad to folate receptor-positive cells (Douglas et al., *Nature Biotech*. 14:1574–1578 (1996)). While the tropism-modified Ad was able to transduce folate receptor-positive cells in vitro, the targeting efficiency was not as remarkable as that seen using the constructs and methods disclosed herein. Furthermore, delivery of the viral "payload" to the nucleus was not optimal.

Therefore, it is one goal of the present invention to design and construct viral constructs that have their native tropism modified (altered) or ablated (blocked). A further goal comprises modification of the virus in some fashion—e.g., genetically or immunologically—to provide the virus with a new target. For example, preferred viral constructs of the present invention possess the ability to target particular cell types.

Thus, as used herein, the term "tropism" refers to the movement or targeting of a viral vector (including viruses and viral particles) toward a receptor. Consistent with the foregoing, if a viral vector is displaying its native tropism, it is targeting its cognate receptor.

In the context of adenovirus (Ad), it tends to bind to integrin receptors, which is believed to be required for subsequent internalization of adenovirus into the host cell. Adenoviruses attach to host-cell receptors via the penton fiber glycoprotein and enter cells through the process of receptor-mediated endocytosis mediated by the penton base. Ad apparently utilizes separate proteins for attachment and entry in a manner similar to enveloped human viruses.

The terms "retargeted," "reprogrammed," "tropism-modified," or "altered tropism," particularly as applied to viruses and viral vectors, are often used interchangeably herein and are meant to identify viral vectors whose endogenous (or native) tropism has been ablated or modified. In one variation, the native tropism of the viral vector is either unchanged, or it is modified, or even ablated; but the viral vector also includes a ligand which conveys an altered (i.e. non-native) tropism. As noted, such a modification may be partial—i.e., the viral vector retains at least a portion of its native tropism—or it may be complete, whereby the native tropism of the viral vector is completely ablated.

The terms "tropism-modified," "altered tropism," and "reprogrammed," as applied to viruses and viral vectors, also encompass viruses and vectors whose native tropism has been altered in some way (e.g., partially modified, or fully ablated) but which may not include a ligand which confers a new tropism to the vector. And while the term "retargeted" is occasionally used to describe such vectors, it is more appropriately used to describe vectors that do include a ligand which confers a new tropism to the vector. One should readily be able to discern from the context of the description herein which variation is being described at any given point in the specification.

1. Altering Viral Tropism

The development of viral vectors targeted to specific cell types will enhance their clinical application in the field of human gene therapy. To this end, several studies have focused on altering adenovirus (Ad) tropism to direct the virus to cellular receptors other than the native cellular receptor by either expanding or limiting tropism. The former concept has been investigated in order to promote gene transfer in cells that are otherwise refractory towards Ad infection, while the latter approach targets Ad vectors to specific cell types and limit gene transfer in non-target tissues. (See, e.g., Wickham et al., *Nature Biotech*. 14:1570–1573 (1996); Wickham et al., *J. Virol*. 70:6831–6838 (1996).)

While such studies employ different approaches for expanding Ad tropism, they do not address the issue of whether it may be appropriate to modify native Ad tropism or to completely ablate native Ad tropism, which may well be necessary for effective clinical use in the context of cancer gene therapy, for example. The present invention further addresses the contexts in which one may wish to re-target an Ad vector without altering its native tropism at all; when one may wish to modify Ad tropism by re-targeting it and by diminishing its native tropism; and when one may wish to re-target Ad and completely ablate its native tropism.

We have discovered novel ligands that possess a remarkable and unrivaled ability to target specific cell types. Even more surprisingly, these same ligands are consistently trafficked to the cell nucleus in significant quantity. As a result, these ligands are particularly desirable for use in the targeting and delivery of a wide variety of "payloads" such as therapeutic nucleotide sequences encoding therapeutic gene products, and other molecules and agents that may impact nuclear and cellular functions.

For example, the use of FGF ligands and related moieties as efficient targeting and delivery agents is disclosed herein. When such ligands are linked in some fashion to a viral vector whose native tropism has been blocked or otherwise ablated, targeting efficiency increases dramatically, as does trafficking of the ligand (and anything conjugated or otherwise linked thereto) to the nucleus. Since FGF ligands are associated with a wide variety of diseases and as their cognate receptors are expressed on a variety of cell types, such ligands are ideal for use in the delivery of toxins in vitro and in vivo.

Moreover, when FGF ligands are used in conjunction with viral vectors—i.e., to confer a new tropism on such vectors—they are ideal for use in the delivery of therapeutic nucleotide sequences, as well. When a viral vector possesses the ability to efficiently deliver genetic material in vitro and in vivo—and Ad vectors are one such example—the combination of FGF-related ligands and viral vectors with modified tropism is a powerful combination indeed.

As described in greater detail below, it has now been observed that Ad-mediated gene transfer using a conjugate including an FGF-related ligand is greater than the level of gene transfer when Ad alone is used. Other conjugates—e.g. the Fab-folate conjugate of Douglas, et al. (Id., 1996) have not been able to facilitate Ad-mediated gene transfer as efficiently as conjugates including FGF-related ligands. Indeed, many such conjugates (including the Fab-folate conjugate) are not even able to reach the level achieved with Ad alone.

Irrespective of the explanation for the remarkable ability of FGF-related ligands to achieve extremely efficient targeting and delivery into specific cells, exploitation of this ability leads to the development of viral vectors with new tropisms and enhanced gene-delivery potential.

2. Exemplary Virus: Adenovirus

Since its discovery in 1953, the adenovirus has served as a model for molecular biology and cell transformation. The pentagonal capsomere (the penton) at the vertex of the adenovirus icosahedron consists of a fiber projection, linked by noncovalent bonds to the penton base, anchored in the capsid. (See, e.g., Novelli and Boulanger, *Virology* 185:365–376 (1991); Nermut, in *The Adenoviruses*, Ginsberg, ed., Plenum, N.Y., pp. 5–34 (1984); and Pettersson, in *The Adenoviruses*, Ginsberg, ed., Plenum, N.Y., pp. 205–207 (1984).)

Adenoviruses are nonenveloped, regular icosahedrons (20 triangular surfaces and 12 vertices) that are about 65–80 nm in diameter (about 1400 angstroms (Å)). A structure, called fiber, projects from each of the vertices. The length of the fiber varies with the adenovirus serotype. The protein coat or capsid is composed of 252 subunits (capsomeres), of which 240 are hexons and 12 are pentons. Each of the pentons contains a penton base on the surface of the capsid and a fiber projecting from the base, which is surrounded by five hexons. The name penton is derived from these geometric relationships.

With regard to virion capsid polypeptides, most of the detailed structural studies of adenovirus polypeptides have been performed for Ad types 2 and 5. Many of the tropism-modified vectors disclosed herein are thus derived from the "better-characterized" Ad serotypes such as Ad 2, Ad 5, and Ad 21. However, due to the relative similarity and homology among the various human Ad serotypes, Ad vectors derived from any of the serotypes presently identified may be modified as disclosed herein. Human adenovirus serotypes from type 1 through 47 are currently available from the American Type Culture Collection (ATCC), Rockville, Md. and may thus be able to function effectively as vectors, particularly when modified according to the within-disclosed invention.

It should be understood that viral vectors of the present invention may be constructed using any appropriate and useful viral serotype. The invention is thus not limited to a particular serotype or serotypes.

All human adenoviruses examined to date encode a single fiber protein with the exception of Ad40 and Ad41, which encode two fiber proteins and incorporate both polypeptides into their virions. Since the fiber interacts with a cellular receptor protein, these viruses might recognize two independent receptors. Fiber plays a crucial role in adenovirus infection by attaching the virus to a specific receptor on the cell surface.

Adenovirus 2 (Ad2) DNA was the first adenovirus genome to be completely sequenced; its sequence includes a total of 35,937 bp. The sequence of Ad5 DNA was completed more recently; its sequence includes a total of 35,935 bp. Portions of many other adenovirus genomes have also been sequenced. It is presently understood that the upper packaging limit for adenovirus virions is about 105% of the wild-type genome length. (See, e.g., Bett et al., *J. Virol.* 67(10):5911–21 (1993).) Thus, for Ad2 and Ad5, this would be an upper packaging limit of about 38 kb of DNA.

While some prefer to use replication-defective Ad viral vectors for fear that replication-competent vectors raise safety issues, the viral vectors of the present invention may retain their ability to express the genome packaged within (i.e., they may retain their infectivity), but they do not act as infectious agents to the extent that they cause disease in the subjects to whom they are administered for therapeutic purposes.

The Ad-derived viral vectors disclosed herein may be used to target and deliver genes into specific cells by incorporating the attachment sequence for other receptors (such as FGF) onto the fiber protein by recombinant DNA techniques or by immunological means, thus producing chimeric molecules or conjugates. This should result in the ability to target and deliver genes into a wide range of cell types with the advantage of evading recognition by the host's immune system. The within-disclosed targeting and delivery systems are also much more efficient at targeting and delivery than are viral vectors utilizing their native tropism, as will be further illustrated below. Thus, the within-disclosed delivery systems and constructs provide for increased flexibility in gene design to enable stable integration of molecules of choice into proliferating and nonproliferating cell types.

For example, published International App. No. WO95/26412, U.S. Pat. No. 5,543,328, and Krasnykh et al. (*J. Virol.* 70:6839–46 (1996)), the disclosures of which are incorporated by reference herein, describe modifications that may be made to the adenovirus fiber protein. Such modifications are useful in altering the targeting mechanism and specificity of adenovirus and could readily be utilized in conjunction with the constructs of the present invention to target the novel viral vectors disclosed herein to different receptors and different cells. Moreover, modifications to fiber protein which alter its tropism may permit greater control over the localization of viral vectors in therapeutic applications.

Similarly, incorporation of various structural proteins into cell lines of the present invention, whether or not those proteins are modified, is also contemplated by the present invention. Thus, for example, modified penton base polypeptides such as those described in Wickham et al. (*J. Virol.* 70:6831–8 (1996)) may have therapeutic utility when used according to the within-disclosed methods.

C. Immunological Modification of Viral Tropism

One useful method of modifying viral tropism utilizes immunological constructs. In various disclosed embodiments, it is preferred to modify the virus' native tropism and to re-target the viral vector by linking it to a ligand—especially a receptor-binding, internalizing ligand. In other embodiments, it is preferable to completely ablate the native tropism of the virus and to replace it with an entirely new tropism. Any degree of modification of a virus' native tropism—from partial modification through and including complete ablation—may readily be accomplished using immunological means, as described herein.

For example, one means of immunologically modifying a viral vector is via the construction of a bispecific antibody that binds to a viral capsid protein on one "end" and binds to a targeting moiety (ligand) on the other. In this way, a viral vector may be re-targeted via the targeting ligand. If the capsid protein to which one portion of the antibody is bound happens to be the protein via which the virus typically binds and/or enters cells, then the virus' native tropism is affected as well.

Other immunological means are also available. Construction of fusion proteins—e.g., ligand-sFv fusions—is another method of immunologically modifying a viral vector. Similar to the foregoing example, the ligand portion of the fusion confers a novel tropism upon the vector, while the antibody portion links the ligand to the vector. As before, depending upon the function of the viral capsid protein to which the antibody portion binds, attachment of the antibody may also interfere with or ablate the virus' native tropism.

Further, while these methodologies are rather less efficient, one may readily generate multiple antibodies or fragments thereof—e.g. antibodies that modify or ablate the virus' native tropism, but which do not bind a ligand for retargeting purposes, and antibodies that bind a retargeting ligand and attach it to the viral capsid. One may also generate anti-idiotype antibodies for similar purposes—i.e., to link new ligands to viral vectors and/or to modify the virus' native tropism.

As one may imagine, however, when one is contemplating using the viral vectors for gene targeting and delivery purposes, the less "bulky" the construct is, the more readily it may be delivered to and into a cell. Thus, constructs using antibody fragments which function to link a targeting ligand to the viral capsid and which simultaneously modify the virus' native tropism are more ideal for use in gene therapy applications.

1. Anti-Viral Antibody Conjugated to Ligand

As discussed herein, growth factor receptor-binding ligands—particularly polypeptides reactive with an FGF receptor—are particularly useful re-targeting agents.

Although any antibody that neutralizes or blocks a virus from targeting and binding a cell using its native tropism is contemplated herein, adenoviral anti-knob antibodies and fragments thereof are described herein as exemplary. Methods of preparing and using anti-knob antibodies and immunologically active fragments thereof are further described in the Examples that follow. Similarly, methods of preparing and using antibody-ligand conjugates are also described.

Other methods of preparing anti-viral antibodies—and the antibodies so prepared—are available and are useful according to the within-disclosed methods, as well. For example, U.S. Pat. No. 5,521,291 (the disclosures of which are incorporated by reference herein) describes a method of preparing a chimeric adenovirus having a heterologous epitope exposed in the exterior domain of its hexon protein. Depending on the method used, the degree of modification of native viral tropism—which may range from no alteration all the way to complete ablation—may be adjusted as disclosed herein.

As discussed previously, adenoviral vectors possess the in vivo gene transfer characteristics consistent with the within-disclosed targeting and delivery applications that are critical to effective gene therapy. Following administration of the adenovirus vector, three distinct, sequential steps are generally understood to be required for expression of the therapeutic gene in target cells: (1) attachment of the adenovirus vector to specific receptors on the surface of the target cell; (2) internalization of the virus; and (3) transfer of the gene to the nucleus where it can be expressed. Thus, any attempt to modify the tropism of an adenovirus vector preferably preserves the vector's ability to perform these three functions efficiently. An understanding of the adenovirus entry pathway should also facilitate attempts to modify the tropism of adenoviral vectors to permit the targeting of specific cell types.

For example, if the therapeutic goal is the modification of Ad tropism for tumor cell-specific targeting, two linked requirements are involved. First, in order to restrict gene transfer exclusively to tumor targets ablation of endogenous viral tropism is preferably achieved. Second, a new binding specificity must be introduced into the adenoviral fiber protein to allow recognition of cell surface markers characterizing neoplastic cells. Ablation of endogenous adenoviral tropism with a neutralizing anti-knob monoclonal antibody (Mab), thereby allowing the introduction of novel tropism by conjugating a cell-specific ligand to this Mab, is further discussed in Example 1 below.

2. Bi-specific Antibodies a. Background

In addition to the foregoing methodologies, it is also possible to ablate endogenous adenoviral tropism by generating a bi-specific antibody that recognizes an Ad capsid protein (e.g. knob protein) as well as the target cell-specific receptor. Polypeptides reactive with an FGF receptor are exemplary targeting ligands which are useful in this regard, as discussed in greater detail below.

Our previous work with fused cDNAs encoding FGF2 and cytotoxins established that FGF2 can serve as a vehicle to introduce DNA into cells with specificity. Based on those studies, FGF2-anti-knob Fab complexes have now been exploited for their ability to specifically target the within-disclosed adenoviral vectors to FGF receptor-bearing cells (see the Examples below).

Recombinant adenoviral vectors have the ability to efficiently transfer genes to a wide range of cell types in vitro and in vivo. Because of this, adenoviral vectors have been used in a number of different gene therapy approaches. However, adenovirus lacks the ability to accomplish cell-specific targeted gene delivery because the tropism of the parent adenovirus is quite broad, permitting widespread transduction of various end organs after systemic in vivo delivery. This broad tropism is based upon the fact that the cellular binding receptor for adenovirus is ubiquitously expressed. It is this property of the adenovirus which undermines the potential utility of adenoviral vectors as a candidate system for accomplishing the specific transduction of disseminated tumor cells. The lack of tumor-specific targeting of adenoviral vectors would allow ectopic expression of the delivered anti-cancer gene construct. Thus, despite the capacity of the adenoviral vector to accomplish high efficiency in vivo gene delivery via the vascular route, a means must be developed to redirect its tropism specifically to tumor targets. This will require both the ablation of the endogenous viral tropism and the introduction of novel tropism.

Based on the above considerations, we hypothesize that modifications of adenoviral tropism can accomplish tumor cell-specific transduction.

A number of studies have shown that retroviral cell-binding activity or tropism can be altered by modifications of the viral envelope glycoprotein which interacts with specific receptors on the cell surface. One approach has involved the construction of "pseudotypes," in which the retroviral genome is coated by the envelope protein of another virus (see, e.g., Weiss et al., Virology 76: 808–25 (1977)). The host range of the pseudotyped particle is thus dictated by the virus providing the envelope protein.

b. Construction of the Bifunctional scFv-FGF2 Fusion Protein The neutralizing anti-knob mAb, 1D6.14, was generated as described by Douglas et al . (Id. (1996)). The procedure may be described essentially as follows. Fab fragments of the mAb are also prepared for use in various constructs, as described herein. In addition to its use in the construction of fusion proteins, the mAb and fragments thereof are used to prepare FGF-Fab constructs as well (see Example 1, Section A.4 below).

To develop a neutralizing anti-knob mAb, hybridomas were generated by standard techniques after immunization of mice with intact Ad5 followed by two rounds of immunization with purified recombinant Ad5 knob. BABL/c mice were immunized with Ad5, followed by two rounds of immunization with recombinant Ad5 knob, a gift from R. D. Gerard (Univ. of Texas). (Also see Henry et al., *J. Virol.* 68:5239–5246 (1994).) Sensitized lymphocytes were fused with P3-X63-Ag8.653 cells. The reactivity of the hybridoma supernatants with trimeric Ad5 knob was determined in an ELISA. The ability of the hybridoma supernatants to neutralize Ad5 infection was assayed by endpoint CPE.

On the basis of its high affinity binding to recombinant Ad5 knob and its ability to neutralize Ad5 infection of HeLa cells, one clone, designated 1D6.14, was chosen for further study. The selected mAb was purified from ascites fluid by affinity chromatography using an immobilized protein A column.

Fab fragments were prepared and purified after digestion of intact 1D6.14 with papain. Both the parent antibody and the Fab fragment were capable of neutralizing adenovirus infection in a dose-dependent manner. (Douglas et al., Id. (1996)).

To generate the single chain ScFv, mRNA is isolated from the hybridoma and the ScFv was generated by splice site overlap extension PCR using standard techniques (Miller, R. et al, manuscript in preparation). This anti-knob scFv 01D6 will be employed to generate the bispecific retargeting fusion protein. This is accomplished by genetic insertion of the FGF2 ligand by PCR based cloning into the 01D6 pET25 *E. coli* expression vector. Convenient restriction sites, Nco and Nhe 1, were added to the 5' and 3' respectively for ease of cloning.

The amplified heavy and light chain product was cloned into the pET25 expression vector (Novagen, Milwaukee, Wis.). The expression vector, pET25, contains the promoter for T7 RNA polymerase, lac operator, pelB leader sequence, the Nco 1 restriction site in frame with pelB, the HSVTag sequence and a His Tag sequence. The FGF2 is expressed as both N-terminal and C-terminal fusion protein.

In addition, flexible linkers may be added between the scFv and FGF2 to help favor proper protein folding. One strategy to clone the FGF2 downstream of the scFv is described below. To clone the ScFv-FGF2 fusion protein, the stop codon is removed in the ScFv and human FGF2 is cloned downstream and in-frame with the ScFv. Oligos that may be used to remove the stop codon and add a restriction site in the ScFv include (5'-3'):

A1 (sense): ATATAGAATTCTGTGACTACTGAGGA-CACAGCCAC (SEQ ID NO: 1) and
A2(antisense): ATATACATATGTTTTTTCAGCTC-CAGCTTGGTCCC (SEQ ID NO: 2).

PCR amplification using these primers results in a 465 bp fragment. The PCR product has Eco R1 and Nde 1 sites a the 5' and 3' ends. The amplified fragment is preferably digested with Eco R1 and Nde 1, isolated by gel electrophoresis and purified using GENECLEAN (Bio 101, Vista, Calif.). FGF2 is obtained by digestion with restriction enzymes Nde 1 and Bam H1 from the pET 11a FGF2 expression vector (previously generated at PRIZM, San Diego, Calif.).

The remaining section of the ScFv is isolated by digestion of the pET25 ScFv with Nco 1 and Eco R1. The digested fragment is isolated by agarose gel and purified using GENECLEAN. The purified fragments are ligated together with Nco 1 Bam H1 digested pET25 in a 4-way ligation. The ligation may be transformed in to Novablue (Novagen) and clones evaluated for insertion of the fragments and further analyzed for correct restriction map. Glycerol stocks of clones with the correct restriction map are also preferably generated. DNA is purified and sequenced for verification.

c. Expression, Purification and Evaluation of ScFv-FGF2 Fusion Protein

Competent bacterial cells, BL21(DE3), are transformed with the pET25 pelB ScFv-FGF2 and pET25 pelB ScFv constructs. For expression, the plasmid transformed host cells are grown at 25–30° C. to an OD600 of 0.7 and induced with IPTG. The culture is harvested 3–4 hours after induction. The suspension is centrifuged; the supernatant clarified and assayed for either ScFv-FGF2 or ScFv protein by ELISA. The ScFv and ScFv-FGF2 fusion protein can be recognized by antiserum to both the heavy and light chains as well as to FGF2. A sample of the pellet and the supernatant is analyzed by SDS-PAGE and Western analysis using antibodies to FGF2 and heavy and light chains to determine the percentage of fusion protein within each fraction. If the fusion protein fractionates to the pellet then a refolding method such as lysis in 6 M guanidine solution and gradual dialysis into non-denaturing buffer is attempted. Alternatively, the periplasmic proteins can be isolated by osmotic shock and assayed for fusion protein. Purification is accomplished by either heparin chromatography or via the His Tag at the N-terminus of the fusion protein using metal chelate resin affinity chromatography. The purified fusion protein is tested for binding activity by ELISA using either FGF2 antibody coated plates or heavy and light chain antibody coated plates and detected with alkaline phosphatase. We have initially designed this construct for expression in *E. coli*. However, if expression of the ScFv-FGF2 fusion protein is extremely low in bacteria, then the fusion protein can easily by excised with restriction enzymes and ligated into a mammalian expression vector using the Vh leader sequence.

To be useful in retargeting adenovirus, the recombinant fusion protein must bind both the adenovirus knob as well as the cognate receptor. Thus these proteins are analyzed for their knob binding capacity in an ELISA. To validate that they bind knob in its native trimeric form, each protein is used to probe boiled and unboiled recombinant Ad5 knob in an immunoblot. Finally, a neutralizing assay is performed using AdCMVLuc. To test the functionality of the receptor binding domain, binding and internalization assays are performed on receptor positive cells. The purified ScFv is tested for receptor binding in endothelial cells as outlined in the preliminary results. In addition, binding and internalization studies are completed for the fusion protein. This is done by incubating receptor positive cells with [$^{125}$I] radiolabeled scFv-FGF2 fusion protein at 4° C. to prevent internalization. After removal of unbound protein, the amount of radioactivity in released and cell-associated fractions is determined in a scintillation counter. Binding specificity is determined by including unlabeled fusion protein as a competitor. Internalization of the fusion proteins is determined by preincubating receptor positive cells with labelled fusion protein at 4° C., washing cells to remove unbound labelled protein, warming to 37° C. for various time intervals to allow receptor internalization. Following 2M salt extraction to remove surface bound radiolabeled protein, cells are lysed and radioactivity is determined in the cell lysate. This analysis will determine the capacity of the recombinant bispecific fusion protein to bind Ad5 knob and FGF receptors in the context of a fusion protein, as well as ablate endogenous adenovirus tropism. These molecules are then evaluated for their ability to target adenoviral infection via the FGF receptor as described above.

D. Genetic or Chemical Modification of Viral Protein

Viral particles—e.g., an adenovirus protein—may alternatively be modified at the molecular level. Thus, for example, a nucleotide sequence encoding a ligand molecule may be operatively linked for expression to a viral nucleotide sequence—particularly to a sequence encoding a structural protein.

Thus, one may construct fusion proteins and other modifications of viral proteins. For example, the fiber protein of adenovirus may be modified via attachment of a heterologous nucleotide sequence to the C-terminus of the gene encoding adenoviral fiber protein. Alternatively, one or more heterologous sequences may be inserted at an internal site— i.e., within the viral fiber protein sequence.

Various methods of preparing such fusions are available in the art and are contemplated by the present invention. For example, U.S. Pat. No. 5,543,328, the disclosures of which are incorporated by reference herein, recites a method for removing all or a part of adenovirus fiber protein and replacing the removed portion with a ligand that is specific for a particular cellular receptor.

Similarly, Michael et al. proposed the addition of a short peptide ligand to Ad fiber protein via placing a sequence encoding the terminal decapeptide of gastrin releasing peptide (GRP) at the 3' end of the coding sequence of the Ad5 fiber gene. (See *Gene Therapy* 2:660–668 (1995), incorporated by reference herein.) Wickham et al. attached a heparin-binding domain to the Ad5 fiber protein and observed that the Ad vector displayed a new tropism. (See *Nature Biotech.* 14:1570–1573 (1996), incorporated by reference herein.) Although the aforementioned constructs may be useful as disclosed herein, none of them produced the unexpected, dramatic increases in targeting efficiency and nuclear trafficking obtained with the constructs of the present invention.

Finally, it should also be appreciated that viral proteins may be modified via means that are not precisely "immunologic" or "genetic." Modification of viral proteins via means other than those exemplified herein is fully within the scope of the present invention. For example, useful reprogrammed vectors of the present invention may undergo chemical alteration of their native tropism, e.g., via chemical inactivation of the virus, and they may subsequently be "reactivated" by another molecule or process designed to retarget the viral vector.

Thus, heat inactivation is one method contemplated within the scope of chemical alterations which may be made to viral vectors of the present invention. Chemical alteration of the molecular moiety (e.g. fiber protein) in a manner that disrupts of ablates the vector's endogenous tropism is also contemplated herein. Methods of altering viral proteins via chemical means are known to those of skill in the art and may readily be ascertained in the relevant literature.

E. Ligands

As noted above, the present invention provides a variety of methods of "reprogramming" the tropism of a virus (or viral vector), including methods utilizing ligands such as FGF proteins, polypeptides, analogs or mimics to assist in re-targeting the vector. While certain ligands are described as exemplary, it will be appreciated by those of skill in the art that a wide variety of molecules may appropriately be used as ligands according to the within-disclosed methodologies. The following lists—while not exhaustive—will provide one with a better understanding of the variety of ligands available for use to specifically target preselected cells and to direct the vector, conjugate or complex with which the ligand is associated into the cell—and ideally, into the nucleus.

1. Proteins That Bind to Cells and Internalize

The ligands may be produced by recombinant or other means in preparation for attachment to viral (e.g. adenoviral) proteins. The DNA sequences and methods to obtain the sequences of these ligands are well known. (see GenBank). Based on the DNA sequences, the genes may be synthesized either synthetically (for small proteins), amplified from cell genomic or cDNA, isolated from genomic or cDNA libraries and the like. Restriction sites to facilitate cloning into the viral vector may be incorporated, such as in primers for amplification.

Such molecules include, without limitation, proteins that bind cancer cells, endothelial cells, cardiovascular cells, cells in the eye and the like. Such ligands include growth factors and cytokines. Many growth factors and families of growth factors share structural and functional features and may be used in the present invention. Families of growth factors include fibroblast growth factors FGF-1 through FGF-15, and vascular endothelial growth factor (VEGF). Other growth factors, such as PDGF (platelet-derived growth factor), TGF-α (transforming growth factor), TGF-β, HB-EGF, angiotensin, bombesis, erythropoietin, stem cell factor, M-CSF, G-CSF, GM-CSF, and endoglin also bind to specific identified receptors on cell surfaces and may be used in the present invention. Cytokines, including interleukins, CSFs (colony stimulating factors), and interferons, have specific receptors, and may be used as described herein.

For example, ligands and ligand/receptor pairs include urokinase/urokinase receptor (GenBank Accession Nos. X02760/X74309); α-1,3 fucosyl transferase, α1-antitrypsin/ E-selectin (GenBank Accession Nos. M98825, D38257/ M87862); P-selectin glycoprotein ligand, P-selectin ligand/ P-selectin (GenBank Accession Nos. U25955, U02297/

L23088), VCAM1/VLA-4 (GenBank Accession Nos. X53051/X16983); E9 antigen (Blann et al., *Atherosclerosis* 120:221, 1996)/TGFβ receptor; Fibronectin (GenBank Accession No. X02761); type I α1-collagen (GenBank Accession No. Z74615), type I β2-collagen (GenBank Accession No. Z74616), hyaluronic acid/CD44 (GenBank Accession No. M59040); CD40 ligand (GenBank Accession No. L07414)/CD40 (GenBank Accession No. M83312); ELF-3, LERTK-2 ligands (GenBank Accession Nos. L37361, U09304) for elk-i (GenBank Accession No. M25269); VE-cadherin (GenBank Accession No. X79981); ligand for catenins; ICAM-3 (GenBank Accession No. X69819) ligand for LFA-1, and von Willebrand Factor (GenBank Accession No. X04385), fibrinogen and fibronectin (GenBank Accession No. X92461) ligands for $α_vβ_3$ integrin (GenBank Accession Nos. U07375, L28832).

Other ligands include CSF-1 (GenBank Accession Nos. M11038, M37435); GM-CSF (GenBank Accession No. X03021); IFN-α (interferon) (GenBank Accession No. A02076; WO 8502862-A); IFN-γ (GenBank Accession No. A02137; WO 8502624-A); IL-1-α (interleukin 1 alpha) (GenBank Accession No. X02531, M15329); IL-1-β (interleukin 1 beta) (GenBank Accession No. X02532, M15330, M15840); IL-1 (GenBank Accession No. K02770, M54933, M38756); IL-2 (GenBank Accession No. A14844, A21785, X00695, X00200, X00201, X00202); IL-3 (GenBank Accession No. M14743, M20137); IL-4 (GenBank Accession No. M13982); IL-5 (GenBank Accession No. X04688, J03478); IL-6 (GenBank Accession No. Y00081, X04602, M54894, M38669, M14584); IL-7 (GenBank Accession No. J04156); IL-8 (GenBank Accession No. Z11686); IL-10 (GenBank Accession No. X78437, M57627); IL-11 (GenBank Accession No. M57765 M37006); IL-13 (GenBank Accession No. X69079, U10307); TNF-α (Tumor necrosis factor) (GenBank Accession No. A21522); TNF-β (GenBank Accession No. D12614); urokinase/urokinase receptor (GenBank Accession Nos. X02760/X74309); α-1,3 fucosyl transferase, α1-antitrypsin/E-selectin (GenBank Accession Nos. M98825, D38257/M87862); P-selectin glycoprotein ligand, P-selectin ligand/P-selectin (GenBank Accession Nos. U25955, U02297/L01574); VCAM1/VLA-4 integrin receptor (GenBank Accession Nos. X53051/X16983 and L12002); E9 (Blann et al., *Atherosclerosis* 120:221, 1996)/ TGFβ receptor; Fibronectin (GenBank Accession No. X02761); type $I^{α1}$ collagen (GenBank Accession No. Z74615), type I β2-collagen (GenBank Accession No. Z74616), hyaluronic acid/CD44 (GenBank Accession No. M59040); CD40 ligand (GenBank Accession No. L07414)/ CD40 (GenBank Accession No. M83312); EFL-3, LERTK-2 ligands (GenBank Accession Nos. L37361, U09304) for elk-1 (GenBank Accession No. M25269); VE-cadherin (GenBank Accession No. X79981) ligand for catenins; ICAM-3 (GenBank Accession No. X69819) ligand for LFA-1, and von Willebrand Factor (GenBank Accession No. X04385), fibrinogen and fibronectin (GenBank Accession No. X92461 ligands for $α_vβ_3$ integrin (GenBank Accession Nos. U07375, L28832) and GP30 ligand (S68256) for erbB2.

Still other ligands include PDGF (GenBank Accession No. X03795, X02811), angiotensin (GenBank Accession No. K02215), and all RGD-containing peptides and proteins, such as ICAM-1 (GenBank Accession No. X06990) and VCAM-1 (GenBank Accession No. X53051) that bind to integrin receptors. Other ligands include TNFα (GenBank Accession No. A21522, X01394), IFN-γ (GenBank Accession No. A11033, A1034), IGF-I (GenBank Accession No. A29117, X56773, S61841, X56774, S61860), IGF-II (GenBank Accession No. A00738, X06159, Y00693), atrial naturietic peptide (GenBank Accession No. X54669), endothelin-1 (GenBank Accession No. Y00749), coagulation factor Xa (GenBank Accession No. L00395, L00396, L29433, N00045, M14327), TGF-β1 (GenBank Accession No. A23751), IL-1α (GenBank Accession No. X03833), IL-1β (GenBank Accession No. M15330), and endoglin (GenBank Accession No. X72012).

a. Growth Factors

1) Fibroblast Growth Factors

One family of growth factors that may be used within the context of the present invention is the fibroblast growth factor (FGF) family. The members of the FGF family have a high degree of amino acid sequence similarities and common physical and biological properties, including the ability to bind to one or more FGF receptors.

This family of proteins includes FGFs designated FGF-1 (acidic FGF (aFGF)), FGF-2 (basic FGF (bFGF)), FGF-3 (int-2) (see, e.g., Moore et al., *EMBO J.* 5:919–924, 1986), FGF-4 (hst-1/K-FGF) (see, e.g., Sakamoto et al., *Proc. Natl Acad. Sci. USA* 86:1836–1840, 1986; U.S. Pat. No. 5,126, 323), FGF-5 (see, e.g., U.S. Pat. No. 5,155,217), FGF-6 (hst-2) (see, e.g., published European Application EP 0 488 196 A2; Uda et al., *Oncogene* 7:303–309, 1992), FGF-7 (keratinocyte growth factor) (KGF) (see, e.g., Finch et al., *Science* 245:752–755, 1985; Rubin et al., *Proc. Natl. Acad. Sci. USA* 86:802–806, 1989; and International Application WO 90/08771), FGF-8 (see, e.g., Tanaka et al., *Proc Natl. Acad. Sci. USA* 89:8528–8532, 1992); FGF-9 (see, Miyamoto et al., *Mol. Cell. Biol.* 13:4251–4259, 1993); FGF-11 (WO 96/39507); FGF-13 (WO 96/39508); FGF-14 (WO 96/39506); FGF-15 (WO 96/39509). Other polypeptides that are reactive with an FGF receptor, that is any polypeptide that specifically interacts with an FGF receptor, preferably the high affinity FGF receptor, and is transported by way of endosomes into the cell by virtue of its interaction with the FGF receptor are suitable within the present invention.

DNA encoding FGF peptides and/or the amino acid sequences of FGFs are well known. For example, DNA encoding human FGF-1 (Jaye et al., *Science* 233:541–545, 1986; U.S. Pat. No. 5,223,483), bovine FGF-2 (Abraham et al., *Science* 233:545–548, 1986; Esch et al., *Proc. Natl. Acad. Sci. USA* 82:6507–6511, 1985; and U.S. Pat. No. 4,956,455), human FGF-2 (Abraham et al., *EMBO J.* 5:2523–2528, 1986; U.S. Pat. No. 4,994,559; U.S. Pat. No. 5,155,214; EP 470,183B; and Abraham et al., *Quant. Biol.* 51:657–668, 1986) rat FGF-2 (see Shimasaki et al., *Biochem. Biophys. Res. Comm.*, 1988, and Kurokawa et al., *Nucleic Acids Res.* 16:5201, 1988), FGF-3, FGF-6, FGF-7 and FGF-9 are known (see also U.S. Pat. No. 5,155,214; U.S. Pat. No. 4,956,455; U.S. Pat. No. 5,026,839; U.S. Pat. No. 4,994,559, EP 0,488,196 A2, EMBL or GenBank databases, and references discussed herein).

FGFs exhibit a mitogenic effect on a wide variety of mesenchymal, endocrine and neural cells and are also important in differentiation and development. FGFs stimulate collateral vascularization and angiogenesis, which makes them useful as "payloads" as well, as discussed in a subsequent section. In some instances, FGF-induced mitogenic stimulation may be detrimental. For example, cell proliferation and angiogenesis are an integral aspect of tumor growth. Members of the FGF family, including FGF-2, are thought to play a pathophysiological role, for example, in tumor development, rheumatoid arthritis, proliferative diabetic retinopathies and other complications of diabetes. To reduce or eliminate mitogenesis, muteins of FGF may be used and constructed as described below. Such muteins retain the ability to bind to high and low affinity receptors.

Polypeptides reactive with FGF receptors are also useful in targeting not only tumors and malignant cells in particular, but hyperproliferating cells in general. Thus, to name one example, FGF-7, which is also known as KGF, can be used to target the vectors and constructs of the present invention to hyperproliferating SMCs and a variety of epithelial cells. KGF is also particularly useful in targeting hepatocytes and type II pneumocytes of the lung.

The effects of FGFs are mediated by high affinity receptor tyrosine kinases present on the cell surface of FGF-responsive cells (see, e.g., PCT WO 91/00916, WO 90/05522, PCT WO 92/12948; Imamura et al., *Biochem. Biophys. Res. Comm.* 155:583–590, 1988; Huang et al., *J. Biol. Chem.* 261:9568–9571, 1986; Partanen et al., *EMBO J.* 10:1347, 1991; and Moscatelli, *J. Cell. Physiol.* 131:123, 1987). Low affinity receptors also appear to play a role in mediating FGF activities. The high affinity receptor proteins are single chain polypeptides with molecular weights ranging from 110 to 150 kD, depending on cell type that constitute a family of structurally related FGF receptors. Four FGF receptor genes have been identified, three of which generate multiple mRNA transcripts via alternative splicing of the primary transcript. Some receptor specificity has been uncovered. For example, FGF-9 binds specifically to FGFR3, which is expressed in epithelial cells and cartilage rib bone, epithelial cells exclusively express FGFR3IIIb, while mesenchymal cells express FGFR3IIIb and FGFR3IIIc.

In addition to their use as ligands, various forms of FGFs may be used as "payloads" for gene therapy applications. While FGF cDNA or genomic FGF DNA is often preferred for such therapeutic use, other forms may efficaciously be used as well. The therapeutic aspects of FGF DNA use are described in greater detail in Section F below.

2) Vascular Endothelial Growth Factors

Vascular endothelial growth factors (VEGFs) can directly stimulate endothelial cell growth, enhance angiogenesis, enhance glucose transport, and cause a rapid and reversible increase in blood vessel permeability. VEGF is expressed during normal development and in certain normal adult organs. Purified VEGF is a basic, heparin-binding, homodimeric glycoprotein that is heat-stable, acid-stable and may be inactivated by reducing agents. Polypeptides reactive with a VEGF receptor are thus contemplated for use as ligands in the context of the present invention.

The members of this family have been referred to variously as vascular endothelial growth factor (VEGF), vascular permeability factor (VPF) and vasculotropin (see, e.g., Plouet et al., *EMBO J.* 8:3801–3806, 1989). Herein, they are collectively referred to as VEGF.

DNA sequences encoding VEGF and methods to isolate these sequences may be found primarily in U.S. Pat. No. 5,240,848, U.S. Pat. No. 5,332,671, U.S. Pat. No. 5,219,739, U.S. Pat. No. 5,194,596, and Houch et al., *Mol. Endocrin.* 5:180, 1991.

DNA encoding VEGF refers to DNA that encodes any such member of the VEGF family, including VEGF isoforms that result from alternative splicing of RNA transcribed from a VEGF gene (see, e.g., International PCT Application No. WO 90/13649, which is based on U.S. applications Ser. Nos. 07/351,361, now U.S. Pat. No. 5,006,434, 07/369,424, abandoned Mar. 17, 1992, 07/389,722, now U.S. Pat. No. 5,332,671, to GENENTECH, INC., and any U.S. Patent based U.S. applications Ser. Nos. 07/351,361, now U.S. Pat. Nos. 5,006,434, 07/369,424, abandoned Mar. 17, 1992, 07/389,722, now U.S. Pat. No. 5,332,671; European Patent Applications EP 0 506 477 A1 and EP 0 476 983 A1 to Merck & Co.; Houck et al. (1991) *Mol. Endo.* 5:1806–1814). It is also understood that substitutions in codons by virtue of the degeneracy of the genetic code are encompassed by DNA encoding such VEGF. DNA encoding the VEGF polypeptide may be obtained from any source known to those of skill in the art; it may be isolated using standard cloning methods, synthesized or obtained from commercial sources, prepared as described in any of the above noted patents and publications.

Four molecular species of VEGF result from alternative splicing of mRNA and contain 121, 165, 189 and 206 amino acids. The predominant isoform secreted by a variety of normal and transformed cells is $VEGF_{165}$. The secreted isoforms, $VEGF_{121}$ and $VEGF_{165}$ are preferred VEGF proteins. The longer isoforms, $VEGF_{189}$ and $VEGF_{206}$, bind to the extracellular matrix and need to be released by an agent, such as suramin, heparin or heparinase, or plasmin. $VEGF_{121}$ is a weakly acidic polypeptide that lacks the heparin binding domain and, consequently, does not bind to heparin. Other preferred VEGF proteins contain various combinations of VEGF exons, such that the protein still binds VEGF receptor and is internalized.

It is not necessary that a VEGF protein used as a ligand in the context of this invention either retain any of its in vivo biological activities, such as stimulating endothelial cell growth, or bind heparin other than bind a VEGF receptor on a cell and be internalized. However, it may be desirable in certain contexts for VEGF to manifest certain of its biological activities. For example, if VEGF is used as a carrier for DNA encoding a molecule useful in wound healing, it would be desirable that VEGF exhibit vessel permeability activity and promotion of fibroblast migration and angiogenesis. If VEGF is used as payload, as described further in Section F below, retention of such abilities is also desirable. It will be apparent from the teachings provided within the subject application which of the activities of VEGF are desirable to maintain.

Quiescent and proliferating endothelial cells bind VEGF with high affinity, and endothelial cell responses to VEGF appear to be mediated by high affinity cell surface receptors (see, e.g., PCT Application WO 92/14748, U.S. application Ser. No. 08/657,236, de Vries et al., *Science* 255:989–91, 1992; Terman et al., *Biochem. Biophys. Res. Commun.* 187:1579–1586, 1992; Kendall et al., *Proc. Natl. Acad. Sci. USA* 90:10705–10709, 1993; and Peters et al., *Proc. Natl. Acad. Sci. USA* 90:8915–8919, 1993). Two tyrosine kinases have been identified as VEGF receptors. The first, known as fms-like tyrosine kinase or FLT, is a receptor tyrosine kinase that is specific for VEGF. In adult and embryonic tissues, expression of FLT mRNA is localized to the endothelium and to populations of cells that give rise to endothelium. The second receptor, KDR (human kinase insert domain-containing receptor), and its mouse homologue FLK-1, are closely related to FLT. The KDR/FLK-1 receptor is expressed in endothelium during the fetal growth stage, during earlier stages of embryonic development, and in adult tissues. In addition, messenger RNA encoding FLT and KDR have been identified in tumor blood vessels and specifically by endothelial cells of blood vessels supplying glioblastomas. Similarly, FLT and KDR mRNAs are upregulated in tumor blood vessels in invasive human colon adenocarcinoma, but not in the blood vessels of adjacent normal tissues.

3) Heparin-binding epidermal growth factors

HBEGF interacts with the same high affinity receptors as EGF on bovine aortic smooth muscle cells and human A431 epidermoid carcinoma cells (Higashiyama, *Science* 251:936–939, 1991). HBEGFs exhibit a mitogenic effect on a wide variety of cells including BALB/c 3T3 fibroblast cells and smooth muscle cells, but are not mitogenic for endothelial cells (Higashiyama et al., *Science* 251:936–939, 1991). However, HBEGF has a stimulatory effect on collateral vascularization and angiogenesis. Members of the HBEGF family are thought to play a pathophysiological role, for example, in a variety of tumors, such as bladder carcinomas, breast tumors and non-small cell lung tumors. Thus, these cell types are likely candidates for delivery of therapeutic gene products.

HBEGF isolated from U-937 cells is heterogeneous in structure and contains at least 86 amino acids and two sites of O-linked glycosyl groups (Higashiyama et al., *J. Biol. Chem.* 267:6205–6212, 1992). The carboxyl-terminal half of the secreted HBEGF shares approximately 35% sequence identity with human EGF, including six cysteines spaced in the pattern characteristic of members of the EGF protein family. In contrast, the amino-terminal portion of the mature factor is characterized by stretches of hydrophilic residues and has no structural equivalent in EGF. Site-directed mutagenesis of HBEGF and studies with peptide fragments have indicated that the heparin-binding sequences of HBEGF reside primarily in a 21 amino acid stretch upstream of and slightly overlapping the EGF-like domain.

DNA encoding an HBEGF peptide or polypeptide refers to any DNA fragment encoding an HBEGF, HBEGF fragment or HBEGF mutein that binds an EGF receptor and internalizes. Such DNA sequences encoding HBEGF fragments are available from publicly accessible databases, such as: EMBL, GenBank (Accession Nos. M93012 (monkey) and M60278 (human)); the plasmid pMTN-HBEGF (ATCC #40900) and pAX-HBEGF (ATCC #40899) (described in PCT Application WO/92/06705); and Abraham et al., *Biochem. Biophys. Res. Comm.* 190:125–133, 1993).

The effects of HBEGFs are mediated by EGF receptor tyrosine kinases expressed on cell surfaces of HBEGF-responsive cells (see, e.g., U.S. Pat. Nos. 5,183,884 and 5,218,090; and Ullrich et al., *Nature* 309:4113–425, 1984). The EGF receptor proteins, which are single chain polypeptides with molecular weights 170 kD, constitute a family of structurally related EGF receptors. Cells known to express the EGF receptors include smooth muscle cells, fibroblasts, keratinocytes, and numerous human cancer cell lines, such as the: A431 (epidermoid); KB3-1 (epidermoid); COLO 205 (colon); CRL 1739 (gastric); HEP G2 (hepatoma); LNCAP (prostate); MCF-7 (breast); MDA-MB-468 (breast); NCI 417D (lung); MG63 (osteosarcoma); U-251 (glioblastoma); D-54MB (glioma); and SW-13 (adrenal).

For the purposes of this invention, if HBEGFs (including fragments or derivatives thereof) are used as ligands, HBEGF need only bind a specific EGF receptor and be internalized. Members of the HBEGF family are those that have sufficient nucleotide identity to hybridize under normal stringency conditions (typically greater than 75% nucleotide identity). Subfragments or subportions of a full-length HBEGF may also be desirable. One skilled in the art may find from the teachings provided within that certain biological activities are more or less desirable, depending upon the application.

2. Antibodies to Receptors That Internalize

Antibodies to molecules expressed on the surface of cells are useful within the context of the present invention as long as the antibody is internalized following binding. Such antibodies include, but are not limited to, antibodies to FGF receptors, VEGF receptors, urokinase receptor, E- and P-selectins, VCAM-1, PDGF receptor, TGF receptor, endosialin, alpha$_v$ beta$_3$ integrin, LFA-1, E9 antigen, CD40, cadherins, and elk-1. Antibodies that are specific to cell surface molecules expressed by cells are readily generated as monoclonals or polyclonal antisera. Many such antibodies are available (e.g., from American Type Culture Collection, Rockville, Md.). Alternatively, antibodies to ligands that bind/internalize may also be used. In such a strategy, the viral particles will have antibody on their surface, which will then be complexed to the ligand (see further discussion below).

Within the context of the present invention, antibodies are understood to include monoclonal antibodies, polyclonal antibodies, anti-idiotypic antibodies, antibody fragments (e.g., Fab, and F(ab')$_2$, F$_v$ variable regions, or complementarity determining regions). Antibodies are generally accepted as specific against indolicidin analogues if they bind with a K$_d$ of greater than or equal to $10^{-7}$M, preferably greater than of equal to $10^{-8}$M. The affinity of a monoclonal antibody or binding partner can be readily determined by one of ordinary skill in the art (see Scatchard, *Ann. N.Y. Acad. Sci.* 51:660–672, 1949). Once suitable antibodies have been obtained, they may be isolated or purified by many techniques well known to those of ordinary skill in the art.

For example, one such internalizing, receptor-binding antibody is identified herein as the "11A8" antibody. The 11A8 antibody is a monoclonal antibody which recognizes the high affinity fibroblast growth factor receptor (FGFR1). The following general procedure, which may be used to generate other useful antibodies which bind to receptors and internalize, was employed to generate 11A8.

Mice were immunized with intact SK-HEP1 cells, derived from a liver adenocarcinoma, which express high affinity FGF receptors. Hybridomas were screened using the extracellular domain of FGFR1. One resulting monoclonal, 11A8, recognizes the high affinity FGF receptor by Western blotting, immunoprecipitates FGF receptor from cell extracts and recognizes the native receptor on the cell surface. Immunofluorescence studies show that 11A8 reacts with a membrane-associated protein on the surface of SK-Hep-1 and SK-Mel-28 (human melanoma) cells, which also express numerous FGF receptors.

When 11A8 is conjugated to the ribosome inactivating protein saporin, it becomes a potent cytocidal agent that targets cells that express high affinity FGF receptors. The resulting immunotoxin, 11A8-saporin, inhibits solid tumor growth of a human melanoma xenografted into nude mice. When 11A8 is conjugated to nucleic acid or to the viral vectors of the present invention, it is able to target cells expressing its cognate receptor and to deliver therapeutic gene sequences to those cells, as it is able to internalize as well.

Commercially available antibodies to cell surface molecules may also be used as taught herein if they internalize. One assay that is used is a test for an antibody to kill cells. Briefly, the test hybridoma antibody and test cells are incubated. Unbound antibody is washed away. A second stage antibody, such as an anti-IgG antibody, conjugated to saporin is incubated with the test cells. Cell killing is assessed by any known assay, including trypan blue exclusion, MTT uptake, fluorescein diacetate staining, and the like.

Other techniques may also be utilized to construct monoclonal antibodies (see Huse et al., *Science* 246:1275–1281, 1989; Sastry et al., *Proc. Natl. Acad. Sci. USA* 86:5728–5732, 1989; Alting-Mees et al., *Strategies in Molecular Biology* 3:1–9, 1990; describing recombinant techniques). These techniques include cloning heavy and light chain immunoglobulin cDNA in suitable vectors, such as λImmunoZap(H) and λ ImmunoZap(L). These recombinants may be screened individually or co-expressed to form Fab fragments or antibodies (see Huse et al., supra; Sastry et al., supra). Positive plaques may subsequently be converted to a non-lytic plasmid that allows high level expression of monoclonal antibody fragments from *E. coli.*

Similarly, portions or fragments, such as Fab and Fv fragments, of antibodies may also be constructed utilizing conventional enzymatic digestion or recombinant DNA techniques to yield isolated variable regions of an antibody. Within one embodiment, the genes which encode the variable region from a hybridoma producing a monoclonal antibody of interest are amplified using nucleotide primers for the variable region.

In addition, techniques may be utilized to change a "murine" antibody to a "human" antibody, without altering the binding specificity of the antibody. Some examples of the specific receptors against which antibodies may be generated are set forth below.

a. Antibodies to Molecules on Tumor Cells

Antibodies to molecules expressed on the surface of tumor cells are useful within the context of the present invention as long as the antibody is internalized following binding. Such antibodies include but are not limited to antibodies to FGF receptors, VEGF receptors, and the receptors set forth above.

Antibodies may be polyclonal or monoclonal. Commercially available antibodies to some tumor cell surface molecules may be used if they internalize. One assay that is used is a test for an antibody to kill tumor cells. Briefly, the test hybridoma antibody and tumor cells are incubated. Unbound antibody is washed away. A second stage antibody, such as an anti-IgG antibody, conjugated to saporin is incubated with the tumor cells. Cell killing is assessed by any known assay, including trypan blue exclusion, MTT uptake, fluorescein diacetate staining, and the like.

b. Antibodies to Molecules on Smooth Muscle Cells

Antibodies to molecules expressed on the surface of smooth muscle cells are useful within the context of the present invention as long as the antibody is internalized following binding. Such antibodies include but are not limited to antibodies to FGF receptors, EGF receptors, TNFα receptor, IFN-γ receptor, TGF receptor, endothelin 1 receptor.

Antibodies may be polyclonal or monoclonal. Commercially available antibodies to some smooth muscle cell surface molecules may be used if they internalize. Briefly, antibodies are raised by immunization of mice, rats, rabbits or other animals with normal, tumorigenic, or cultured smooth muscle cells. Various immunization protocols may be found in for example, Harlow and Lane (*Antibodies: A Laboratory Manual*, Cold Spring Harbor Laboratory, 1988) and Coligan et al. (*Current Protocols in Immunology*, Greene Publishing, 1995). Following immunization, spleen or lymph nodes are collected for generating hybridomas or serum is collected for polyclonal antibodies. Hybridomas are preferred. Cells from spleen or lymph node are fused to a myeloma cell line (see, Harlow and Lane, supra; and Coligan et al., supra; for protocols). Antibody-secreting hybridomas are grown, and the antibodies are tested for binding to smooth muscle cells by ELISA, section staining, flow cytometry, confocal microscopy and the like. When the antibodies are to be used on hyperproliferating smooth muscle cells, preferably the antibody does not bind or binds much less to quiescent smooth muscle cells. Positive antibodies are further tested for internalization. One assay that is used is a test for an antibody to kill smooth muscle cells. Briefly, the test hybridoma antibody and smooth muscle cells are incubated. Unbound antibody is washed away. A second stage antibody, such as an anti-IgG antibody, conjugated to saporin is incubated with the smooth muscle cells. Cell killing is assessed by any known assay, including trypan blue exclusion, MTT uptake, fluorescein diacetate staining, and the like.

c. Antibodies to Molecules on Endothelial and Smooth Muscle Cells

Antibodies to molecules expressed on the surface of endothelial and smooth muscle cells are useful within the context of the present invention as long as the antibody is internalized following binding. Such antibodies include but are not limited to antibodies to FGF receptors, VEGF receptors, urokinase receptor, E- and P-selectins, VCAM-1, PDGF receptor, TGF receptor, endosialin, alpha$_v$, beta$_3$ integrin, LFA-1, E9 antigen, CD40, cadherins, and elk-1.

Antibodies may be polyclonal or monoclonal. Commercially available antibodies to some endothelial or smooth muscle cell surface molecules may be used if they internalize. One assay that is used is a test for an antibody to kill cells. Briefly, the test hybridoma antibody and test cells are incubated. Unbound antibody is washed away. A second stage antibody, such as an anti-IgG antibody, conjugated to saporin is incubated with the test cells. Cell killing is assessed by any known assay, including trypan blue exclusion, MTT uptake, fluorescein diacetate staining, and the like.

3. Other Ligands a. Ligands Internalized by Endothelial and Smooth Muscle Cells

As noted above, receptor-binding internalized ligands are used to deliver nucleic acids, including a therapeutic agent-encoding agent, to a cell expressing an appropriate receptor on its cell surface. Numerous molecules that bind specific receptors have been identified and are suitable for use in the present invention. In addition to ligands that target endothelial cells, ligands that target smooth muscle cells are useful in the context of this invention. Smooth muscle cells (SMC) are an essential requirement for neovessel formation, providing the contractile and structural components of capillaries, venules, veins, arterioles, and arteries. As such, targeting SMC will also affect neovascularization processes in diseased tissues. Such molecules include growth factors, cytokines, and antibodies. Many growth factors and families of growth factors share structural and functional features and may be used in the present invention. Families of growth factors include fibroblast growth factors FGF-1 through FGF-15, and vascular endothelial growth factor (VEGF). Other growth factors, such as PDGF (platelet-derived growth factor), TGF-α (transforming growth factor), TGF-β, HB-EGF, angiotensin and endoglin also bind to specific identified receptors on cell surfaces and may be used in the present invention. Antibodies that are specific to cell surface molecules expressed by endothelial cells or smooth muscle cells are readily generated as monoclonals or polyclonal antisera. Many such antibodies are available (e.g., from American Type Culture Collection, Rockville, Md.). Cytokines, including interleukins, CSFs (colony stimulating factors), and interferons, have specific receptors on endothelial cells, and may be used as described herein. These and other ligands are discussed in more detail below.

Fragments of these ligands may be used within the present invention, so long as the fragment retains the ability to bind to the appropriate cell surface molecule. Likewise, ligands with substitutions or other alterations, but which retain binding ability, may also be used. As well, a particular ligand refers to a polypeptide(s) having an amino acid sequence of the native ligand, as well as modified sequences, (e.g., having amino acid substitutions, deletions, insertions or additions compared to the native protein) as long as the ligand retains the ability to bind to its receptor on an endothelial cell and be internalized.

b. Ligands that Bind to Tumor Cells

As noted above, receptor-binding internalized ligands are used to deliver nucleic acids to a cell expressing an appropriate receptor on its cell surface. Numerous molecules that bind specific receptors on tumor cells have been identified and are suitable for use in the present invention. For example, the following table sets forth some of the better known ligands and cell surface molecules on various tumors.

| Tumor | Ligand | Receptor |
|---|---|---|
| T cell lymphomas | IL-2 | IL-2 receptor |
| B cell lymphomas | Antibody | Immunoglobulin idiotypes |
| Melanomas | FGF | MAGE; FGF receptor |
| Prostate tumors | | Prostate specific antigen-1; probasin |
| Angiogenic tumors | FGF; VEGF; PDGF | FGF receptor; VEGF receptor; PDGF receptor |
| Breast tumors | heregulin; FGF | erb B2; erb B3; erb B4; MUC-1; HSP-27; int-1; int-2 |
| Colon, lung tumors | Antibody; FGF; VEGF | CEA; FGF receptor; VEGF receptor |
| Bladder tumors | HBEGF; EGF/TGF; FGF | EGF receptor; FGF receptor |
| Pancreatic tumors | FGF | FGF receptor |
| Myeloid leukemias | FGF; CD antibodies | FGF receptor; CD molecules |
| Endometrial carcinoma; cervical carcinoma | VEGF | VEGF receptor |

In addition, other receptors, such as transferrin receptor, are preferentially expressed on most all tumor cells. Antibodies that are specific to cell surface molecules on tumors are readily generated as monoclonals or polyclonal antisera. Many such antibodies are available (e.g., from American Type Culture Collection, Rockville, Md.).

Fragments of these ligands may be used within the present invention, so long as the fragment retains the ability to bind to the appropriate cell surface molecule. Likewise, ligands with substitutions or other alterations, but which retain binding ability, may also be used. As well, a particular ligand refers to a polypeptide(s) having an amino acid sequence of the native ligand, as well as modified sequences, (e.g., having amino acid substitutions, deletions, insertions or additions compared to the native protein) as long as the ligand retains the ability to bind to its receptor on a tumor cell and be internalized.

Some of the more useful receptors according to the present invention are those that efficiently bind ligand and not only internalize it but enhance its delivery to the nucleus. Thus, ligands that specifically target such receptors are especially preferred. ligands that specifically target receptors that direct the ligand to the nucleus with high efficiency are even more preferred.

Ligands also encompass muteins that possess the ability to bind to their receptor expressing cells and be internalized. Such muteins include, but are not limited to, those produced by replacing one or more of the cysteines with serine as described herein. Typically, such muteins will have conservative amino acid changes. DNA encoding such muteins will, unless modified by replacement of degenerate codons, hybridize under conditions of at least low stringency to native DNA sequence encoding the wild-type ligand. (Exemplary methods of generating FGF muteins are described in Example 3.)

DNA encoding a ligand may be prepared synthetically based on known amino acid or DNA sequence, isolated using methods known to those of skill in the art (e.g., PCR amplification), or obtained from commercial or other sources. DNA encoding a ligand may differ from the above sequences by substitution of degenerate codons or by encoding different amino acids. Differences in amino acid sequences, such as those occurring among the homologous ligand of different species as well as among individual organisms or species, are tolerated as long as the ligand binds to its receptor. Ligands may be isolated from natural sources or made synthetically, such as by recombinant means or chemical synthesis.

Other receptor-binding ligands may be used in the present invention. Any protein, polypeptide, analogue, or fragment that binds to a cell-surface receptor and is internalized may be used. These ligands may be produced by recombinant or other means in preparation for conjugation to the nucleic acid binding domain. The DNA sequences and methods to obtain the sequences of these receptor-binding internalized ligands are well known. For example, these ligands include CSF-1 (GenBank Accession Nos. M11038, M37435; Kawasaki et al., Science 230:291–296, 1985; Wong et al., Science 235:1504–1508, 1987); GM-CSF (GenBank Accession No. X03021; Miyatake et al., EMBO J. 4:2561–2568, 1985); IFN-α (interferon) (GenBank Accession No. A02076; Patent No. WO 8502862-A, Jul. 4, 1985); IFN-γ (GenBank Accession No. A02137; Patent No. WO 8502624-A, Jun. 20, 1985); IL-1-α (interleukin 1 alpha) (GenBank Accession No. X02531, M15329; March et al., Nature 315:641–647, 1985; Nishida et al., Biochem. Biophys. Res. Commun. 143:345–352, 1987); IL-1-β (interleukin 1 beta) (GenBank Accession No. X02532, M15330, M15840; March et al., Nature 315:641–647, 1985; Nishida et al., Biochem. Biophys. Res. Commun. 143:345–352, 1987; Bensi et al., Gene 52:95–101, 1987); IL-1 (GenBank Accession No. K02770, M54933, M38756; Auron et al., Proc. Natl. Acad Sci. USA 81:7907–7911, 1984; Webb et al., Adv. Gene Technol. 22:339–340, 1985); IL-2 (GenBank Accession No. A14844, A21785, X00695, X00200, X00201, X00202; Lupker et al., Patent No. EP 0307285-A, Mar. 15, 1989; Perez et al., Patent No. EP 0416673-A, Mar. 13, 1991; Holbrook et al., Nucleic Acids Res. 12:5005–5013, 1984; Degrave et al., EMBO J. 2:2349–2353, 1983; Taniguchi et al., Nature 302:305–310, 1983); IL-3 (GenBank Accession No. M14743, M20137; Yang et al., Cell 47:3–10, 1986; Otsuka et al., J. Immunol. 140:2288–2295, 1988); IL-4 (GenBank Accession No. M13982; Yokota et al., Proc. Natl. Acad Sci. USA 83:5894–5898, 1986); IL-5 (GenBank Accession No. X04688, J03478; Azuma et al., Nucleic Acids Res. 14:9149–9158, 1986; Tanabe et al., J. Biol. Chem. 262:16580–16584, 1987; IL-6 (GenBank Accession No. Y00081, X04602, M54894, M38669, M14584; Yasukawa et al., EMBO J. 6:2939–2945, 1987; Hirano et al., Nature 324:73–76, 1986; Wong et al., Behring Inst. Mitt. 83:40–47, 1988; May et al., Proc. Natl. Acad Sci. USA 83:8957–8961, 1986); IL-7 (GenBank Accession No. J04156; Goodwin et al., Proc. Natl Acad Sci. USA 86:302–306, 1989); IL-8 (GenBank Accession No. Z11686; Kusner et al., Kidney Int. 39:1240–1248, 1991); IL-10 (GenBank Accession No. X78437, M57627; Vieira et al., Proc. Natl. Acad. Sci. USA 88:1172–1176, 1991); IL-11 (GenBank Accession No.

M57765 M37006; Paul et al., *Proc. Natl. Acad Sci. USA* 87:7512–7516, 1990); IL-13 (GenBank Accession No. X69079, U10307; Minty et al., *Nature* 362:248–250, 1993; Smirnov, *Shemyakin and Ovchinnikov Institute of Bioorganic Chemistry*, Jun. 2, 1994); TNF-α (Tumor necrosis factor) (GenBank Accession No. A21522; Patent No. GB 2246569-A1, Feb. 5, 1992); TNF-β (GenBank Accession No. D12614; Matsuyama et al., *FEBS LETTERS* 302:141–144, 1992); urokinase/urokinase receptor (GenBank Accession Nos. X02760/X74309); α-1,3 fucosyl transferase, α1-antitrypsin/E-selectin (GenBank Accession Nos. M98825, D38257/M87862); P-selectin glycoprotein ligand, P-selectin ligand/P-selectin (GenBank Accession Nos. U25955, U02297/L01574); VCAM1/VLA-4 integrin receptor (GenBank Accession Nos. X53051/X16983 and L12002); E9 (Blann et al., *Atherosclerosis* 120:221, 1996)/TGFβ receptor; Fibronectin (GenBank Accession No. X02761);type $I^{\alpha 1}$ collagen (GenBank Accession No. Z74615), type I β2-collagen (GenBank Accession No. Z74616), hyaluronic acid/CD44 (GenBank Accession No. M59040); CD40 ligand (GenBank Accession No. L07414)/CD40 (GenBank Accession No. M83312); EFL-3, LERTK-2 ligands (GenBank Accession Nos. L37361, U09304) for elk-1 (GenBank Accession No. M25269); VE-cadherin (GenBank Accession No. X79981) ligand for catenins; ICAM-3 (GenBank Accession No. X69819) ligand for LFA-1, and von Willebrand Factor (GenBank Accession No. X04385), fibrinogen and fibronectin (GenBank Accession No. X92461 ligands for $\alpha_v\beta_3$ integrin (GenBank Accession Nos. U07375, L28832) and GP30 ligand (S68256) for erbB2. DNA sequences of other suitable receptor-binding internalized ligands may be obtained from GenBank or EMBL DNA databases, reverse-synthesized from protein sequence obtained from PIR database or isolated by standard methods (Sambrook et al., supra) from cDNA or genomic libraries.

c. Other Ligands That Bind to Cells

Other receptor-binding ligands may be used in the present invention. Any protein, polypeptide, analogue, or fragment that binds to a smooth muscle cell-surface receptor and is internalized may be used. These ligands may be produced by recombinant or other means in preparation for conjugation to the nucleic acid binding domain. The DNA sequences and methods to obtain the sequences of these receptor-binding internalized ligands are well known. For example, these ligands include PDGF (GenBank Accession No. X03795, X02811), angiotensin (GenBank Accession No. K02215), and all RGD-containing peptides and proteins, such as ICAM-1 (GenBank Accession No. X06990) and VCAM-1 (GenBank Accession No. X53051) that bind to integrin receptors. Other ligands include TNFα (GenBank Accession No. A21522, X01394), IFN-γ (GenBank Accession No. A11033, A11034), IGF-I (GenBank Accession No. A29117, X56773, S61841, X56774, S61860), IGF-II (GenBank Accession No. A00738, X06159, Y00693), atrial naturietic peptide (GenBank Accession No. X54669), endothelin-1 (GenBank Accession No. Y00749), coagulation factor Xa (GenBank Accession No. L00395, L00396, L29433, N00045, M14327), TGF-β1 (GenBank Accession No. A23751), IL-1α (GenBank Accession No. X03833), IL-1β (GenBank Accession No. M15330), and endoglin (GenBank Accession No. X72012). DNA sequences of other suitable receptor-binding internalized ligands may be obtained from GenBank or EMBL DNA databases, reverse-synthesized from protein sequence obtained from PIR database or isolated by standard methods (Sambrook et al., supra) from cDNA or genomic libraries.

As noted previously, any protein, polypeptide, analogue, or fragment that binds to a cell-surface receptor and is internalized may be used. Molecules that mimic or interact with a cell surface molecule that is trafficked to the nucleus are also included within the scope of the present invention. These ligands may be produced by recombinant or other means in preparation for conjugation to the nucleic acid binding domain. The DNA sequences and methods to obtain the sequences of these receptor-binding internalized ligands are well known. For example, these ligands and ligand/receptor pairs include urokinase/urokinase receptor (GenBank Accession Nos. X02760/X74309); α-1,3 fucosyl transferase, α1-antitrypsin/E-selectin (GenBank Accession Nos. M98825, D38257/M87862); P-selectin glycoprotein ligand, P-selectin ligand/P-selectin (GenBank Accession Nos. U25955, U02297/L23088), VCAM1/VLA-4 (GenBank Accession Nos. X53051/X16983); E9 antigen (Blann et al., *Atherosclerosis* 120:221, 1996)/TGFβ receptor; Fibronectin (GenBank Accession No. X02761); type I α1-collagen (GenBank Accession No. Z74615), type I β2-collagen (GenBank Accession No. Z74616), hyaluronic acid/CD44 (GenBank Accession No. M59040); CD40 ligand (GenBank Accession No. L07414)/CD40 (GenBank Accession No. M83312); ELF-3, LERTK-2 ligands (GenBank Accession Nos. L37361, U09304) for elk-1 (GenBank Accession No. M25269); VE-cadherin (GenBank Accession No. X79981); ligand for catenins; ICAM-3 (GenBank Accession No. X69819) ligand for LFA-1, and von Willebrand Factor (GenBank Accession No. X04385), fibrinogen and fibronectin (GenBank Accession No. X92461) ligands for $\alpha_v\beta_3$ integrin (GenBank Accession Nos. U07375, L28832). DNA sequences of other suitable receptor-binding internalized ligands may be obtained from GenBank or EMBL DNA databases, reverse-synthesized from protein sequence obtained from PIR database or isolated by standard methods (Sambrook et al., supra) from cDNA or genomic libraries.

d. Peptidomimetic Ligands

Ligands or fragments thereof that bind to a cell-surface receptor and are internalized, but which are mimetics of "true" polypeptides, are also contemplated for use in the present invention. Thus, in one aspect, the invention contemplates the preparation and use of non-peptide peptidomimetics useful for mimicking the activity of peptides, which makes peptidomimetics additional sources of targeting ligands that may be attached to the viral vectors of the present invention.

Methods of generating and identifying peptidomimetics useful as described herein are known in the art; (see, e.g., WO 93/17032). For example, the aforementioned application describes a process of preparing peptidomimetic compounds useful for mimicking the activity of peptides and described the peptide-like activity of one such mimetic. Similarly, the production of peptidomimetic drugs via utilizing chemically modified moieties to mimic antibody structure, based on conformation studies, is described in U.S. Pat. No. 5,331,573. Methods of testing the drugs so prepared is also disclosed therein. Peptidomimetics of antibodies are thus useful as disclosed herein, not only as ligands but as molecules useful in linking viral particles to targeting ligands.

Other useful peptidomimetic molecules useful as ligands and/or "linkers" herein are described in published International App. No. WO 9220704; Brandt, et al., *Antimicrob Agents Chemother*, 40:1078, 1996; Sepp-Lorenzino, et al., *Cancer Res*, 55:5302, 1995; and Chander et al., *J Pharm Sci*, 84:404, 1995. Notwithstanding the fact that such mimetics are not true peptides, various covalent and non-covalent means of linking such peptidomimetic molecules to viral proteins may be used as disclosed herein.

e. Selection of Ligands that Bind Other Cell Surface Molecules

Ligands for use in the present invention may also be selected by a method such as phage display (see, for example, U.S. Pat. No. 5,223,409.) Briefly, in this method, DNA sequences are inserted into the gene III or gene VIII gene of a filamentous phage, such as M13. Several vectors with multicloning sites have been developed for insertion (McLafferty et al., *Gene* 128:29–36, 1993; Scott and Smith, *Science* 249:386–390, 1990; Smith and Scott, *Methods Enzymol.* 217:228–257, 1993). Using tumor cell targeting as an example, the inserted DNA sequences may be randomly generated or be variants of a known binding domain for binding tumor cells. Single chain antibodies may readily be generated using this method. Generally, the inserts encode from 6 to 20 amino acids. The peptide encoded by the inserted sequence is displayed on the surface of the bacteriophage. Bacteriophage expressing a binding domain for tumor cells are selected for by binding to tumor cells. Unbound phage are removed by a wash, typically containing 10 mM Tris, 1 mM EDTA, and without salt or with a low salt concentration. Bound phage are eluted with a salt containing buffer, for example. The NaCl concentration is increased in a step-wise fashion until all the phage are eluted. Typically, phage binding with higher affinity will be released by higher salt concentrations.

Eluted phage are propagated in the bacteria host. Further rounds of selection may be performed to select for a few phage binding with high affinity. The DNA sequence of the insert in the binding phage is then determined. Once the predicted amino acid sequence of the binding peptide is known, sufficient peptide for use herein as an nucleic acid binding domain may be made either by recombinant means or synthetically. Recombinant means is used when the receptor-binding internalized ligand/nucleic acid binding domain is produced as a fusion protein. The peptide may be generated as a tandem array of two or more peptides, in order to maximize affinity or binding.

f. Identifying and Isolating Internalizing Molecules

Any and all molecules that mimic or interact with a cell surface molecule that is trafficked to the nucleus are also included within the scope of the present invention. One exemplary method of identifying and isolating such molecules is essentially as follows.

First, one may identify a cell or tissue of interest—e.g., a cell to which one wishes to target a therapeutic moiety. Next, generate antibodies—preferably, monoclonal antibodies—to the cell surface of the putative target cell. Identify and isolate hybridomas secreting the antibodies to the cell surface. Methods of generating monoclonal antibodies and of identifying hybridomas producing said antibodies are known in the art.

As a next step, the monoclonal antibodies are admixed with a culture of target cells and allowed to incubate for a predetermined period of time. Subsequently, a second antibody is added to the admixture—that is, an antibody to the first antibody (anti-idiotype antibody). Preferably, the second antibody is toxic to the target cell upon internalization and delivery to the nucleus; in this manner, cell death is indicative of internalization of the first antibody, to which the second antibody is bound.

By screening the cell cultures, one may readily identify and isolate all killing antibody complexes and may separate out the antibodies that possess the ability to translocate to the nucleus. Such antibodies may then be used according to the methods disclosed herein—e.g., they may be used to target and deliver viral vectors to target cell populations.

Although the foregoing example discusses the generation and identification of antibodies, it is understood that useful ligands of the present invention are not restricted to antibodies. Any molecule, for example, that mimics the ability of FGF and/or FGFR to be trafficked directly to the nucleus is contemplated for use as disclosed herein. Thus, any molecule that interacts with a cell surface molecule that is trafficked to the nucleus is contemplated by the present disclosure.

2. Modification of Receptor-Binding Internalized Ligands

The ligands for use herein may be customized for a particular application. Means for modifying proteins is provided below. Briefly, additions, substitutions and deletions of amino acids may be produced by any commonly employed recombinant DNA method. Modified peptides, especially those lacking proliferative function, and chimeric peptides, which retain their specific binding and internalizing activities, are also contemplated for use herein. Modifications also include the addition or deletion of residues, such as the addition of a cysteine to facilitate conjugation and to form conjugates that contain a defined molar ratio (e.g., 1:1) of the polypeptides (see, e.g., U.S. Pat. No. 5,175,147; PCT Application No. WO 89/00198, U.S. Ser. No. 07/070,797, abandoned Dec. 29, 1988; PCT Application No. WO 91/15229; and U.S. Ser. No. 07/505,124, abandoned Nov. 4, 1992). Still other useful modifications include adding sequence that are subject to post-translational modification (e.g., myristylation, palmatylation, phophorylation, ribosylation) that improve or alter protein function, stability or the like.

As noted above, any ligand that binds to a cell surface receptor and is internalized may be used within the context of this invention. Such ligands may be polypeptides or peptide analogues, including peptidomimetics. Ligands also include fragments thereof, or constrained analogues of such peptides that bind to the receptor and internalize a linked targeted agent. Members of the FGF family, including FGF-1 to FGF-15, are preferred. Modified peptides, especially those lacking proliferative function, and chimeric peptides, which retain the specific binding and internalizing activities are also contemplated for use herein.

Modification of the polypeptide may be effected by any means known to those of skill in this art. The preferred methods herein rely on modification of DNA encoding the polypeptide and expression of the modified DNA. DNA encoding one of the receptor-binding internalized ligands discussed above may be mutagenized using standard methodologies. For example, cysteine residues that are responsible for aggregate formation may be deleted or replaced. If necessary, the identity of cysteine residues that contribute to aggregate formation may be determined empirically, by deleting and/or replacing a cysteine residue and ascertaining whether the resulting protein aggregates in solutions containing physiologically acceptable buffers and salts. In addition, fragments of these receptor-binding internalized ligands may be constructed and used. The binding region of many of these ligands have been delineated. For example, the receptor binding region of FGF2 has been identified by mutation analysis and FGF peptide agonists/antagonists to reside between residues 33–77 and between 102–129 of the 155 amino acid form (Baird et al., *PNAS* 85:2324; Erickson et al., *Biochem.* 88:3441). Exons 1–4 of VEGF are required for receptor binding. Fragments may also be shown to bind and internalize by any one of the tests described herein.

Mutations may be made by any method known to those of skill in the art, including site-specific or site-directed mutagenesis of DNA encoding the protein and the use of DNA amplification methods using primers to introduce and amplify alterations in the DNA template, such as PCR splicing by overlap extension (SOE). Site-directed mutagenesis is typically effected using a phage vector that has single- and double-stranded forms, such as M13 phage vectors, which are well-known and commercially available. Other suitable vectors that contain a single-stranded phage origin of replication may be used (see, e.g., Veira et al., *Meth. Enzymol.* 15:3, 1987). In general, site-directed mutagenesis is performed by preparing a single-stranded vector that encodes the protein of interest (i.e., a member of the FGF family or a therapeutic molecule, such as an intrabody). An oligonucleotide primer that contains the desired mutation within a region of homology to the DNA in the single-stranded vector is annealed to the vector followed by addition of a DNA polymerase, such as *E. coil* DNA polymerase I (Klenow fragment), which uses the double stranded region as a primer to produce a heteroduplex in which one strand encodes the altered sequence and the other the original sequence. The heteroduplex is introduced into appropriate bacterial cells and clones that include the desired mutation are selected. The resulting altered DNA molecules may be expressed recombinantly in appropriate host cells to produce the modified protein.

Suitable conservative substitutions of amino acids are well-known and may be made generally without altering the biological activity of the resulting molecule. For example, such substitutions are generally made by interchanging within the groups of polar residues, charged residues, hydrophobic residues, small residues, and the like. If necessary, such substitutions may be determined empirically merely by testing the resulting modified protein for the ability to bind to and internalize upon binding to the appropriate receptors. Those that retain this ability are suitable for use in the conjugates and methods herein. As such, an amino acid residue of a receptor-binding internalized ligand is non-essential if the polypeptide that has been modified by deletion or alteration of the residue possesses substantially the same ability to bind to its receptor and internalize a linked agent as the unmodified polypeptide.

As used herein, "biological activity" generally refers to the activity of a compound or a physiological response that results upon in vivo administration of a compound, composition or other mixture. Biological activity thus encompasses therapeutic effects and pharmaceutical activity of such compounds, compositions, complexes, and mixtures. Biological activity also refers to the ability of a molecule to bind to a cell, to internalize and to localize to the nucleus. Biological activity may be determined with reference to particular in vitro activities as measured in a defined assay. For example, within the context of this invention, a biological activity of FGF, or fragments of FGF, is the ability of FGF to bind to cells bearing FGF receptors and internalize a linked agent. This activity may be assessed in vitro, e.g., by conjugating FGF to a cytotoxic agent (such as saporin), contacting cells bearing FGF receptors (e.g., fibroblasts) with the conjugate, and assessing cell proliferation or inhibition of growth. In vivo activity may be determined using recognized animal models, such as the mouse xenograft model for anti-tumor activity (see, e.g., Beitz et al., *Cancer Research* 52:227–230, 1992; Houghton et al., *Cancer Res.* 42:535–539, 1982; Bogden et al., *Cancer (Philadelphia)* 48:10–20, 1981; Hoogenhout et al., *Int. J. Radiat. Oncol., Biol. Phys.* 9:871–879, 1983; Stastny et al., *Cancer Res.* 53:5740–5744, 1993).

Binding to a receptor followed by internalization are the only activities required for a ligand to be suitable for use herein. However, some of the ligands are growth factors and cause mitogenesis. For example, all of the FGF proteins induce mitogenic activity in a wide variety of normal diploid mesoderm-derived and neural crest-derived cells. A test of such "FGF mitogenic activity," which reflects the ability to bind to FGF receptors and to be internalized, is the ability to stimulate proliferation of cultured bovine aortic endothelial cells (see, e.g., Gospodarowicz et al., *J. Biol. Chem.* 257:12266–12278, 1982; Gospodarowicz et al., *Proc. Natl. Acad. Sci. USA* 73:4120–4124, 1976). Muteins with reduced mitogenic activity are made by the methods described herein. In the Examples, FGF muteins with reduced mitogenic activity have been constructed by site-directed mutagenesis. Non- or reduced-mitogenic proteins can also be constructed by swapping the receptor-binding domain with the receptor-binding domain of a related protein. By way of example, the domain of FGF2 may be swapped with the receptor-binding domain of FGF7 to create an FGF that does not cause proliferation and may alter the binding profile.

If the FGF or other ligand has been modified so as to lack mitogenic activity or other biological activities, binding and internalization may still be readily assayed by any one of the following tests or other equivalent tests. Generally, these tests involve labeling the ligand, incubating it with target cells, and visualizing or measuring intracellular label. For example, briefly, FGF may be fluorescently labeled with FITC or radiolabeled with $^{125}$I. Fluorescein-conjugated FGF is incubated with cells and examined microscopically by fluorescence microscopy or confocal microscopy for internalization. When FGF is labeled with $^{125}$I, the labeled FGF is incubated with cells at 4° C. Cells are temperature shifted to 37° C. and washed with 2 M NaCl at low pH to remove any cell-bound FGF. Label is then counted and thereby measuring internalization of FGF.

Alternatively, in another method of assaying the binding and internalization abilities of a ligand, the ligand can be conjugated with a nucleic acid binding domain by any of the methods described herein and complexed with a plasmid encoding saporin or conjugated with saporin or other cytotoxic molecule and assessed for cytotoxicity. As discussed below, the complex may be used to transfect cells and cytotoxicity measured.

Finally, muteins of the FGFs are known to those of skill in the art (see, e.g., U.S. Pat. No. 5,175,147; PCT Application No. WO 89/00198, U.S. Ser. No. 07/070,797; PCT Application No. WO 91/15229; and U.S. Ser. No. 07/505,124). Such muteins may also be used according to the teachings of the present invention.

F. Payload

1. Therapeutic-Product-Encoding Molecules

Molecules that encode therapeutic products, which are also referred to herein as therapeutic nucleic acids, are molecules that effect a treatment upon or within a cell, generally by modifying gene transcription of translation. Therapeutic nucleic acids of the present invention may be used in the context of "positive" or "negative" gene therapy, depending on the effect one seeks to achieve.

For example, a therapeutic nucleotide sequence may encode all or a portion of a gene. If it encodes all (or the most critical functional portions) of a gene, it may effect genetic therapy by serving as a replacement for a defective gene. Such a sequence may also function by recombining with DNA already present in a cell, thereby replacing a defective portion of a gene.

A variety of positive gene therapy applications and therapeutic gene products are described hereinbelow and include such diverse applications as the treatment of ischemia, the promotion of wound healing, the stimulation of bone growth and regrowth, increased angiogenesis, and the like. The replacement of a defective or nonfunctional gene with one that produces the desired gene product is also considered "positive" gene therapy, whether one is replacing a dysfunctional or nonfunctional regulatory sequence or a sequence that encodes a structural protein.

Similarly, "negative" gene therapy is encompassed by the present invention as well. Thus, therapeutic nucleic acids of the present invention may encode products that reduce or halt hyperproliferative diseases (e.g. of SMCs; restenosis is one example), tumor formation and growth, metastasis, and the like, to name a few examples.

Further details regarding both positive and negative gene therapy applications are set forth below in subsequent sections of the specification. The following illustrations are thus intended to be exemplary and not limiting.

a. Gene Products for the Treatment of Ischemia

For example, in ischemia, endothelial and smooth muscle cells fail to proliferate. A construct that expresses FGF, alone or in combination with FGF protein to give short-term relief and induce FGF receptor, can be used to combat effects of ischemia. In such a case, FGF gene with a leader sequence to promote secretion is preferable. As well, the FGF gene is preferably driven by a constitutive promoter. In addition, muteins of the FGFs are known to those of skill in the art and may be useful as payload molecules as well as ligands. (See, e.g., U.S. Pat. No. 5,175,147; PCT Application No. WO 89/00198, U.S. Ser. No. 07/070,797, abandoned Dec. 29 1988; PCT Application No. WO 91/15229; and U.S. Ser. No. 07/505,124, abandoned Nov. 4, 1992.)

Other useful sequences which may be delivered using the vectors of the present invention include those encoding human superoxide dismutase (SOD) and analogs thereof (see, e.g., U.S. Pat. Nos. 5,455,029, 5,130,245 and 4,742,004) as well as opiod peptides (see, e.g., U.S. Pat. No. 4,684,624). Other sequences which encode therapeutic products useful as disclosed herein, whose GenBank numbers are provided in Section F.1.e. below, include sequences encoding IGF (see, e.g., U.S. Pat. Nos. 5,612,198 and 5,324,639); TGFβ1, TGFβ2, and TGFβ3 (see, e.g., U.S. Pat. Nos. 5,168,051, 5,482,851, 4,886,747, and 5,221,620); hepatocyte growth factor (HGF) (see, e.g., U.S. Pat. Nos. 5,547,856; 5,328,837; and 5,316,921); PDGF A (see, e.g., U.S. Pat. Nos. 5,605,816 and 5,219,759); and PDGF B (see, e.g., U.S. Pat. Nos. 5,272,064, 5,665,567).

Nucleic acid sequences encoding the following therapeutic products are also useful as payloads according to the present invention: VEGF 121, VEGF 165, FGF1, FGF2, FGF4, and FGF5. Sequence information for these molecules is provided elsewhere herein.

Finally, in all instances in which reference is made to publications, particularly patent applications and patents, it should generally be understood that the disclosures of all patent documents recited herein are incorporated by reference, as though fully set forth herein.

In addition, individuals afflicted with certain angiogenic diseases suffer from a paucity of angiogenic factor and may thus be deficient in microvasculature. Certain aspects of reproduction, such as ovulation, repair of the uterus after menstruation, and placental development depend on angiogenesis. For reproductive disorders with underlying angiogenic dysfunction, a construct that expresses FGF, VEGF, or other angiogenic factors may be beneficial. Useful sequences encoding such angiogenic factors are described in various sections herein, including sections E.1.a. and E.1.b.

b. Oligonucleotides

The conjugates provided herein may also be used to deliver a ribozyme, deoxyribozyme, antisense oligonucleotide, and the like to targeted cells. These nucleic acids may be present in the complex of ligand and nucleic acid binding domain or encoded by a nucleic acid in the complex. Alternatively, the nucleic acid may be directly linked to the ligand. Such products include antisense RNA, antisense DNA, ribozymes, triplex-forming oligonucleotides, and oligonucleotides that bind proteins. The nucleic acids can also include RNA trafficking signals, such as viral packaging sequences (see, e.g., Sullenger et al. (1994) *Science* 262:1566–1569).

Nucleic acids and oligonucleotides for use as described herein can be synthesized by any method known to those of skill in this art (see, e.g., WO 93/01286, U.S. application Ser. No. 07/723,454, abandoned Feb. 20, 1992; U.S. Pat. No. 5,218,088; U.S. Pat. No. 5,175,269; U.S. Pat. No. 5,109,124). Identification of oligonucleotides and ribozymes for use as antisense agents and DNA encoding genes for targeted delivery for genetic therapy involve methods well known in the art. For example, the desirable properties, lengths and other characteristics of such oligonucleotides are well known. Antisense oligonucleotides are typically designed to resist degradation by endogenous nucleolytic enzymes by using such linkages as: phosphorothioate, methylphosphonate, sulfone, sulfate, ketyl, phosphorodithioate, phosphoramidate, phosphate esters, and other such linkages (see, e.g., Agrwal et al., *Tetrahedron Lett*. 28:3539–3542 (1987); Miller et al., *J. Am. Chem. Soc*. 93:6657–6665 (1971); Stec et al., *Tetrahedron Lett*. 26:2191–2194 (1985); Moody et al., *Nucl. Acids Res*. 12:4769–4782 (1989); Uznanski et al., *Nucl. Acids Res*. (1989); Letsinger et al., *Tetrahedron* 40:137–143 (1984); Eckstein, *Annu. Rev. Biochem*. 54:367–402 (1985); Eckstein, *Trends Biol. Sci*. 14:97–100 (1989); Stein In: *Oligodeoxynucleotides. Antisense Inhibitors of Gene Expression*, Cohen, Ed, Macmillan Press, London, pp. 97–117 (1989); Jager et al., *Biochemistry* 27:7237–7246 (1988)).

Antisense nucleotides are oligonucleotides that bind in a sequence-specific manner to nucleic acids, such as mRNA or DNA. When bound to mRNA that has complementary sequences, antisense prevents translation of the mRNA (see, e.g., U.S. Pat. No. 5,168,053 to Altman et al.; U.S. Pat. No. 5,190,931 to Inouye, U.S. Pat. No. 5,135,917 to Burch; U.S. Pat. No. 5,087,617 to Smith and Clusel et al. (1993) *Nucl. Acids Res*. 21:3405–3411, which describes dumbbell antisense oligonucleotides). Triplex molecules refer to single DNA strands that bind duplex DNA forming a colinear triplex molecule, thereby preventing transcription (see, e.g., U.S. Pat. No. 5,176,996 to Hogan et al., which describes methods for making synthetic oligonucleotides that bind to target sites on duplex DNA).

Particularly useful antisense nucleotides and triplex molecules are molecules that are complementary or bind to the sense strand of DNA or mRNA that encodes a protein involved in cell proliferation, such as an oncogene or growth factor, (e.g., bFGF, int-2, hst-1/K-FGF, FGF-5, hst-2/FGF-6, FGF-8). Other useful antisense oligonucleotides include those that are specific for IL-8 (see, e.g., U.S. Pat. No. 5,241,049), c-src, c-fos H-ras (lung cancer), K-ras (breast cancer), urokinase (melanoma), BCL2 (T-cell lymphoma), IGF-1 (glioblastoma), IGF-1 receptor (glioblastoma), TGF-β1, and CRIPTO EGF receptor (colon cancer). These particular antisense plasmids reduce tumorigenicity in athymic and syngeneic mice.

These nucleic acids or nucleic acids that encode antisense can be linked to bFGF for the treatment of psoriasis. Anti-sense oligonucleotides or nucleic acids encoding anti-sense specific for nonmuscle myosin heavy chain and/or c-myb (see, e.g., Simons et al. (1992) *Circ. Res.* 70:835–843; PCT Application WO 93/01286, U.S. application Ser. No. 07/723,454, abandoned Feb. 20, 1992 LeClerc et al. (1991) *J. Am. Coll. Cardiol.* 17 (2 Suppl. A):105A; Ebbecke et al. (1992) *Basic Res. Cardiol.* 87:585–591) can be targeted by an FGF, for example to inhibit smooth muscle cell proliferation, such as occurs following angioplasty.

A ribozyme is an RNA molecule that specifically cleaves RNA substrates, such as mRNA, resulting in inhibition or interference with cell growth or expression. There are at least five known classes of ribozymes involved in the cleavage and/or ligation of RNA chains. Ribozymes can be targeted to any RNA transcript and can catalytically cleave such transcript (see, e.g., U.S. Pat. Nos. 5,272,262; 5,144,019; and U.S. Pat. Nos. 5,168,053, 5,180,818, 5,116,742 and 5,093,246 to Cech et al.). Any such ribozyme or nucleic acid encoding the ribozyme may be delivered to a cell bearing a receptor for a receptor-internalized binding ligand.

Ribozymes and the like may be delivered to the targeted cells by DNA encoding the ribozyme linked to a eukaryotic promoter, such as an eukaryotic viral promoter, such that upon introduction into the nucleus, the ribozyme will be directly transcribed. In such instances, the construct will also include a nuclear translocation sequence, generally as part of the ligand or as part of a linker between the ligand and nucleic acid binding domain.

c. Prodrugs

A nucleic acid molecule encoding a prodrug may alternatively be used within the context of the present invention. Prodrugs are inactive in the host cell until either a substrate or an activating molecule is provided. Most typically, a prodrug activates a compound with little or no cytotoxicity into a toxic compound. Three of the more often used prodrug molecules, all of which are suitable for use in the present invention, are nitroreductase, thymidine kinase (e.g. HSVtk) and cytosine deaminase (e.g. *E. coli* CD).

Briefly, a wide variety of gene products which either directly or indirectly activate a compound with little or no cytotoxicity into a toxic product may be utilized within the context of the present invention. Representative examples of such gene products include HSVTK (herpes simplex virus thymidine kinase) and VZVTK (*varicella zoster* virus thymidine kinase), which selectively phosphorylate certain purine arabinosides and substituted pyrimidine compounds. Phosphorylation converts these substrates (compounds) to metabolites that are cytotoxic or cytostatic. For example, exposure of the drugs ganciclovir, acyclovir, or any of their analogues (e.g., FIAU, FIAC, DHPG) to cells expressing HSVTK allows conversion of the drug into its corresponding active nucleotide triphosphate form.

Other gene products that may be utilized within the context of the present invention include *E. coli* guanine phosphoribosyl transferase, which converts thioxanthine into toxic thioxanthine monophosphate (Besnard et al., *Mol. Cell. Biol.* 7:4139–4141, 1987); alkaline phosphatase, which converts inactive phosphorylated compounds such as mitomycin phosphate and doxorubicin-phosphate to toxic dephosphorylated compounds; fungal (e.g., *Fusarium oxysporum*) or bacterial cytosine deaminase, which converts 5-fluorocytosine to the toxic compound 5-fluorouracil (Mullen, *PNAS* 89:33, 1992); carboxypeptidase G2, which cleaves glutamic acid from para-N-bis (2-chloroethyl) aminobenzoyl glutamic acid, thereby creating a toxic benzoic acid mustard; and Penicillin-V amidase, which converts phenoxyacetabide derivatives of doxorubicin and melphalan to toxic compounds (see generally, Vrudhula et al., *J. Med. Chem.* 36:919–923, 1993; Kern et al., *Canc. Immun. Immunother.* 31:202–206, 1990). Moreover, a wide variety of Herpesviridae thymidine kinases, including both primate and non-primate herpesviruses, are suitable. Such herpesviruses include Herpes Simplex Virus Type 1 (McKnight et al., *Nuc. Acids Res* 8:5949–5964, 1980), Herpes Simplex Virus Type 2 (Swain and Galloway, *J. Virol.* 46:1045–1050, 1983), *Varicella Zoster* virus (Davison and Scott, *J. Gen. Virol.* 67:1759–1816, 1986), marmoset herpesvirus (Otsuka and Kit, *Virology* 135:316–330, 1984), feline herpesvirus type 1 (Nunberg et al., *J. Virol.* 63:3240–3249, 1989), pseudorabies virus (Kit and Kit, U.S. Pat. No. 4,514,497, 1985), equine herpesvirus type 1 (Robertson and Whalley, *Nuc. Acids Res.* 16:11303–11317, 1988), bovine herpesvirus type 1 (Mittal and Field, *J. Virol* 70:2901–2918, 1989), turkey herpesvirus (Martin et al., *J. Virol.* 63:2847–2852, 1989), Marek's disease virus (Scott et al., *J. Gen. Virol.* 70:3055–3065, 1989), herpesvirus saimiri (Honess et al., *J. Gen. Virol.* 70:3003–3013, 1989) and Epstein-Barr virus (Baer et al., *Nature (London)* 310:207–311, 1984). Such herpesviruses may be readily obtained from commercial sources such as the American Type Culture Collection ("ATCC", Rockville, Md.).

Furthermore, as indicated above, a wide variety of inactive precursors may be converted into active inhibitors. For example, thymidine kinase can phosphorylate nucleosides (e.g., dT) and nucleoside analogues such as ganciclovir (9-{[2-hydroxy-1-(hydroxymethyl)ethoxyl methyl} guanosine), famciclovir, buciclovir, penciclovir, valciclovir, acyclovir (9-[2-hydroxy ethoxy)methyl] guanosine), trifluorothymidine, 1-[2-deoxy, 2-fluoro, beta-D-arabino furanosyl]-5-iodouracil, ara-A (adenosine arabinoside, vivarabine), 1-beta-D-arabinofuranoxyl thymine, 5-ethyl-2'-deoxyuridine, 5-iodo-5'-amino-2,5'-dideoxyuridine, idoxuridine (5-iodo-2'-deoxyuridine), AZT (3' azido-3' thymidine), ddC (dideoxycytidine), AIU (5-iodo-5' amino 2',5'-dideoxyuridine) and AraC (cytidine arabinoside).

Other gene products may render a cell susceptible to toxic agents. Such products include tumor necrosis factor, viral proteins, and channel proteins that transport drugs.

A cytocide-encoding agent may be constructed as a prodrug, which when expressed in the proper cell type is processed or modified to an active form. For example, the saporin gene may be constructed with an N- or C-terminal extension containing a protease-sensitive site. The extension renders the protein inactive and subsequent cleavage in a cell expressing the appropriate protease restores enzymatic activity.

d. Tumor Suppressor Genes

The definition of a tumor suppressor gene has recently been broadened to include genes (and their products) which are subject to frequent downregulation in cancer, suggestive of an important tumor-suppressing activity despite the lack of mutation. Examples of the foregoing include cell adhesion molecules such as E-cadherin (GenBank Accession No. Z18923), which play a role in tissue development and epithelial cell differentiation. E-cadherin expression correlates with epithelial differentiation, whereas loss of E-cadherin expression promotes epithelial dedifferentiation and invasiveness of human carcinoma cells. Thus, the restoration of E-cadherin function prevents invasiveness of epithelial tumor cells.

Human BGP (biliary glycoprotein) also mediates cell adhesion in a manner similar to the cadherins. Thus, BGP (GenBank Accession No. J03858) is another gene which may be used within the context of the present invention.

Other tumor-suppressor genes useful according to the present invention include the following. It should be noted, however, that this list is not exhaustive, only exemplary: Rb (GenBank Accession No. M15400); p53 (GenBank Accession Nos. X02469, M60950); CDKN2/PI6/MTS1 (GenBank Accession No. S78535,U12818); PTEN/MMAC1 (GenBank Accession No. U92436); APC (GenBank Accession No. M74088); p33ING1 (GenBank Accession No. AF001954); Smad4 (GenBank Accession No. U59914); maspin (GenBank Accession No. U04313); von Hippel-Lindau (VHL) (GenBank Accession Nos. AF010238, U19763,U68055,U687176,U49746); Wilms tumor (WT1) (GenBank Accession No. X69950); Bin1 (GenBank Accession No. U68485); Men1 (GenBank Accession Nos. U93237, U93326); Neurofibromatosis 2 (NF2) (GenBank Accession No. L27065); MXI1 (GenBank Accession No. L07648): and FHIT (GenBank Accession No. U46922).

e. Vascularization and Tissue Repair

A wide variety of therapeutic nucleic acid sequences encoding therapeutic gene products involved in vascularization, wound healing (e.g. the healing of chronic ulcers) and tissue repair, including the repair of connective tissue (e.g. bone), are appropriate for use in conjunction with the constructs, vectors and methods of the present invention. Sequences encoding the following VEGF and VEGF-related proteins and polypeptides are particularly useful for such applications and include the following: VEGF (Bovine; GenBank Accession No. M32976); VEGF (Bovine; GenBank Accession No. M31836); VEGF-C (GenBank Accession No. X94216); VEGF-B (GenBank Accession No. U48801); VEGF (GenBank Accession No. X62568); Angiopoietin-1 (GenBank Accession No. U83508); Angiogenin (GenBank Accession No. M11567); IGF-1 (GenBank Accession No. X03563); IGF-II (GenBank Accession Nos. X03562, M13970, M14116, M14117, M14118); HGF (GenBank Accession Nos. X16323, S80567); PDGF A (GenBank Accession No. X03795); PDGF B (GenBank Accession Nos. X02744, X02811); TGFB1 (GenBank Accession No. A23751); TGFB2 (GenBank Accession No. A23752); and TGFB3 (GenBank Accession No. A23753).

Still other useful therapeutic nucleotide sequences encode the following molecules—many of which are particularly useful in the repair of connective tissue, such as bone: PTH (GenBank Accession Nos. J00301, V00597); BMP1 (GenBank Accession Nos. M22488, Y08723; see also U.S. Pat. No. 5,108,922); BMP2(GenBank Accession No. M22489; also see U.S. Pat. No. 5,013,649); BMP3 (GenBank Accession No. M22491; see also U.S. Pat. No. 5,116,738); BMP5 (see U.S. Pat. Nos. 5,635,373 and 5,106, 748); BMP6 (see U.S. Pat. No. 5,187,076); BMP7 (see U.S. Pat. No. 5,141,905); BMP8 (see U.S. Pat. No. 5,688,678); BMP10 (see U.S. Pat. No. 5,637,480); BMP11 (see U.S. Pat. No. 5,639,638); mammalian BMPs (see U.S. Pat. No. 5,620, 867); tissue differentiation affecting factor (see U.S. Pat. No. 5,679,783); morphogenic protein OP-3 (see U.S. Pat. No. 5,652,118); osteoinductive factors (see U.S. Pat. No. 4,877, 864); osteogenic proteins (see U.S. Pat. Nos. 5,106,626, 4,968,590, and RE35694); and Xenopus BMPs (see U.S. Pat. No. 5,670,338).

The foregoing represent but a few examples of useful therapeutic sequences and gene products that may be utilized in tissue repair and revascularization. As noted below, many of those same sequences are useful in the repair of connective tissues, such as bone, and other tissue injuries.

For bone repair, sequences encoding bone morphogenic proteins (BMPs), parathyroid hormone (PTH) and insulin-like growth factors (IGFs) are of particular usefulness. The following genes are thus appropriate for use as payloads according to the teachings of the present invention: PTH (GenBank Accession Nos. J00301, V00597); BMP1 (GenBank Accession Nos. M22488, Y08723); BMP2 (GenBank Accession No. M22489); BMP3 (GenBank Accession No. M22491); IGF-1 (GenBank Accession No. X03563); and IGF-II (GenBank Accession Nos. X03562, M13970, M14116, M14117, M14118). Sequences encoding other BMPs such as BMP4, BMP5, BMP6, and the like are also useful as disclosed herein.

f. Apoptosis-Inducing Agents

There are many agents, both of a chemical and proteinaceous nature, that can induce apoptosis. Therefore, apoptosis-inducing agents are also therapeutic agents within the context of the present invention. Examples of nucleotide sequences which encode such agents, which sequences may be delivered with high specificity using the vectors of the present intention, include the following. As before, this listing is exemplary and is neither exhaustive nor limiting of the invention: p53 (GenBank Accession Nos. X02469, M60950); c-myc (GenBank Accession No. E01841); TNF-alpha (GenBank Accession No. E02870); Fas ligand (GenBank Accession No. U08137; see also U.S. Pat. Nos. 5,663,070 and 5,652,210; p38-mitogen activated protein (MAP) kinase (GenBank Accession No. L35253); and IFN-gamma (GenBank Accession Nos. E06017, A11033).

g. Cytocidal Gene Products

A cytocide-encoding agent is a nucleic acid molecule (e.g., DNA or RNA) that, upon internalization by a cell, and subsequent transcription (if DNA) and[/or] translation into a cytocidal agent, is cytotoxic or cytostatic, to a cell, for example, by inhibiting cell growth through interference with protein synthesis or through disruption of the cell cycle.

Cytocides include saporin, the ricins, abrin, gelonin, other ribosome inactivating proteins, Pseudomonas exotoxin, diphtheria toxin, angiogenin, tritin, dianthins 32 and 30, momordin, pokeweed antiviral protein, mirabilis antiviral protein, bryodin, angiogenin, and shiga exotoxin, as well as other cytocides that are known to those of skill in the art. Inhibitors of cell cycle are well known.

DNA molecules that encode an enzyme that results in cell death or renders a cell susceptible to cell death upon the addition of another product are preferred. For example, saporin is an enzyme that cleaves rRNA and inhibits protein synthesis. Other enzymes that inhibit protein synthesis are especially well suited for use in the present invention. Alternatively, the product may be a ribozyme, antisense, or other nucleic acid molecule that causes cell death.

Ribosome-inactivating proteins (RIPs), which include ricin, abrin, and saporin, are plant proteins that catalytically inactivate eukaryotic ribosomes. Ribosome-inactivating proteins inactivate ribosomes by interfering with the protein elongation step of protein synthesis. For example, the ribosome-inactivating protein saporin (also referred to as SAP) has been shown to inactivate 60S ribosomes by cleavage of the N-glycosidic bond of the adenine at position 4324 in the rat 28S ribosomal RNA (rRNA).

Several structurally related ribosome inactivating proteins have been isolated from seeds and leaves of the plant *Saponaria officinalis* (soapwort) (GB Patent 2,194,241 B; GP Patent 2,216,891; EP Patent 89306016). Saporin proteins for use in this invention have amino acid sequences found in the natural plant host *Saponaria officinalis* (e.g., SEQ ID NO. 22) or modified sequences, such as amino acid substitutions, deletions, insertions or additions, but that still express substantial ribosome inactivating activity. Several molecular isoforms of the protein are also known. Any of these saporin proteins or modified proteins that are cytotoxic may be used in the present invention. Other suitable saporin polypeptides include other members of the multi-gene family coding for isoforms of saporin-type ribosome inactivating proteins including SO-1 and SO-3 (Fordham-Skelton et al., *Mol. Gen. Genet.* 221:134–138, 1990), SO-2 (see, e.g., U.S. application Ser. No. 07/885,242, abandoned Oct. 17, 1993; GB 2,216,891; see also Fordham-Skelton et al., *Mol. Gen. Genet.* 229:460–466, 1991), SO-4 (see, e.g., GB 2,194, 241 B; see also Lappi et al., *Biochem. Biophys. Res. Commun.* 129:934–942, 1985) and SO-5 (see, e.g., GB 2,194,241 B; see also Montecucchi et al., *Int. J. Peptide Protein Res.* 33:263–267, 1989). Any such protein, or portion thereof, that exhibits cytotoxicity in standard in vitro or in vivo assays within at least about an order of magnitude of the saporin conjugates described herein is contemplated for use herein.

Ribosome inactivating protein encoding DNA sequences may use mammalian-preferred codons (SEQ. ID NO. 23). Preferred codon usage as exemplified in *Current Protocols in Molecular Biology*, infra, and Zhang et al. (*Gene* 105:61, 1991) for mammals, yeast, Drosophila, *E. coli*, and primates is established for saporin sequences.

In addition to saporin discussed above, other cytocides that inhibit protein synthesis are useful in the present invention. The gene sequences for these cytocides may be isolated by standard methods, such as PCR, probe hybridization of genomic or cDNA libraries, antibody screenings of expression libraries, or clones may be obtained from commercial or other sources. The DNA sequences of many of these cytocides are well known, including ricin A chain (GenBank Accession No. X02388); maize ribosome inactivating protein (GenBank Accession No. L26305); gelonin (GenBank Accession No. L12243; PCT Application WO 92/03155; U.S. Pat. No. 5,376,546; diphtheria toxin (GenBank Accession No. K01722); trichosanthin (GenBank Accession No. M34858); tritin (GenBank Accession No. D13795); pokeweed antiviral protein (GenBank Accession No. X78628); mirabilis antiviral protein (GenBank Accession No. D90347); dianthin 30 (GenBank Accession No. X59260); abrin (GenBank Accession No. X55667); shiga (GenBank Accession No. M19437) and Pseudomonas exotoxin (GenBank Accession Nos. K01397, M23348). When DNA sequences or amino acid sequences are known, DNA molecules encoding these proteins may be synthesized, and may contain mammalian-preferred codons.

The therapeutic product-encoding agent, such as saporin DNA sequence, is introduced into a plasmid in operative linkage with an appropriate promoter for expression of polypeptides in the organism. The plasmid can optionally include sequences, such as origins of replication that allow for the extrachromosomal maintenance of the saporin-containing plasmid, or can be designed to integrate into the genome of the host (as an alternative means to ensure stable maintenance in the host).

In addition to saporin discussed above, other cytocides that inhibit protein synthesis are useful in the present invention. The gene sequences for these cytocides may be isolated by standard methods, such as PCR, probe hybridization of genomic or cDNA libraries, antibody screenings of expression libraries, or clones may be obtained from commercial or other sources. The DNA sequences of many of these cytocides are well known, including ricin A chain (GenBank Accession No. X02388); maize ribosome inactivating protein (GenBank Accession No. L26305); gelonin (GenBank Accession No. L12243; PCT Application WO 92/03155; U.S. Pat. No. 5,376,546; diphtheria toxin (GenBank Accession No. K01722); trichosanthin (GenBank Accession No. M34858); tritin (GenBank Accession No. D13795); pokeweed antiviral protein (GenBank Accession No. X78628); mirabilis antiviral protein (GenBank Accession No. D90347); dianthin 30 (GenBank Accession No. X59260); abrin (GenBank Accession No. X55667); shiga (GenBank Accession No. M19437) and Pseudomonas exotoxin (GenBank Accession Nos. K01397, M23348). When DNA sequences or amino acid sequences are known, DNA molecules encoding these proteins may be synthesized, and may contain mammalian-preferred codons.

2. Promoters and Additional Elements

A therapeutic product-encoding agent of the present invention, such as a DNA sequence, is generally introduced into a plasmid in operative linkage with an appropriate promoter for expression of polypeptides in the recipient cells. The plasmid can optionally include sequences such as origins of replication that allow for the extrachromosomal maintenance of the saporin-containing plasmid, or can be designed to integrate into the genome of the host (as an alternative means to ensure stable maintenance in the host).

In general, constructs will also contain elements necessary for transcription and translation. The choice of the promoter will depend upon the cell type to be transformed and the degree or type of control desired. Promoters can be constitutive or active in any cell type, tissue specific, cell specific, event specific, temporal-specific or inducible. Cell-type specific promoters and event type specific promoters are preferred. Examples of constitutive or nonspecific promoters include the SV40 early promoter (U.S. Pat. No. 5,118,627), the SV40 late promoter (U.S. Pat. No. 5,118, 627), CMV early gene promoter (U.S. Pat. No. 5,168,062), and adenovirus promoter. In addition to viral promoters, cellular promoters are also amenable within the context of this invention. In particular, cellular promoters for the so-called housekeeping genes are useful. Viral promoters are preferred, because generally they are stronger promoters than cellular promoters.

Tissue specific promoters are particularly useful for expression in a wide variety of cells, including endothelial and smooth muscle cells. By using one of this class of promoters, an extra margin of specificity can be attained. SMC-specific promoters are particularly useful in targeting proliferative diseases involving SMC. For example, FGFR promoter, EGFR promoter, PDGF receptor promoter, integrin receptor promoters, α-actin promoter, SM1 and SM2 myosin heavy chain promoters, calponin-h1 promoter, SM22 alpha angiotensin receptor promoter, are useful within the context of this invention.

Exemplary tissue-specific promoters include alpha-crystalline, tyrosinase, α-fetoprotein, prostate specific antigen, CEA, α-actin, VEGF receptor, erbB-2, C-myc, cyclin D, FGF receptor, gamma-crystalline promoter, tek, tie, urokinase receptor, E-selectin, P-selectin, VCAM-1, endoglin, endosialin, alpha$_v$ integrin, β$_3$ integrin, endothelin-1, ICAM-3, E9, von Willebrand Factor, CD-44, CD40, vascular endothelial cadherin, notch 4 and high molecular weight melanoma-associated antigen.

Endothelial-specific promoters are especially useful in targeting proliferative diseases involving endothelial cells. For treating diseases dependent or exacerbated by angiogenesis or primary angiogenic diseases, the following promoters are especially useful: VEGF-receptor promoter (Morishita et al., *J. Biol. Chem.* 270:27948, 1995; GenBank Accession No. X89776); FGF receptor promoter; TEK or tie 2 promoter, a receptor tyrosine kinase expressed predominately in endothelium of actively growing blood vessels (Huang et al., *Oncogene* 11:2097, 1995; GenBank Accession No. L06139); tie (WO 96/09381; Korhonen et al., *Blood* 86:1828, 1995; GenBank Accession No. X60954; GenBank Accession No. S89716); urokinase receptor, which is expressed at high levels in endothelial cells during angiogenesis (Hollas et al., *Cancer Res.* 51:3690, 1991; Gum et al., *Anti-Cancer Res.* 15:1167, 1995; Soravia et al., *Blood* 86:624, 1995; GenBank Accession No. S78532); E- and P-selectin, which has increased expression in endothelium of tumors, such as breast (Fox et al., *J. Pathol.* 177:369, 1995; Biancone et al., *J. Exp. Med.* 183:581, 1996; GenBank Accession No. M64485; GenBank Accession No. L01874); VCAM-1 (lademarco et al., *J. Biol. Chem.* 267:16323, 1992; GenBank Accession No. M92431); endoglin, which is upregulated in the vasculature of tumors (Bellon et al., *Eur. J. Immunol.* 23:2340, 1993; Gougos and Letarte, *J. Biol. Chem.* 265:8361, 1990; GenBank Accession No. HSENDOG); endosialin, expressed preferentially in tumor capillaries (Rettig et al., *PNAS* 89:10832, 1992); alpha V-beta3 integrin (Villa-Garcia et al., *Blood* 3:668, 1994; Donahue et al., *BBA* 1219:228, 1994); endothelin-1, a growth factor for endothelial cells (GenBank Accession No. M25377; GenBank Accession No. J04819; GenBank Accession No. J05489); ICAM-3, expressed in tumor endothelium (Patey et al., *Am. J. Pathol.* 148:465, 1996; Fox et al., *J. Path.* 177:369, 1995; GenBank Accession No. S50015); E9 antigen, upregulated in tumor endothelium (Wang et al., *Int. J. Cancer* 54:363, 1993); von Willebrand factor (Jahroudi and Lynch, *Mol. Cell. Biol.* 14:999, 1994; GenBank Accession No. HUMVWFI; GenBank Accession No. HUMVWFA); CD44 (Hofmann et al., *Cancer Res.* 53:1516, 1993; Maltzman et al., *Mol. Cell. Biol.* 16:2283, 1996; GenBank Accession No. HUMCD44B); CD40 (Pammer et al., *Am. J. Pathol.* 148:1387, 1996; GenBank Accession No. HACD40L; GenBank Accession No. HSCD405FR); vascular-endothelial cadherin, highly expressed in endothelial cells of hemangiomas (Martin-Padura et al., *J. Pathol.* 175:51, 1995); notch 4 (Uyttendaele et al., *Development* 122:2251, 1996) and high molecular weight melanoma-associated antigen.

Inducible promoters may also be used. These promoters include MMTV LTR (PCT WO 91/13160), inducible by dexamethasone, metallothionein, inducible by heavy metals, and promoters with cAMP response elements, inducible by cAMP. By using an inducible promoter, the nucleic acid may be delivered to a cell and will remain quiescent until the addition of the inducer. This allows further control on the timing of production of the gene product.

Event-type specific promoters are active or up-regulated only upon the occurrence of an event, such as tumorigenicity or viral infection. The HIV LTR is a well known example of an event-specific promoter. The promoter is inactive unless the tat gene product is present, which occurs upon viral infection. Some event-type promoters are also tissue-specific.

Additionally, promoters that are coordinately regulated with a particular cellular gene may be used. For example, promoters of genes that are coordinately expressed when a particular FGF receptor gene is expressed may be used. Then, the nucleic acid will be transcribed when the FGF receptor, such as FGFR1, is expressed, and not when FGFR2 is expressed. This type of promoter is especially useful when one knows the pattern of FGF receptor expression in a particular tissue, so that specific cells within that tissue may be killed upon transcription of a cytotoxic agent gene without affecting the surrounding tissues.

If the domain binds in a sequence specific manner, the construct must contain the sequence that binds to the nucleic acid binding domain. As described below, the target nucleotide sequence may be contained within the coding region of the cytocide, in which case, no additional sequence need be incorporated. Additionally, it may be desirable to have multiple copies of target sequence. If the target sequence is coding sequence, the additional copies must be located in non-coding regions of the cytocide-encoding agent. The target sequences of the nucleic acid binding domains are typically generally known. If unknown, the target sequence may be readily determined. Techniques are generally available for establishing the target sequence (e.g., see PCT Application WO 92/05285 and U.S. Ser. No. 586,769, abandoned Mar. 3, 1993).

In addition to the promoter, repressor sequences, negative regulators, or tissue-specific silencers may be inserted to reduce non-specific expression of the cytocide or prodrug. Multiple repressor elements may be inserted in the promoter region. Repression of transcription is independent on the orientation of repressor elements or distance from the promoter. One type of repressor sequence is an insulator sequence. Such sequences inhibit transcription (Dunaway et al., *Mol Cell Biol* 17: 182–9, 1997; Gdula et al., *Proc Natl Acad Sci USA* 93:9378–83, 1996, Chan et al., *J Virol* 70: 5312–28, 1996; Scott and Geyer, *EMBO J* 14: 6258–67, 1995; Kalos and Fournier, *Mol Cell Biol* 15: 198–207, 1995; Chung et al., *Cell* 74: 505–14, 1993) and will silence background transcription.

Negative regulatory elements have been characterized in the promoter regions of a number of different genes. The repressor element functions as a repressor of transcription in the absence of factors, such as steroids, as does the NSE in the promoter region of the ovalbumin gene (Haecker et al., *Mol. Endocrinology* 9:1113–1126, 1995). These negative regulatory elements bind specific protein complexes from oviduct, none of which are sensitive to steroids. Three different elements are located in the promoter of the ovalbumin gene. Oligonucleotides corresponding to portions of these elements repress viral transcription of the TK reporter. One of the silencer elements shares sequence identity with silencers in other genes (TCTCTCCNA).

Repressor elements have also been identified in the promoter region of collagen II gene. Gel retardation studies showed that nuclear factors from HeLa cells bind specifically to DNA fragments containing the silencer region, whereas chondrocyte nuclear extracts did not show any binding activity (Savanger et al., *J. Biol. Chem.* 265(12) :6669–6674, 1990). Repressor elements have also been shown to regulate transcription in the carbamyl phosphate synthetase gene (Goping et al., *Nucleic Acid Research* 23(10):1717–1721, 1995). This gene is expressed in only two different cell types, hepatocytes and epithelial cells of the intestinal mucosa. Negative regulatory regions have also been identified in the promoter region of the choline acetyl-transferase gene, the albumin promoter (Hu et al., *J. Cell Growth Difer.* 3(9):577–588, 1992), phosphoglycerate kinase (PGK-2) gene promoter (Misuno et al., *Gene* 119(2): 293–297, 1992), and in the 6-phosphofructo-2-kinase/ fructose-2, 6-bisphosphatase gene, in which the negative regulatory element inhibits transcription in non-hepatic cell lines (Lemaigre et al., *Mol. Cell Biol.* 11(2):1099–1106). Furthermore, the negative regulatory element Tse-1 has been identified in a number of liver specific genes, including tyrosine aminotransferase (TAT). TAT gene expression is liver specific and inducible by both glucocorticoids and the cAMP signaling pathway. The cAMP response element (CRE) has been shown to be the target for repression by Tse-1 and hepatocyte-specific elements (Boshart et al., *Cell* 61(5):905–916, 1990).

In preferred embodiments, elements that increase the expression of the desired product are incorporated into the construct. Such elements include internal ribosome binding sites (IRES; Wang and Siddiqui, *Curr. Top. Microbiol. Immunol* 203:99, 1995; Ehrenfeld and Semler, *Curr. Top. Microbiol. Immunol.* 203:65, 1995; Rees, et al., *Biotechniques* 20:102, 1996; Sugimoto et al., *Biotechnology* 12:694, 1994). IRES increase translation efficiency. As well, other sequences may enhance expression. For some genes, sequences especially at the 5' end inhibit transcription and/or translation. These sequences are usually palindromes that can form hairpin structures. Any such sequences in the nucleic acid to be delivered are generally deleted. Expression levels of the transcript or translated product are assayed to confirm or ascertain which sequences affect expression. Transcript levels may be assayed by any known method, including Northern blot hybridization, Rnase probe protection and the like. Protein levels may be assayed by any known method, including ELISA.

Other elements may be incorporated into the construct. In preferred embodiments, the construct includes a transcription terminator sequence, including a polyadenylation sequence, splice donor and acceptor sites, and an enhancer. Other elements useful for expression and maintenance of the construct in mammalian cells or other eukaryotic cells may also be incorporated (e.g., origin of replication). Because the constructs are conveniently produced in bacterial cells, elements that are necessary or enhance propagation in bacteria are incorporated. Such elements include an origin of replication, selectable marker and the like (see discussion below).

An additional level of control for initiating expression of the nucleic acid only in appropriate cells or enhancing uptake of complex is the delivery of two constructs, one of which encodes the cytocide and the other construct encodes a second gene that controls expression of the promoter driving the cytocide or prodrug or enhances uptake of the complexes into tumor masses or other target cells. By way of example, on one construct, the cytocide encoding agent is controlled by a promoter, such as a heat shock promoter. The second construct is a gene, such as a gene that elicits SOS pathway under control of a tumor-specific promoter. The two constructs are co-delivered or sequentially delivered. When delivered into tumor cells, the SOS gene is expressed and results in causing expression of the cytocide-encoding agent. In this case, the two constructs could be merged into one construct.

In the other type of multiple delivery system, the first construct is a cytocide gene under control of a promoter, such as those described above. The second construct comprises a different promoter controlling expression of a gene, such as IL-2, that induces leakiness in a tumor mass to allow better penetration. When the second construct is introduced first, the tumor mass will be more readily accessible for the first construct to be delivered.

Typically, the constructs are plasmid vectors. A preferred construct is a modified pNASS vector (Clontech, Palo Alto, Calif.). In the modified vector, amp. R gene is replaced by kan. R gene, a poly A signal sequence is added upstream of the mammalian promoter. A T7 promoter is added downstream of the mammalian promoter and upstream of the cytocide or prodrug gene to facilitate verification of cytotoxic activity. Other suitable mammalian expression vectors are well known (see, e.g., Ausubel et al., 1995; Sambrook et al., supra; Invitrogen catalogue, San Diego, Calif.; Novagen, Madison, Wis.; Pharmacia catalogue, Uppsala, Sweden; and others).

G. Formulation and Administration of Pharmaceutical Compositions

The retargeted viral vectors and complexes provided herein are useful in the treatment and prevention of various diseases. While certain diseases are listed below as examples, it is to be understood that the vectors, complexes, conjugates, and other constructs disclosed herein are useful in a wide variety of therapeutic applications, including the treatment of proliferative disease, quiescent disease, and metabolic disease. As noted previously, the origin of the disease is irrelevant; thus, whether the condition or disease is genetic, congenital, or acquired, the compositions and methods of the present invention are particularly useful in therapeutic interventions.

As used herein, "treatment" or "therapy" means any manner in which the symptoms of a condition, disorder or disease are ameliorated or otherwise beneficially altered. Treatment also encompasses any pharmaceutical use of the compositions herein, whether said uses are in vivo, ex vivo, or in vitro. As used herein, "amelioration" of the symptoms of a particular disorder refers to any lessening, whether permanent or temporary, lasting or transient, that can be attributed to or associated with administration of the composition.

1. Treatment of Tumors

As noted above, the compositions of the present invention are used to treat tumors. In these diseases, cell growth is excessive or uncontrolled. Tumors suitable for treatment within the context of this invention include, but are not limited to, breast tumors, gliomas, melanomas, prostate cancer, hepatomas, sarcomas, lymphomas, leukemias, ovarian tumors, thymomas, nephromas, pancreatic cancer, colon cancer, head and neck cancer, stomach cancer, lung cancer, mesotheliomas, myeloma, neuroblastoma, retinoblastoma, cervical cancer, uterine cancer, and squamous cell carcinoma of skin. As discussed above, ligands for these cancers bind to cell surface receptors that are generally preferentially expressed in tumors. Many of these cell surface receptors and their ligands are known. For tumors without such ligand-receptor pairs, ligands, such as antibodies, can be developed.

Through delivery of the compositions of the present invention, unwanted growth of cells may be slowed or halted, thus ameliorating the disease. The methods utilized herein specifically target and kill or halt proliferation of tumor cells having receptors for the ligand on their surfaces. This treatment is suitable for warm-blooded animals: mammals, including, but not limited to, humans, horses, dogs, and cats, and for non-mammals, such as avian species. Methods of treating such animals with these FGF conjugates are provided herein. These conjugates are shown to be effective against tumors, as well as against other pathophysiological conditions caused by a proliferation of cells which are sensitive to FGF mitogenic stimulation.

2. Treatment of SMC Disorders

The conjugates may be used to treat or prevent atherosclerosis and stenosis, a process and the resulting condition that occurs following angioplasty in which the arteries become reclogged. Generally, treatment of atherosclerosis involves widening a stenotic vascular lumen, permitting greater blood flow and oxygenation to the distal tissue.

Unfortunately, these procedures induce a normal wound healing response in the vasculature that results in restenosis. Of the three components to the normal vascular response to injury, thrombosis, elastic recoil and smooth muscle cell proliferation, anti-thrombotics/platelet inhibitors and vascular stents effectively address acute/subacute thrombosis and elastic recoil, respectively. However, no therapy can modify the vascular remodeling that is due to proliferation of smooth muscle cells at the lesion, their deposition of extracellular matrix and the subsequent formation of a neointima. Accordingly, restenosis remains a significant clinical problem.

Wound response also occurs after other interventions, such as balloon angioplasty of coronary and peripheral vessels, with or without stenting; carotid endarterectomies; vein grafts; and synthetic grafts in peripheral arteries and arteriovenous shunts. Although the time course of the wound response is not well defined, if the response can be suppressed for a short term (approximately 2 weeks), a long term benefit is achieved.

3. Treatment of Angiogenic Diseases

As noted above, the compositions of the present invention are used to treat angiogenesis-dependent diseases. In these diseases, vascular growth is excessive or allows unwanted growth of other tissues by providing blood supply. These diseases include angiofibroma, arteriovenous malformations, arthritis, atherosclerotic plaques, corneal graft neovascularization, delayed wound healing, diabetic retinopathy, granulations due to bums, hemangiomas, hemophilic joints, hypertrophic scars, neovascular glaucoma, nonunion fractures, Osler-weber syndrome, psoriasis, pyogenic granuloma, retrolental fibroplasia, scleroderma, solid tumors, trachoma, and vascular adhesions.

By inhibiting vessel formation (angiogenesis), unwanted growth may be slowed or halted, thus ameliorating the disease. In a normal vessel, a single layer of endothelial cells lines the lumen. Growth of a vessel requires proliferation of endothelial cells and smooth muscle cells. As such, the present invention provides nucleic acid delivery vehicles that bind to cell surface molecules (receptors) via a ligand and internalize, thus delivering a nucleic acid molecule.

4. Positive Gene Therapy

The molecules, constructs and methods of the present invention may also be useful in a wide variety of so-called "positive gene therapy" applications. Since positive gene therapy applications have been discussed in detail in earlier sections of the specification, that information will not be repeated herein. Nevertheless, it should be apparent to one of skill in the art that the molecules, constructs and methods of the present invention are able to effect a treatment upon or within a cell, generally by modifying gene transcription of translation, which makes them ideal in a variety of "positive" gene therapy applications, such as the stimulation of wound repair and bone regrowth.

A wide variety of positive gene therapy applications and therapeutic gene products have thus been described above and include such diverse applications as the treatment of ischemia, the promotion of wound healing, the stimulation of bone growth and regrowth, increased vascularization, and the like. The augmentation or replacement of a "defective" or nonfunctional gene with one that produces the desired gene product is also considered "positive" gene therapy, whether one is replacing a dysfunctional or nonfunctional regulatory sequence or a sequence that encodes a structural protein.

5. Preparation of Pharmaceutical Agents

Pharmaceutical carriers or vehicles suitable for administration of the conjugates and complexes provided herein include any such carriers known to those skilled in the art to be suitable for the particular mode of administration. In addition, the conjugates and complexes may be formulated as the sole pharmaceutically active ingredient in the composition or may be combined with other active ingredients.

The conjugates and complexes can be administered by any appropriate route, for example, orally, parenterally, including intravenously, intradermally, subcutaneously, or topically, in liquid, semi-liquid or solid form and are formulated in a manner suitable for each route of administration. Preferred modes of administration depend upon the indication treated. Dermatological and ophthalmologic indications will typically be treated locally; whereas, tumors and restenosis, will typically be treated by systemic, intradermal, or intramuscular modes of administration.

The conjugates and complexes herein may be formulated into pharmaceutical compositions suitable for topical, local, intravenous and systemic application. For ophthalmic uses, local administration, either by topical administration or by injection is preferred.

Time release formulations are also desirable, irrespective of the route or form in which the conjugates and complexes of the present invention are administered. Effective concentrations of one or more of the conjugates and complexes are mixed with a suitable pharmaceutical carrier or vehicle. As used herein an "effective amount" of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Repeated administration may be required to achieve the desired amelioration of symptoms.

As used herein, "an effective amount" is that amount which, in the composition administered and by the technique administered, provides an amount of therapeutic agent to the involved tissues sufficient to prevent or reduce cell proliferation or to ameliorate quiescent or metabolic disease.

The concentrations or amounts of the conjugates and complexes that are effective requires delivery of an amount, upon administration, that ameliorates the symptoms or treats the disease. Typically, the compositions are formulated for single dosage administration. Therapeutically effective concentrations and amounts may be determined empirically by testing the conjugates and complexes in known in vitro and in vivo systems, such as those described here; dosages for humans or other animals may then be extrapolated therefrom.

The conjugate is included in the pharmaceutically acceptable carrier in an amount sufficient to exert a therapeutically useful effect in the absence of undesirable side effects on the patient treated. The conjugates may be delivered as pharmaceutically acceptable salts, esters or other derivatives of the conjugates include any salts, esters or derivatives that may be readily prepared by those of skill in this art using known methods for such derivatization and that produce compounds that may be administered to animals or humans without substantial toxic effects. It is understood that number and degree of side effects depends upon the condition for which the conjugates and complexes are administered. For example, certain toxic and undesirable side effects are tolerated when treating life-threatening illnesses, such as tumors, that would not be tolerated when treating disorders of lesser consequence. The concentration of conjugate in the composition will depend on absorption, inactivation and excretion rates thereof, the dosage schedule, and amount administered as well as other factors known to those of skill in the art.

Preferably, the conjugate and complex are substantially pure. As used herein, "substantially pure" means sufficiently homogeneous to appear free of readily detectable impurities as determined by standard methods of analysis, such as thin layer chromatography (TLC), gel electrophoresis, high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

The conjugates and complexes may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The ophthalmic compositions may also include additional components, such as hyaluronic acid. The conjugates and complexes may be formulated as aerosols for topical application (see, e.g., U.S. Pat. Nos. 4,044,126, 4,414,209, and 4,364,923).

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions may also be suitable as pharmaceutically acceptable carriers. These may be prepared according to methods known to those skilled in the art.

Upon mixing or addition of the conjugate(s) with the vehicle, the resulting mixture may be a solution, suspension, emulsion or the like. The form of the resulting mixture depends upon a number of factors, including the intended mode of administration and the solubility of the conjugate in the selected carrier or vehicle. The effective concentration is sufficient for ameliorating the symptoms of the disease, disorder or condition treated and may be empirically determined based upon in vitro and/or in vivo data, such as the data from the mouse xenograft model for tumors or rabbit ophthalmic model. If necessary, pharmaceutically acceptable salts or other derivatives of the conjugates and complexes may be prepared.

The active materials can also be mixed with other active materials, that do not impair the desired action, or with materials that supplement the desired action, including viscoelastic materials, such as hyaluronic acid, which is sold under the trademark HEALON (solution of a high molecular weight (MW of about 3 millions) fraction of sodium hyaluronate; manufactured by Pharmacia, Inc. see, e.g., U.S. Pat. Nos. 5,292,362, 5,282,851, 5,273,056, 5,229,127, 4,517,295 and 4,328,803), VISCOAT (fluorine-containing (meth) acrylates, such as, 1H,1H,2H,2H-heptadecafluorodecylmethacrylate; see, e.g., U.S. Pat. Nos. 5,278,126, 5,273,751 and 5,214,080; commercially available from Alcon Surgical, Inc.), ORCOLON (see, e.g., U.S. Pat. Nos. 5,273,056; commercially available from Optical Radiation Corporation), methylcellulose, methyl hyaluronate, polyacrylamide and polymethacrylamide (see, e.g., U.S. Pat. No. 5,273,751). The viscoelastic materials are present generally in amounts ranging from about 0.5 to 5.0%, preferably 1 to 3% by weight of the conjugate material and serve to coat and protect the treated tissues. The compositions may also include a dye, such as methylene blue or other inert dye, so that the composition can be seen when injected into the eye or contacted with the surgical site during surgery.

The conjugates and complexes may be formulated for local or topical application, such as for topical application to the skin and mucous membranes, such as in the eye, in the form of gels, creams, and lotions and for application to the eye. Such solutions, particularly those intended for ophthalmic use, may be formulated as 0.01%–10% isotonic solutions, pH about 5–7, with appropriate salts. Suitable ophthalmic solutions are known (see, e.g., U.S. Pat. No. 5,116,868, which describes typical compositions of ophthalmic irrigation solutions and solutions for topical application). Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium β-hydroxybutyrate and 5–5.5 mM glucose.

The conjugates and complexes may be prepared with carriers that protect them against rapid elimination from the body, such as time release formulations or coatings. Such carriers include controlled release formulations, such as, but not limited to, implants and microencapsulated delivery systems, and biodegradable, biocompatible polymers, such as carboxymethylcellulose, ethylene vinyl acetate, polyanhydrides, polyglycolic acid, polyorthoesters, polylactic acid and others. For example, the composition may be applied during surgery using a sponge, such as a commercially available surgical sponges (see, e.g., U.S. Pat. Nos. 3,956,044 and 4,045,238; available from Weck, Alcon, and Mentor), that has been soaked in the composition and that releases the composition upon contact with the eye. These are particularly useful for application to the eye for ophthalmic indications following or during surgery in which only a single administration is possible. The compositions may also be applied in pellets (such as Elvax pellets—ethylene-vinyl acetate copolymer resin); about 1–5 μg of conjugate per 1 mg resin) that can be implanted in the eye during surgery.

If oral administration is desired, the conjugate should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The conjugates and complexes can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials that do not impair the desired action, or with materials that supplement the desired action, such as cisplatin for treatment of tumors.

Finally, the compounds may be packaged as articles of manufacture containing packaging material, one or more conjugates and complexes or compositions as provided herein within the packaging material, and a label that indicates the indication for which the conjugate is provided.

6. Administration

Typically a therapeutically effective dosage should produce a serum concentration of active ingredient of from about 0.1 ng/ml to about 500 µg/ml. The pharmaceutical compositions typically should provide a dosage of from about 0.01 mg/kg to about 100–2000 mg/kg of conjugate, depending upon the conjugate. Local application for ophthalmic disorders and dermatological disorders should provide about 1 ng up to 100 µg, preferably about 1 ng to about 10 µg, per single dosage administration. It is understood that the amount to administer will be a function of the conjugate selected, the indication treated, and possibly the side effects that will be tolerated.

Therapeutically effective concentrations and amounts may be determined for each application herein empirically by testing the conjugates and complexes in known in vitro and in vivo systems (e.g., murine, rat, rabbit, or baboon models), such as those described herein; dosages for humans or other animals may then be extrapolated therefrom. The rabbit eye model is a recognized model for studying the effects of topically and locally applied drugs (see, e.g., U.S. Pat. Nos. 5,288,735, 5,263,992, 5,262,178, 5,256,408, 5,252,319, 5,238,925, 5,165,952; see also Mirate et al., *Curr. Eye Res.* 1:491–493, 1981).

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

7. Therapeutic Sequences and Compositions

A therapeutic nucleotide composition of the present invention comprises a nucleotide sequence encoding a therapeutic molecule as described herein. As noted above, a therapeutic nucleotide composition may further comprise an enhancer element or a promoter located 5' to and controlling the expression of said therapeutic nucleotide sequence or gene. The promoter is a DNA segment that contains a DNA sequence that controls the expression of a gene located 3' or downstream of the promoter. The promoter is the DNA sequence to which RNA polymerase specifically binds and initiates RNA synthesis (transcription) of that gene, typically located 3' of the promoter.

The subject therapeutic nucleotide composition consists of a nucleic acid molecule that comprises at least 2 different operatively linked DNA segments. The DNA can be manipulated and amplified by PCR and by using the standard techniques described in *Molecular Cloning. A Laboratory Manual*, 2nd Edition, Maniatis et al., eds., Cold Spring Harbor, N.Y. (1989). Typically, to produce a therapeutic nucleotide composition of the present invention, the sequence encoding the selected therapeutic composition and the promoter or enhancer are operatively linked to a vector DNA molecule capable of autonomous replication in a cell either in vivo or in vitro. By operatively linking the enhancer element or promoter and the nucleotide sequence encoding the therapeutic nucleotide composition to the vector, the attached segments are replicated along with the vector sequences. Thus, a recombinant DNA molecule (rDNA) of the present invention is a hybrid DNA molecule comprising at least 2 nucleotide sequences not normally found together in nature.

The therapeutic nucleotide composition of the present invention is from about 20 base pairs to about 100,000 base pairs in length. Preferably the nucleic acid molecule is from about 50 base pairs to about 50,000 base pairs in length. More preferably the nucleic acid molecule is from about 50 base pairs to about 10,000 base pairs in length. Most preferred is a nucleic acid molecule from about 50 pairs to about 4,000 base pairs in length. The therapeutic nucleotide can be a gene or gene fragment that encodes a protein or peptide that provides the desired therapeutic effect such as replacement of alpha 1-antitrypsin or cystic fibrosis transmembrane regulator protein and the like. Alternatively, the therapeutic nucleotide can be a DNA or RNA oligonucleotide sequence that exhibits enzymatic therapeutic activity. Examples of the latter include antisense oligonucleotides that will inhibit the transcription of deleterious genes or ribozymes that act as site-specific ribonucleases for cleaving selected mutated gene sequences. In another variation, a therapeutic nucleotide sequence of the present invention may comprise a DNA construct capable of generating therapeutic nucleotide molecules, including ribozymes and antisense DNA, in high copy numbers in target cells, as described in published PCT application No. WO 92/06693 (the disclosure of which is incorporated herein by reference).

A regulatable promoter is a promoter where the rate of RNA polymerase binding and initiation is modulated by external stimuli. Such stimuli include compositions light, heat, stress and the like. Inducible, suppressible and repressible promoters are regulatable promoters. Regulatable promoters may also include tissue specific promoters. Tissue specific promoters direct the expression of that gene to a specific cell type. Tissue specific promoters cause the gene located 3' of it to be expressed predominantly, if not exclusively in the specific cells where the promoter expressed its endogenous gene. Typically, it appears that if a tissue-specific promoter expresses the gene located 3' of it at all, then it is expressed appropriately in the correct cell types as has been reviewed by Palmiter et al., *Ann. Rev. Genet*. 20: 465–499 (1986).

When a tissue specific promoter controls the expression of a gene, that gene will be expressed in a small number of tissues or cell types rather than in substantially all tissues and cell types. Examples of tissue specific promoters include the immunoglobulin promoter described by Brinster et al., *Nature* 306: 332–336 (1983) and Storb et al., *Nature* 310: 238–231 (1984); the elastase-I promoter described by Swift et al., *Cell* 38: 639–646 (1984); the globin promoter described by Townes et al., *Mol. Cell. Biol.* 5: 1977–1983 (1985), and Magram et al., *Mol. Cell. Biol.* 9: 4581–4584 (1989), the insulin promoter described by Bucchini et al., *PNAS USA* 83: 2511–2515 (1986) and Edwards et al., *Cell* 58: 161 (1989); the immunoglobulin promoter described by Ruscon et al., *Nature* 314: 330–334 (1985) and Grosscheld et al., *Cell* 38: 647–658 (1984); the alpha actin promoter described by Shani, *Mol. Cell. Biol.* 6: 2624–2631 (1986); the alpha crystalline promoter described by Overbeek et al., *PNAS USA* 82: 7815–7819 (1985); the prolactin promoter described by Crenshaw et al., *Genes and Development* 3: 959–972 (1989); the proopiomelanocortin promoter described by Tremblay et al., *PNAS USA* 85: 8890–8894 (1988); the beta-thyroid stimulating hormone (BTSH) promoter described by Tatsumi et al., *Nippon Rinsho* 47: 2213–2220 (1989); the mouse mammary tumor virus (MMTV) promoter described by Muller et al., *Cell* 54: 105 (1988); the albumin promoter described by Palmiter et al., *Ann. Rev. Genet*. 20: 465–499 (1986); the keratin promoter described by Vassar et al., *PNAS USA* 86: 8565–8569 (1989); the osteonectin promoter described by McVey et al., *J. Biol. Chem.* 263: 11,111–11,116 (1988); the prostate-specific promoter described by Allison et al., *Mol. Cell. Biol.* 9: 2254–2257 (1989); the opsin promoter described by Nathans et al., *PNAS USA* 81: 4851–4855 (1984); the olfactory marker protein promoter described by Danciger et al., *PNAS USA* 86: 8565–8569 (1989); the neuron-specific enolase (NSE) promoter described by Forss-Pelter et al., *J. Neurosci. Res.* 16: 141–151 (1986); the L-7 promoter described by Sutcliffe, *Trends in Genetics* 3: 73–76 (1987) and the protamine 1 promoter described Peschon et al., *Ann. New York Acad. Sci*. 564: 186–197 (1989) and Braun et al., *Genes and Development* 3: 793–802 (1989).

In various alternative embodiments of the present invention, therapeutic sequences and compositions useful for practicing the therapeutic methods described herein are contemplated. Therapeutic compositions of the present invention may contain a physiologically tolerable carrier together with one or more therapeutic nucleotide sequences of this invention, dissolved or dispersed therein as an active ingredient. In a preferred embodiment, the composition is not immunogenic or otherwise able to cause undesirable side effects when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

Compositions designed to preferentially target non-epithelial cells may include an adenovirus-derived protein-ligand conjugate and a therapeutic nucleotide sequence. Examples of useful ligands directed to specific receptors (identified in parentheses) include FGF and related ligands (FGFR); the V3 loop of HIV gp120 (CD4); transferrin (transferrin receptor); LDL (LDL receptors); and deglycosylated proteins (asialoglycoprotein receptor). Polypeptides having a sequence that includes an amino acid residue sequence selected from the group comprising— EDPGFFNVE- (SEQ ID NO: 5) and -EDPGKQLYNVE- (SEQ ID NO: 6) are capable of targeting receptors such as the CR2 receptor, and are thus useful in compositions disclosed herein.

Useful ligands also include antibodies and attachment sequences, as well as receptors themselves. Antibodies to cell receptor molecules such as integrins and the like, MHC Class I and Class II, asialoglycoprotein receptor, transferrin receptors, LDL receptors, CD4, and CR2 are but a few useful according to the present invention. It is also understood that the ligands typically bound by receptors, as well as analogs to those ligands, may be used as cellular targeting agents as disclosed herein.

Exemplary and preferred nucleotide sequences encode an expressible peptide, polypeptide or protein, and may further include an active constitutive or inducible promoter sequence. For example, preferred therapeutic nucleotide sequences according to the present invention are capable of delivering HIV antisense nucleotides to latently-infected T cells via CD4. Similarly, delivery of Epstein-Barr Virus (EBV) EBNa-1 antisense nucleotides to B cells via CR2 is capable of effecting therapeutic results.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified, or formulated into suppositories, ointments, creams, dermal patches, or the like, depending on the desired route of administration.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof, including vegetable oils, propylene glycol, polyethylene glycol and benzyl alcohol (for injection or liquid preparations); and vaseline, vegetable oil, animal fat and polyethylene glycol (for externally applicable preparations). In addition, if desired, the composition can contain wetting or emulsifying agents, isotonic agents, dissolution promoting agents, stabilizers, colorants, antiseptic agents, soothing agents and the like additives (as usual auxiliary additives to pharmaceutical preparations), pH buffering agents and the like which enhance the effectiveness of the active ingredient.

The therapeutic compositions of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

A therapeutic composition typically contains an amount of a therapeutic nucleotide sequence of the present invention sufficient to deliver a therapeutically effective amount to the target tissue, typically an amount of at least 0.1 weight percent to about 90 weight percent of therapeutic nucleotide sequence per weight of total therapeutic composition. A weight percent is a ratio by weight of therapeutic nucleotide sequence to total composition. Thus, for example, 0.1 weight percent is 0.1 grams of DNA segment per 100 grams of total composition.

The therapeutic nucleotide compositions comprising synthetic oligonucleotide sequences of the present invention can be prepared using any suitable method, such as, the phosphotriester or phosphodiester methods. See Narang et al., *Meth. Enzymol.* 68: 90, (1979); U.S. Pat. No. 4,356,270; and Brown et al., *Meth. Enzymol.* 68 :109, (1979). For therapeutic oligonucleotides sequence compositions in which a family of variants is preferred, the synthesis of the family members can be conducted simultaneously in a single reaction vessel, or can be synthesized independently and later admixed in preselected molar ratios.

For simultaneous synthesis, the nucleotide residues that are conserved at preselected positions of the sequence of the family member can be introduced in a chemical synthesis protocol simultaneously to the variants by the addition of a single preselected nucleotide precursor to the solid phase oligonucleotide reaction admixture when that position number of the oligonucleotide is being chemically added to the growing oligonucleotide polymer. The addition of nucleotide residues to those positions in the sequence that vary can be introduced simultaneously by the addition of amounts, preferably equimolar amounts, of multiple preselected nucleotide precursors to the solid phase oligonucleotide reaction admixture during chemical synthesis. For example, where all four possible natural nucleotides (A,T,G and C) are to be added at a preselected position, their precursors are added to the oligonucleotide synthesis reaction at that step to simultaneously form four variants.

This manner of simultaneous synthesis of a family of related oligonucleotides has been previously described for the preparation of "degenerate oligonucleotides" by Ausubel et al, in *Current Protocols in Molecular Biology, Suppl.* 8, p.2.11.7, John Wiley & Sons, Inc., New York (1991), and can readily be applied to the preparation of the therapeutic oligonucleotide compositions described herein.

Nucleotide bases other than the common four nucleotides (A,T,G or C), or the RNA equivalent nucleotide uracil (U), can be used in the present invention. For example, it is well known that inosine (I) is capable of hybridizing with A, T and G, but not C. Thus, where all four common nucleotides are to occupy a single position of a family of oligonucleotides, that is, where the preselected therapeutic nucleotide composition is designed to contain oligonucleotides that can hybridize to four sequences that vary at one position, several different oligonucleotide structures are contemplated. The composition can contain four members, where a preselected position contains A,T,G or C. Alternatively, the composition can contain two members, where a preselected position contains I or C, and has the capacity the hybridize at that position to all four possible common nucleotides. Finally, other nucleotides may be included at the preselected position that have the capacity to hybridize in a non-destabilizing manner with more than one of the common nucleotides in a manner similar to inosine.

8. Testing of Constructs

The reprogrammed viral delivery vehicles may be assessed in any number of in vitro model systems. In particular, target cells are grown in culture and incubated with the nucleic acid delivery vehicle. The nucleic acid can encode a reporter, in which case, the reporter product is assayed, or encode a cytocidal product, in which case cell killing is measured. Moreover, any assayable gene product can be used. For reporter genes, a wide variety of suitable genes are available. Such reporters include β-galactosidase, alkaline phosphatse, β-glucuronidase, large T antigen, any protein for which an antibody exists or can be developed. The choice of a reporter depends, in part, upon the cells being tested. Alternatively, the nucleic acid can encode a cytocidal product. Such products include all those described herein.

The delivery vehicles may be assessed in in vivo model systems. Generally, a xenogeneic tumor model system will be used, but other tumor model systems are useful as well. In the xenogeneic system, an immunodeficient mouse, or other immunodeficient animal, is injected with tumor cells, such as human tumor cells. The nucleic acid delivery vehicle is administered and tumor growth is monitored. Any reduction of tumor growth is useful within the context of this invention.

The following examples are included for illustrative purposes only and are not intended to limit the scope of the invention.

EXAMPLES

Example 1

Targeted Gene Delivery to Kaposi's Sarcoma Cells

Infection with human immunodeficiency virus (HIV) is associated with an increased incidence of a characteristic subset of neoplastic disorders including Kaposi's sarcoma (KS) and non-Hodgkin's lymphoma (Conant, *Recent Results in Cancer Research* 139:423–32 (1995)). In this regard, KS is the major AIDS-associated malignancy and leads to significant morbidity (Conant, Id. (1995); Northfelt and Volberding, *Advances in Oncology* 7:9–17 (1991)). Effective treatment for KS is currently lacking, with the duration of survival being only 9.9 months with some newer experimental protocols (Gill, et al., *J. Clin. Oncol.* 14:2353–64 (1996)). thus, the development of novel, more effective therapies is required for HIV-associated KS.

Toward this end, various of gene therapy approaches have been developed for neoplastic diseases (Ross, et al., *Hum. Gene Ther.* 7:1781–90 (1996)). Practical implementation of a gene therapy approach for KS would require efficient in vivo transduction of the tumor cells, Further, some level of targeting to KS spindle cells would likewise be an important criterion for vector selection. This consideration is especially relevant in AIDS-related disseminated KS, as this tumor is thought to arise from vascular endothelial cells that are continuous with the systemic vasculature (Northfelt et al., Id. (1991)). Further complicating this endeavor, if has previously been noted that KS cells are refractory to transduction by a variety of viral and non-viral vector systems, thus limiting even those gene therapy approaches based on loco-regional gene delivery. To address this issue, a derivative vector has now been developed which possesses the capacity to target KS cells and is further described hereinbelow.

A. Materials and Methods

1. Cell Lines

The human AIDS-KS cell line KSY-1 (Lunardi-Iskandar, et al., *J. Natl. Cancer Inst.* 87:974–981 (1995)), RW376, and CVU-1 were obtained for use as described herein. KS-SLK (Siegal, et al., *Cancer* 65:492–498 (1990)) was derived from an oral KS lesion in an immunosuppressed patient and was also obtained for use as described below.

All cell lines are grown in Dulbecco's Modified Eagle s Medium/Ham s F12 at 1:1 ratio by weight (DMEM/F12 Cellgro Mediatech, Washington, D.C.)+10% fetal bovine serum (FBS, Hyclone, Logan, Utah)+2 mM glutamine (Cellgro Mediatech)+penicillin/streptomycin (Cellgro Mediatech) at 37° C. in 5% $CO_2$ (CM). Media changes are performed every 3–4 days. Cells are passaged using Trypsin/EDTA (Cellgro Mediatech) when cells achieved confluency. Viability is determined in confluent cells exposed to trypsin/EDTA, centrifuged at 800×g in the presence of CM, and counted using a hemocytometer after trypan blue exclusion. Ganciclovir (GCV; Cytovene) is purchased from Hoffman Laboratories (Nutley, N.J.). Tissue culture plates and flasks were manufactured by Nunclon (Denmark).

2. Anti-Knob Antibodies and Fragments

The procedures for generating and purifying exemplary antibodies and fragments as disclosed herein are described in a variety of references known to those of skill in the art (e.g., Douglas, et al., *Nature Biotech.* 14:1574–1578 (1996)). In general, the procedures may be described as follows.

To develop a neutralizing anti-knob mAb, hybridomas are generated by standard techniques after immunization of mice with intact Ad5 followed by two rounds of immunization with purified Ad5 knob (native or recombinant). On the basis of its high affinity binding to recombinant Ad5 knob and its ability to neutralize Ad5 infection of HeLa cells (data not shown), one clone, designated 1D6.14, was chosen for further study and the mAb is purified from ascites fluid by affinity chromatography using an immobilized protein A column.

Anti-knob mAbs are generated by established methods (see, e.g., Harlow and Lane, *Antibodies, a Laboratory Manual*, Cold Spring Harbor Laboratory, NY (1988)) after immunization of BALB/c mice with Ad5, followed by two rounds of immunization with purified recombinant Ad5 knob (see Henry, et al., *J. Virol.* 68:5239–46 (1994)). Sensitized lymphocytes are fused with P3-X63-Ag8.653 cells. The reactivity of the hybridoma supernatants with trimeric Ad5 knob is determined in an ELISA. The ability of the hybridoma supernatants to neutralize Ad5 infection is assayed by endpoint CPE.

The 1D6.14 hybridoma cells are injected into BALB/c mice and ascites fluid collected (Harlow and Lane, Id. (1988)). Purification of the mAb is performed by affinity chromatography on immobilized protein A using an ImmunoPure IgG purification kit (Pierce, Rockford, Ill.). Fab fragments are prepared and purified by digestion of 1D6.14 on immobilized papain followed by affinity chromatography on immobilized protein A, using an ImmunoPure Fab purification kit (Pierce). After extensive dialysis against phosphate-buffered saline (PBS), the concentrations of the purified mAb and Fab fragment are determined using the Bio-Rad protein assay (Bio-Rad, Hercules, Calif.).

For the purposes of developing a targeted adenoviral vector by immunological methods, it would be preferable to use the Fab fragment of the antibody, rather than the intact immunoglobulin. By using the Fab fragment, the two antigen-binding arms of the parent antibody might be prevented from crosslinking different viruses to form large complexes that might prove refractory to cellular uptake. Intact 1D6.14 is digested with papain and the Fab fragments are purified. Both the parent antibody, 1D6.14, and the Fab fragment are capable of neutralizing adenovirus infection in a dose-dependent manner, whereas a control antibody failed to block infection. (See Douglas et al., Id. (1996).)

3. Recombinant Adenovirus

Recombinant E1A-deleted adenovirus (Herz and Gerard, *PNAS USA* 90:2812–1216 (1993)) expressing firefly luciferase (AdCMV-Luc) is utilized as described hereinbelow. An E1-deleted Ad5 vector expressing the CMV-driven herpes simplex thymidine kinase gene (AdCMVHSVtk) is constructed using homologous recombination techniques, as previously reported (Rosenfeld et al. *Clin. Cancer Res.* 1:1571–1589 (1995)). An E1-deleted recombinant adenovirus expressing an enhanced variant of green fluorescent protein (AdCAG-GFPS65T) is also used and has been described previously (Moriyoshi et al., *Neuron* 16:255–260 (1996)).

Recombinant adenoviruses are propagated on the permissive 293 cell line, purified using a cesium chloride gradient, and subsequently plaque titered on 293 cells employing standard methods (Graham and Prevec, in *Methods in Mol. Biol. 7: Gene Transfer and Expression Techniques*, Murray and Walker (eds.), Humana Press, Clifton, 1991, pp. 109–129). Virus stocks are stored frozen at −80° C. until use.

4. Fab-FGF2 Molecular Coniugate

The Fab-FGF2 conjugate is constructed by linking modified recombinant basic fibroblast growth factor (FGF2–3; Sosnowski, et al., *J. Biol. Chem.* 271:33647–33653 (1996)) with the Fab fragment from a blocking monoclonal antibody, 1D6.14, which was generated against adenovirus type 5 (Ad5) knob region (Douglas, et al., *Nature Biotech.* 14:1574–1578 (1996)). For conjugation, the Fab is derivatized with the heterobifunctional crosslinking reagent S-2-pyridyl disulfide (SPDP; Pharmacia, Uppsala, Sweden) at a 1:3 molar ratio and incubated at room temperature for 30 minutes to yield a modified Fab fragment (PDP-Fab).

The PDP-Fab is dialyzed to remove unbound linker. Purified FGF2 is generated as previously described (Sosnowski et al., Id. (1996)), then reduced and mixed at a 2:1 molar ratio with PDP-Fab, and incubated at 4° C. for 16 hrs with shaking.

In general, FGF2 is prepared and reduced as follows. A 155-amino-acid human FGF2, in which the cysteine at position 96 is mutagenized to serine (Lappi, D. A., Matsunami, R., Martineau, D., and Baird, A. (1993) *Anal. Biochem.* 212.446–451), may be used as described in the present invention. It should be appreciated that this molecule is described as exemplary, and not as a limitation; other variants of FGF and polypeptides reactive with the FGF receptor complex are useful according to the present invention.

FGF2 is expressed in *E. coli*, and purified to homogeneity by conventional chromatography techniques. FGF2 (C96S; may also be referred to herein as FGF2-3) is adjusted to pH 7.0 by adding Tris-base. FGF2 is then reduced by adding MTG to a final concentration of 20 mM. The reaction is allowed to incubate at room temperature for 30 minutes. Excess MTG is removed by passing FGF2 (C96S) over a PD-10 column (Pharmacia). Running buffer is 10 mM NaOAc/HOAc pH 5.4 containing 0.14 M NaCl, 1 mM EDTA.

The Fab is thiolated essentially as follows. 1.6 mg of Fab is dialyzed against NaPO4 (0.1 M Sodium Phosphate buffer, pH 7.5 containing 0.1 M NaCl and 1.0 mM EDTA) at 1:250 (v/v) for 3 hr with 2 changes of buffer. The dialyzed Fab fragment is centrifuged at 14,000 rpm (Eppendorf centrifuge 5415C) for 10 minutes and the supernatant collected. The Fab fragment is derivitized with SPDP (Pharmacia), (SPDP dissolved in ethanol), at a molar ratio of 1:3 for 30 minutes at room temperature with occasional stirring. The excess SPDP and low molecular weight reaction products are removed by dialysis against the buffer described above at 1:500 (v/v).

Conjugation of FGF2 and the Fab is carried out essentially as follows. FGF2 and PDP-Fab are mixed at a molar ratio of 2:1 at pH 7.5 and incubated at 4 C for 16 hours with shaking. An aliquot of the reaction mixture is analysed by SEC-HPLC. The conjugate is purified over a Heparin-Sepharose column (1 ml Heparin Hi-Trap, Pharmacia) to remove unconjugated Fab fragment. The material is loaded onto the column in 10 mM Tris pH 7.4 and washed in the same buffer plus 0.6 M NaCl. When the absorbance returns to background the conjugate is eluted from the column in the same buffer containing 2 M NaCl. An aliquot of the 2M eluate is analyzed by SEC-HPLC. The 2M eluate is loaded onto Sephacryl S-100 to remove free FGF2 and buffer exchanged into PBS, pH 7.4. Fractions 17–26 are pooled as final purified Fab-FGF2 material.

The conjugation reaction is monitored by reducing an aliquot of the reaction mixture with DTT and monitoring the absorbance of PDP at 343 nM. Purified Fab-FGF2, FGF2 and Fab are analyzed by SDS-PAGE (12%) and by Western analysis using an antibody generated against FGF2. To determine if conjugation to the Fab interfered with FGF2's ability to bind to the receptor and stimulate proliferation, the material is assayed in an endothelial proliferation assay. Bovine aortic endothelial cells are seeded at 1000 cells/well on a 24 well flat-bottom tissue culture plate in DMEM (Biowhittaker), 10% FCS (Hyclone), 50 mg/ml Gentamycin (JRH Biosciences), and 2 mM L-glutamine (Biowhittaker). The following day serial dilutions of FGF2 and Fab-FGF2 ranging from 6 ng/ml to 10 pg/ml, are added to the wells in triplicate. After 48 hours the media is removed and 1.5 mls of fresh media containing the same concentrations of FGF2 and Fab-FGF2 are added to the cells. Following another 72 hours of incubation the media is removed, the cells are washed with PBS and then harvested with 0.25% trypsin. The trypsinized cells are counted using a Coulter Counter. The results of the proliferation assay reveal that conjugation of the Fab fragment to FGF2 did not interfere with FGF2's ability to bind to its receptor and stimulate proliferation.

The conjugate is purified over a heparin-Sepharose column (Pharmacia) by loading in 10 mM Tris HCl, pH 7.4, washing with 10 mM Tris HCl/0.6 mM NaCl, pH 7.4 and eluting in 10 mM Tris HCl/2M NaCl, pH 7.4. The eluant is separated over a Sephacryl S-100 column equilibrated with Dulbecco s phosphate-buffered saline (PBS, pH 7.4) to remove excess salt and unconjugated protein. The presence of PDP in the conjugate is confirmed by reducing an aliquot of the conjugate and measuring the absorbance of PDP (342 nanometers). The size and activity of the conjugate is subsequently analyzed by western blot (Immunoblotting, in *Antibodies: A Laboratory Manual*, Chapter 12, Harlow and Lane (eds.), Cold Spring Harbor Laboratory (1988)) and enzyme-linked immunoassay (ELISA) analysis (see Immunoassays, in *Antibodies: A Laboratory Manual*, Chapter 14, Harlow and Lane (eds.), Cold Spring Harbor Laboratory (1988)).

5. Adenovirus Infection Assays

To assess adenoviral transduction, 24,000 cells of each KS cell line are plated in triplicate into each well of a 12-well plate in the presence of 1 ml of CM. The cells are incubated overnight to allow cells to adhere. Infection complexes are mixed in a final volume of 50 ul containing: (1) adenovirus (AdCMV-Luc or Ad-CAG-GFPS65T) at 50 plaque forming units (pfu)/cell; (2) adenovirus+Fab-FGF2 conjugate; (3) adenovirus+Fab; or (4) adenovirus+Fab-FGF2 conjugate+anti-FGF2 antisera (Sigma), 16 ul. The complexes are incubated in 1.5 ml of polypropylene tubes at 27° C. for 30 minutes. The mixtures are then diluted in DMEM/F12+2% FBS and added to each well in a volume of 200 ul. The cells are incubated at 37° C. in 5% $CO_2$ for 1 hr, then 800 ul of DMEM/F12+10% FBS is added to each well. Twenty-four hours after the addition of virus, the cells are rinsed with PBS and assayed for luciferase activity or analyzed by fluorescence activated cell sorting (FACS). For all luciferase assays, the cells are lysed in 200 ul of Promega (Madison, Wis.) lysis buffer. Twenty ul of each sample is subsequently mixed with 100 ul of Promega luciferase assay reagent according to manufacturer s instructions and triplicate determinations of duplicate samples are assayed in a Berthold luminometer.

To assess AdCMVHSVtk-mediated killing, $1\times10^5$ KSY-1 or KS-SLK cells are plated in duplicate in 6-well plates in 2 ml of CM. The cells are incubated at 37° C. in 5% $CO_2$ overnight. The medium is aspirated and infection mixtures containing 5 pfu/cell of either: (1) AdCMVHSVtk, (2) AdCMVHSVtk+Fab, or (3) AdCMVHSVtk+Fab-FGF2 conjugate are added to each well in a volume of 500 ul of DMEM/F12+2% FBS. After 1 hr incubation at 37° C. in 5% $CO_2$, 1.5 ml of CM is added. The cells are incubated for an additional 24 hours and the medium is then aspirated and replaced with CM in the absence (–GCV) or presence (+GCV) of 20 uM GCV. The medium is changed after 3 days and cell counting is performed in triplicate for each of the duplicate wells 6 days after exposure to adenovirus to assess TK/GCV-mediated killing.

6. Immunocytochemistry

KS cells ($2\times10^4$/well) are plated into replicate wells of a 24-well tissue culture plate in CM and incubated at 37° C. on 5% $CO_2$ for 48 hrs. The cells are rinsed and endogenous peroxidase is blocked with 1% $H_2O_2$/methanol for 30 minutes. The cells are then rinsed and blocked in 3% bovine serum albumin (BSA; Fraction V, Boehringer Mannheim, Germany)/PBS for 1 hour at 27° C. Rabbit anti-fibroblast growth factor receptor antiserum (FGFR1- and FGFR2-reactive; Upstate Biotechnologies, Inc., Lake Placid, N.Y.) or control rabbit IgG (Vector; Burlingame, Calif.) is diluted 1:400 in 3% BSA/PBS and allowed to incubate on cells for 1 hour at 37° C. The cells are rinsed and stained with diaminobenzidine (Sigma)using a Vectastain rabbit horseradish peroxidase kit according to the manufacturer's instructions. The cells are rinsed and stored under water until photomicrographs are taken.

7. Statistical Analysis

A comparison of individual conditions is assessed using Students t-test for equal means. Statex 1.2 for Macintosh software (Dinan Software, Clinton, Iowa) is used to facilitate the analysis.

B. Results and Discussion

Gene therapy approaches for KS will depend upon one's ability to accomplish efficient gene delivery to tumor cells in situ. In this regard, adenoviral vectors have been employed for a variety of in vivo cancer therapy applications. For this application, adenoviral vectors have the advantage of systemic ability and high levels of gene expression in vivo.

Prior to modifying the adenovirus so that it would selectively re-target KS cells, the native transduction efficiency of the Ad is examined. In relevant experiments, two AIDS-KS cell lines (KSY-1 and RW376), one KS cell line from an immunosuppressed patient (KS-SLK), and one classical KS cell line (CVU-1) are employed. In the first set of experiments, the adenoviral transduction of each cell line is determined by infecting each cell line with AdCMV-Luc in the presence or absence of the anti-adenovirus knob Fab (see FIG. 1) and subsequently measuring luciferase activity 24 hours after infection.

FIG. 1 shows a comparison of AdCMV-Luc transduction for four KS cell lines. KS cells are incubated with recombinant adenovirus expressing luciferase in the absence or presence of a Fab fragment blocking adenoviral knob-mediated infection. Experiments are performed in triplicate. Relative light units (RLU) are shown on the vertical axis; across the horizontal axis, the following cell lines are indicated: KSY-1; RW376; KS-SLK; and CVU-1. The open (colorless) bar represents AdCMV-Luc, while the closed (dark) bar represents AdCMV-Luc+anti-knob Fab.

Of the cell lines tested, KSY-1 and KS-SLK are poorly transducible by adenovirus, yielding $<10^6$ relative light units (RLU) per assay. The KS cell line CVU-1 is moderately transducible ($1.83 \times 10^6 \pm 1.15 \times 10^5$ RLU per assay), whereas the RWE376 cell line is highly transducible, yielding luciferase readings of $2.88 \times 10^6 \pm 5.4 \times 10^4$ RLU per assay.

The luciferase activity obtained after transduction using AdCMV-Luc correlated with FACS analysis data obtained from cells that are infected with AdCAG-GFPS65T. In this context, by FACS analysis of the KS cell lines transduced with 100 pfu per cell of AdCAG-GFPS65T, fewer than 1% of KSY-1 and KS-SLK cells are transducible. The CVU-1 and TW376 KS cell lines are significantly more transducible yielding 12% and 99% transduction efficiencies, respectively. In three cell lines—KSY-1, RW376, and KS-SLK—an anti-adenoviral knob Fab blocked AdCMV-Luc transduction by >50% ($p<0.01$). The CVU-1 cell line exhibited a less dramatic (20%)—albeit statistically significant ($p<0.05$)—block in adenoviral transduction. This low level of inhibition correlates with the modest level of transduction efficiency by the native adenovirus. This suggests that the degree to which these cells are refractory inversely correlates with knob-dependent cell binding.

Based on this recognition, it is hypothesized that this limitation to infection might be overcome using other cellular entry pathways to achieve effective gene transfer. In this regard, an immunological approach has now been developed that allows retargeting of adenoviral vectors to heterologous cellular pathways (see Douglas et al., Id. (1996)). As an initial validating step in these studies, we sought to determine whether KS cells expressed FGFR, and whether this receptor could serve as a potential substrate for retargeting.

First, immunocytochemistry is performed on the four KS cell lines using a polyclonal antibody that simultaneously recognizes FGFR-1 and FGFR-2 via a common epitope. FGFR immunocytochemical reactivity of the four KS cell lines utilized as described herein is assessed. KSY-1 (A,B), RW376 (C,D), KS-SLK (E,F) and CVU-1 (G,H) cell lines are stained with polyclonal antiserum raised against a peptide common to FGFR-1 and FGFR-2 or with non-immune control. Immunoreactivity is observed in all four cell lines (data not shown) as well as in mouse fibroblasts (positive control; not shown). Distribution of immunoreactivity is predominantly nuclear with scattered cell membrane staining in all four KS cell lines. The RW376 human KS cell line appeared to have the highest degree of membrane staining, while the CVU-1 KS line had dense nuclear immunoreactivity (data not shown). These studies demonstrate that FGFR is highly expressed in the relevant human KS cell lines, consistent with previous reports (Li, et al., *Cancer* 72:2253–9 (1993)).

Once a biologic rationale for the within-described vector retargeting approach is established, the efficacy of FGFR-targeted adenovirus is then tested using the KS cells as substrates. In a third set of experiments, we sought to determine whether we could immunologically retarget the adenovirus to FGFR using the Fab as a handle to the viral knob. To accomplish the retargeting between FGF receptor and the adenovirus-Fab complex (or conjugate), fibroblast growth factor (FGF2) is used as the targeting moiety, since it binds with high affinity to both FGFR-1 and FGFR-2 and could readily be covalently conjugated to the Fab. Toward this end, a covalent conjugate is synthesized using SDPD to form a disulfide bond between the Fab and the cysteine present on modified FGF2. Western blot analysis confirmed that the majority of the Fab-FGF2 conjugate contained a single FGF2 molecule and a single Fab fragment. In addition, ELISA-based binding studies confirmed that the conjugate simultaneously retained knob-binding activity and FDGF2 immunoreactivity (data not shown).

To assess whether the Fab-FGF2 conjugate could retarget the adenovirus to KS cells, the conjugate is first pre-incubated with AdCMV-Luc prior to cellular transduction. In an additional reaction mixture, the AdCMV-Luc+Fab-FGF2 mixture is further incubated with blocking antisera raised against FGFs to assess whether retargeting is occurring via the FGF2 moiety of the Fab-FGF2 conjugate. FIG. 3 illustrates the results of the AdCMV-Luc retargeting experiments using the Fab-FGF2 conjugate as well as the FGF2 blocking experiments.

FIG. 3 shows the enhanced AdCMV-Luc infectivity of KS cell lines by Fab-FGF2 conjugate. The enhanced infectivity of the Ad-conjugate complex is assessed in the presence and absence of anti-FGF2 antisera. Relative light units (RLU) are plotted on the vertical axis, while the relevant KS cell lines—KSY-1, RW376, KS-SLK, and CVU-1—are indicated on the horizontal axis. The closed bars represent AdCMV-Luc; stippled bars represent AdCMV-Luc+Fab-FGF2; and the open (colorless) bars represent AdCMV-Luc+Fab-FGF2+anti-FGF2 antisera.

The results shown in FIG. 3 demonstrate a dramatic enhancement of AdCMV-Luc transduction in all four KS cell lines when the adenovirus is pre-mixed with the Fab-FGF2 conjugate. This unexpected enhancement is statistically significant for all four cell lines ($p<0.001$) and represents a 44-fold increase in transduction for the KSY-1 cells and a 7.7-fold increase for RW376 cells. Of further note, addition of antisera raised against FGF2 blocked ($p<0.01$) the ability of the Fab-FGF2 conjugate to enhance AdCMV-Luc transduction in all four KS cell lines. The attenuation of conjugate-mediated adenovirus transduction by anti-FGF2 antisera confirmed that retargeting is occurring via the FGF portion of the conjugate.

The experiments conducted to date demonstrated that the low transduction efficiency of the adenovirus accomplished in KS cells could be overcome by retargeting the adenovirus to the FGFR pathway. The detection of increased luciferase activity confirmed that the transgene expression had taken place.

In an effort to confirm that this paradigm had utility in the context of a gene therapy approach whereby a toxin gene is introduced into KS cells, we performed a series of experiments using a recombinant adenovirus encoding the conditionally toxic gene product, herpes simplex thymidine kinase (AdCMVHSVtk). In this experiment, we chose the two cell lines that had demonstrated the highest resistance to adenoviral gene transfer, KSY-1 and KS-SLK. Dose-response killing curves for these two cell lines are generated using cells infected with various concentrations of AdMCHSVtk (data not shown) and subsequently maintained in the presence or absence of GCV. These experiments demonstrated that both cell lines showed little evidence of cell killing when cells are infected with 5 pfu/cell of AdCMVHSVtk in the presence of GCV.

Figure 4:
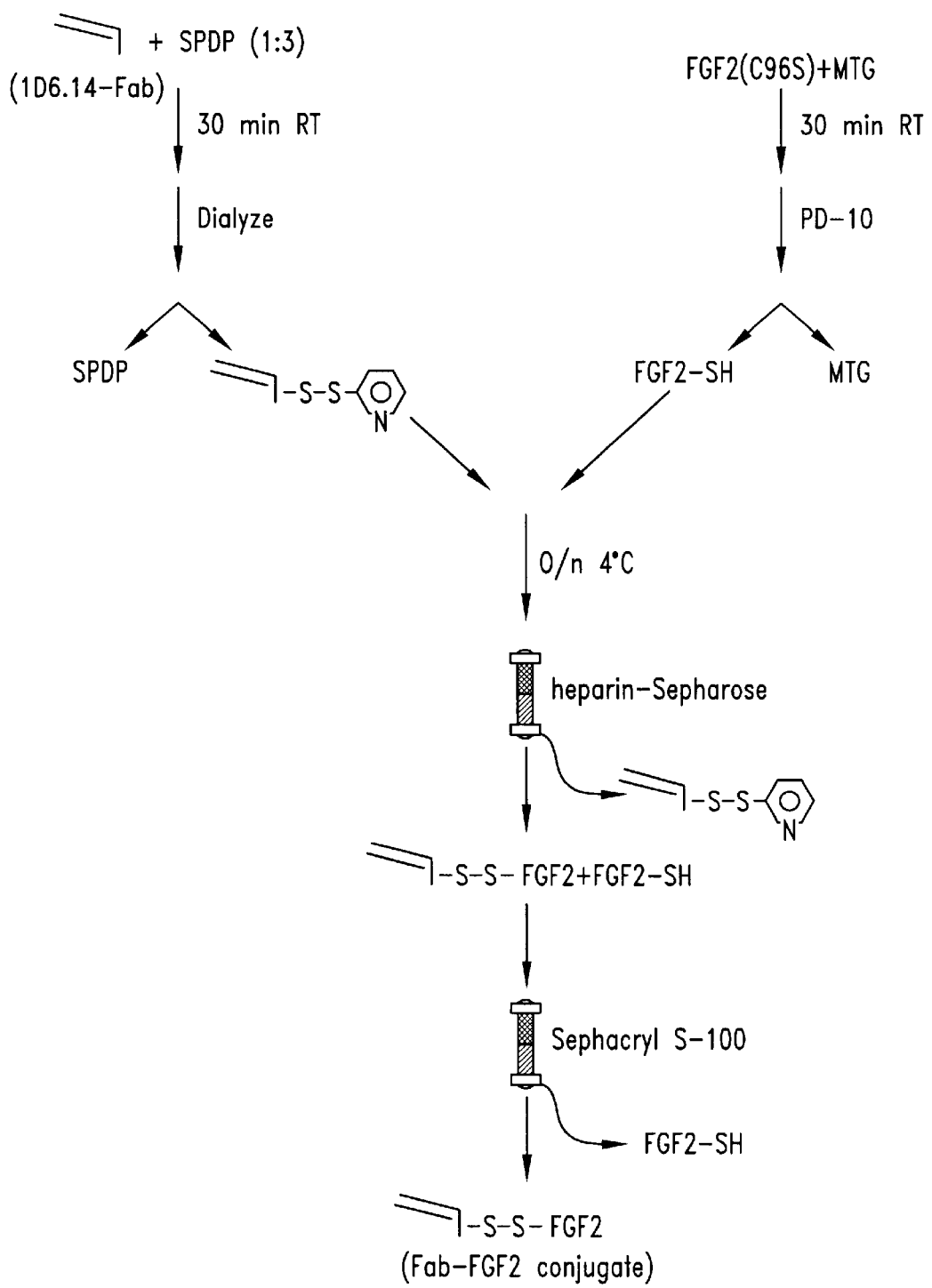
FIG. 4 illustrates a schema for the synthesis and purification of the Fab-FGF2 conjugate. It should be expressly understood that this schema may be applied to the synthesis and purification of any Fab-ligand conjugate and is thus not limited to the one illustrated.

In subsequent experiments, we sought to potentiate AdCMVHSVtk gene transduction and subsequent sensitization to GCV in KS cells by addition of the Fab-FGF2 conjugate. In the experimental design, cells are treated with 5 pfu of either AdCMVHSVtk or AdCMVHSVtk complexed with Fab-FGF2. GCV-mediated killing is assessed by maintaining cells in the presence or absence of GCV. The results of these experiments are shown in FIG. 4.

Figure 3A:
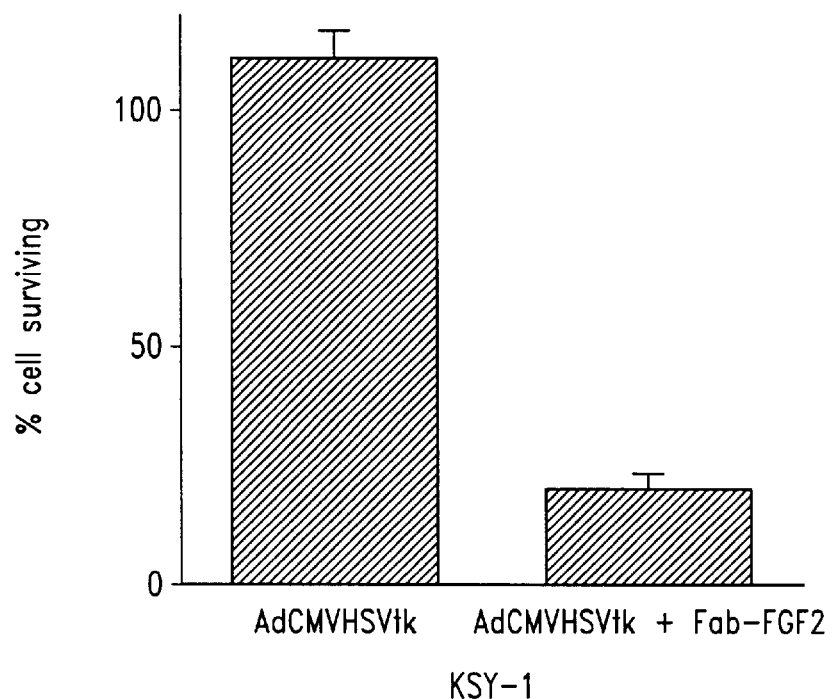
In FIG. 3A, KSY-1 cells transfected with AdCMVHSVtk or AdCMVHSVtk+Fab-FGF2 are identified on the horizontal axis.
Figure 3B:
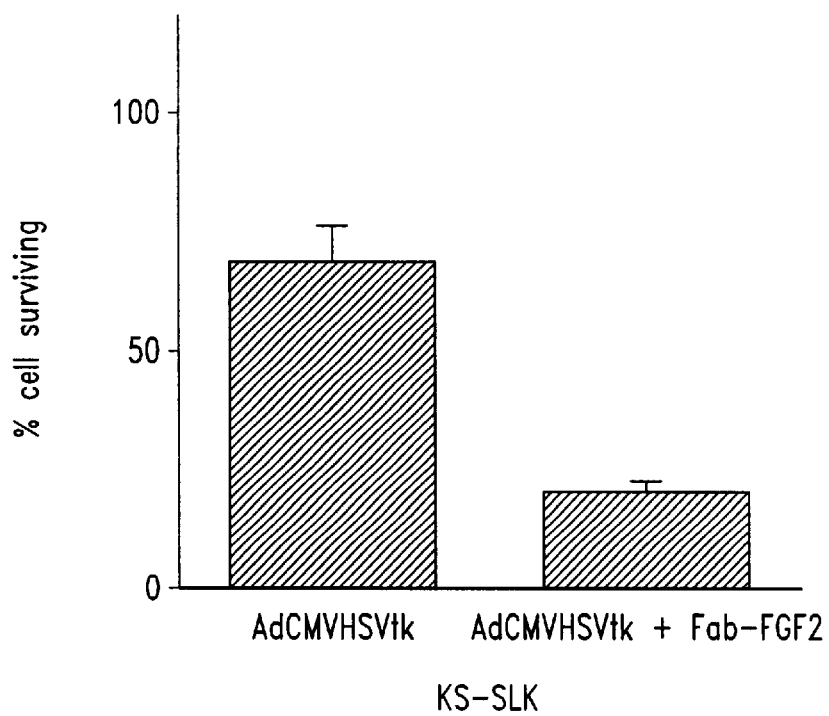
In FIG. 3B, KS-SLK cells transfected with AdCMVHSVtk or AdCMVHSVtk+Fab-FGF2 are identified on the horizontal axis.

FIG. 3 illustrates enhanced AdCMVHSVtk/GCV cell killing in KSY-1 and KS-SLK cells by Fab-FGF2 conjugate. The effect of GCV on AdCMVHStk-transfected cells is assessed in the presence or absence of the conjugate and expressed as a percentage of cells surviving compared to the cell not exposed to GCV (i.e., -GCV). Viable cells in duplicate wells are counted, in triplicate, after trypan blue exclusion. On the vertical axis, the % of cells surviving is shown, in both FIGS. 3A and 3B. In FIG. 3A, KSY-1 cells transfected with AdCMVHSVtk or AdCMVHSVtk+Fab-FGF2 are identified on the horizontal axis. In FIG. 3B, KS-SLK cells transfected with AdCMVHSVtk or AdCMVHSVtk+Fab-FGF2 are identified on the horizontal axis.

Cell killing is expressed as a ratio of cells surviving in the presence of GCV relative to the number of cells surviving in the absence of GCV. FIG. 3 demonstrates that retargeting AdCMVHSVtk with Fab-FGF2 resulted in a significant enhancement of the KS cells susceptibility to GCV-mediated killing. These studies thus confirm our hypothesis that efficient gene transfer may be accomplished in KS cells by retargeting adenovirus via FGFR. Importantly, this maneuver quantitatively increased transduction efficiency in all cell lines tested. When Ad does not target a cell, this technique allows us to target it to a receptor, and the resulting response is greater than anticipated.

Example 2

Targeted Gene Delivery via FGFR

Recombinant adenovirus vectors are of great interest in the context of cancer gene therapy due to their ability to accomplish efficient in vivo gene transfer. However, targeting of these vectors to specific cell types remains an obstacle. To achieve specific targeting, a neutralizing anti-knob antibody fragment (Fab) which inhibits Ad infection is conjugated to the basic fibroblast growth factor (FGF2) ligand. The resulting conjugate, Fab-FGF2, is characterized by Western analysis using an anti-FGF2 antibody. Functional validation of the FGF2 activity in the conjugate is accomplished using an endothelial cell proliferation assay, and an ELISA is performed to validate that the Fab component of the conjugate still bound to Ad5 knob. The Fab-FGF2 conjugate is then used to target an Ad vector carrying the luciferase reporter gene (AdCMVLuc) to FGF receptor-positive cells (Swiss 3T3, PANC-1, SKOV3.ip1, and D54 MG) in vitro.

Our results demonstrated that the Ad targeted with the Fab-FGF2 conjugate achieved a level of gene expression that is significantly greater than when Ad alone is used in all of the cell lines. Furthermore, the Fab-FGF2 conjugate is able to achieve specific in vivo delivery of AdCMVLuc to SKOV3.ip1 tumors implanted intraperitoneally into nude mice. Thus, this work demonstrates that Ad vectors can be targeted to specific cell types in vivo using appropriate ligands. This is of tremendous potential utility when using Ad vectors in a variety of gene therapy strategies.

C. Materials and Methods

1. Cells and Viruses

PANC-1, a human pancreatic epithelioid carcinoma cell line, and Swiss 3T3, a mouse fibroblast cell line, are obtained from the American Type Culture Collection (ATCC, Rockville, Md.). (For example, see ATCC Accession Nos. CRL-1469 and CCL-92, respectively.) D54 MG, human glioma cells, are a derivative of the A172 cell line established by Giard et al. (See, e.g., Giard et al., *J. Natl. Cancer Inst.* 51:1417–23 (1973); Bigner, et al., *J. Neuropathol. Exp. Neurol.* 40:390–409 (1981); and Goldman et al., *Mol. Biol. Cell* 4:121–33 (1993).) The SKOV3.ip1 human ovarian adenocarcinoma cell line is kindly provided by Janet Price (Baylor University). (The related SKOV3 cell line is available from the ATCC under accession no. HTB-77.) Bovine aortic endothelial cells are obtained from primary cultures (Gospodarowicz, et al., *Endocrinology* 117:2383–91 (1985)).

The 3T3, PANC-1 and SKOV3.ip1 cells are maintained in Dulbecco's modified Eagles medium (DMEM) supplemented with 10% fetal calf serum (FCS) (Summit Biotechnology, Fort Collins, Colo.) and 2 mM L-glutamine. The D54 MG cells are maintained in DMEM/F12 supplemented with 7% FCS and 2 mM L-glutamine. The bovine aortic endothelial cells are maintained in DMEM supplemented with 10% FCS, gentamycin (50 ug/mL), 2 mM L-glutamine, 1 mM MEM sodium pyruvate solution, and 0.1 mM MEM non-essential amino acids solution. AdCMVLuc (Herz and Gerard, *PNAS USA* 90:2812–6 (1993)) is an E1-deleted replication-deficient Ad5 vector which expresses firefly luciferase (Luc) under the control of the cytomegalovirus (CMV) promoter. The aforementioned vector may be prepared as described in the cited reference. The adenovirus is propagated on the permissive 293 cell line and purified by standard techniques.

2. Conjugation of FGF2 to 1D6.14-Fab

The 1D6.14-Fab is generated and characterized as previously described (Douglas, et al., *Nature Biotech.* 14:1574–78 (1996)). The Fab (1.6 mg) is dialyzed against 0.1 M sodium phosphate buffer, pH 7.5, containing 0.1 M NaCl and 1.0 mM EDTA (BPS-E) at 1:250 (v/v) for 3 hours with two changes of buffer. The dialyzed Fab fragment is centrifuged at 14,000 rpm for 10 minutes and the supernatant collected. The Fab fragment is derivatized with N-succinimidyl-3(pyridyldithio)propionate (SPDP) (Pharmacia, Uppsala, Sweden) at a molar ratio of 1:3 for 30 minutes at room temperature, with occasional stirring. The excess SPDP and low molecular weight reaction byproducts are removed by dialysis against PBS-E (1:500, v/v). An FGF2 mutein is used in all of the studies described herein; this mutein has its cysteine at position 96 mutagenized to serine. The FGF2 mutein is expressed in *E. coli* and purified as described previously (Lappi, et al., *Anal. Biochem.* 212:446–51 (1993)).

The reaction containing the FGF2 mutein is adjusted to pH 7.5 by adding Tris-base and reduced by adding monothioglycerol (MTG; Evans Chemetics, Waterloo, N.Y.) to a final concentration of 20 mM. The reaction is performed at room temperature for 30 minutes before the excess MTG is removed by passing the mixture over a PD-10 column (Pharmacia) and eluting with 10 mM NaOAc/HOAc, pH 5.4, containing 0.14 M NaCl and 1 mM EDTA. The reduced FGF2 mutein is then mixed with the SPDP derivatized Fab at a molar ratio of 2:1 at pH 7.5 and incubated at 4 C for 16 hours with shaking.

The conjugate is purified over a heparin-Sepharose column (I mL heparin Hi-Trap, Pharmacia) to remove unconjugated Fab fragment by loading the reaction mixture onto the column in 10 mM Tris pH 7.4 and washing in the same buffer plus 0.6 M NaCl. When the absorbance returned to background, the conjugate is eluted from the column with the same buffer containing 2 M NaCl. The 2 M eluate is then loaded onto a Sephacryl S-100 column (Pharmacia) to remove free FGF2 mutein and buffer exchanged into PBS pH 7.4. The final protein concentration of the Fab is 0.24 mg/mL. The Fab is used directly in the following studies.

3. Characterization of Fab-FGF2 Conjugate

The Fab-FGF2 conjugate is evaluated by SDS-PAGE (12%) under nonreducing conditions and stained with Coomassie blue. Western blot analysis is also conducted on the conjugate by transferring protein to a nitrocellulose membrane, probing with anti-FGF2 rabbit polyclonal antibodies and then with 125I-Protein A, which is revealed by autoradiography.

The activity of the FGF2 component of the Fab-FGF2 conjugate is confirmed using a cell proliferation assay. Bovine aortic endothelial cells are seeded at 1000 cells/well in 24-well tissue culture plates. The following day, serial dilutions of FGF2 or the Fab-FGF2 conjugate (30 pg/m: to 6 ng/mL) are added to triplicate wells. After 48 hours, the media are removed and 1.5 mL of fresh media containing the same concentrations of FGF2 and Fab-FGF2 are added. Following another 72 hr incubation, the media are removed, the cells are washed with PBS, treated with 0.25% trypsin, and counted using a Coulter Particle Counter (Coulter).

The activity of the Fab portion of the Fab-FGF2 conjugate is confirmed by ELISA. Recombinant trimeric Ad5 knob protein (180 ng) with an N-terminal 6-His tag (Krasnykh, et al., *J. Virol.* 70:6839–6846 (1996)) is plated on Ni-NTA HisSorb Strips (Qiagen, Chatsworth, Calif.) for 1 hr at room temperature. The Fab-FGF2 conjugate or the appropriate controls are added to the wells and the assay performed according to the Qiagen protocol. A polyclonal anti-FGF2 antibody (Sigma Immunochemicals, St. Louis, Mo.) is used as the primary antibody, while a goat anti-rabbit antibody conjugated to horseradish peroxidase (Southern Biotechnology Associates, Birmingham, Ala.) is used as the secondary antibody.

4. In Vitro Infection Using Fab-FGF2 Conjugate 10.5 ug of neutralizing antibody (Fab) or the antibody-conjugate (Fab-FGF2) are incubated with 1.9×108 plaque forming units (pfu) of AdCMVLuc at room temperature in a total volume of 110 uL of HEPES buffered saline, pH 7.3. After 30 min, 9 uL of the Fab or Fab-FGF2 AD complexes are added in triplicate to the 3T3, PANC-1, SKOV3.ip1, and D54 MG cells plated at a density of 24,000 cells/well 24 hours previously. The cells are first washed with PBS and supplemented with 200 uL of OPTI-MEM reduced serum media (Gibco-BRL, Grand Island, N.Y.) prior to addition of the complexes. After incubation for 1 hr at 37 C, the cells are supplemented with 1 mL of complete media and allowed to incubate an additional 24 hours at 37 C. The cells are then lysed and extracts assayed for luciferase activity using a luciferase assay system (Promega, Madison, Wis.) according to the manufacturer's protocol. The relative light units (RLU) are normalized for protein content using the BioRad protein assay, following the manufacturer's protocol. Inhibition studies are conducted by adding a polyclonal anti-FGF2 antibody (Sigma Immunochemicals) to the AdCMVLuc-Fab-FGF2 mixture prior to cell infection. All experiments are performed in triplicate.

In Vivo Infection Using Fab-FGF2 Conjugate

In vivo experiments are performed in athymic nude mice implanted intraperitoneally (i.p.) with SKOV3.ip1 cells. The SKOV3.ip1 cells (2×107) are implanted via an i.p. injection and allowed to grow for 7 days. Mice are then injected i.p. with either AdCMVLuc (1×108 fpu), AdCMVLuc-Fab, AdCMVLuc-Fab-FGF2, or AdCMVLuc-Fab-FGF2 incubated with the anti-FGF2 antibody in a total volume of 600 uL of media containing 2% FCS.

The AdCMVLuc-Fab and AdCMVLuc-Fab-FGF2 conjugates are made in a manner consistent with that described above. Two days after Ad injection, the mice are sacrificed and the tumors and dorsal mesothelial lining harvested. The organs are rinsed with water, homogenized in grinding buffer (50 mM $K_3PO_4$, 1 mM EDTA, 1 mM dithiothreitol, 10% glycerol), and lysed with lysis buffer (Promega). The homogenates are incubated on ice for 30 minutes and then centrifuged for 10 min at 14,000 rpm and 4 C. The supernatants are assayed for luciferase activity as described above and standardized for total protein content.

D. Results and Discussion

1 Conjugation of FGF2 to Fab

The Fab fragment of the 1D6.14 anti-Ad5 knob neutralizing antibody is derivatized with SPDP and conjugated to the one remaining active cysteine on the FGF2 mutein (FIG. 4). The reaction is monitored by size exclusion HPLC and the conjugate purified using a heparin-Sepharose column followed by Sephacryl S-100 gel filtration.

FIG. 4 illustrates a schema for the synthesis and purification of the Fab-FGF2 conjugate. It should be expressly understood that this schema may be applied to the synthesis and purification of any Fab-ligand conjugate and is thus not limited to the one illustrated.

Figures 5A, 5B:
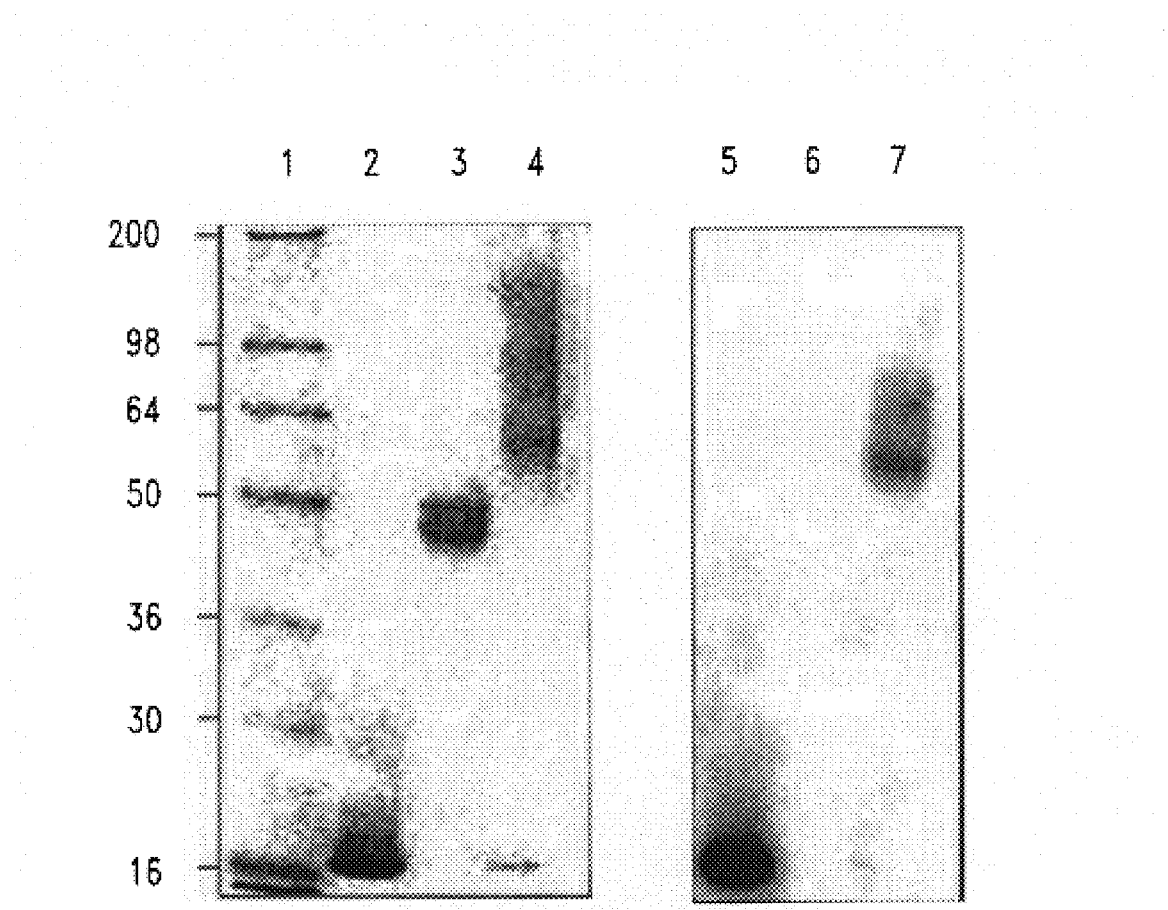
In FIG. 5B, Western blot analysis of Fab-FGF2 conjugate is shown. The protein was transferred to a nitrocellulose membrane, probed with an anti-FGF2 rabbit polyclonal antibody and then with $^{125}$I-Protein A and visualized by autoradiography. A band was observed for FGF2 (lane 5) and for the Fab-FGF2 conjugate (lane 7), but not for Fab antibody alone (lane 6).

FIG. 5A shows the results of SDS-PAGE of Fab-FGF2 under non-reducing conditions. Equal amounts (2 ug) of FGF2 (lane 2), Fab (lane 3), or Fab-FGF2 (lane 4) are applied to the gel and compared to the molecular weight standards (lane 1, in thousands) by staining with Coomassie blue. In FIG. 5B, Western blot analysis of Fab-FGF2 conjugate is shown. The protein is transferred to a nitrocellulose membrane, probed with an anti-FGF2 rabbit polyclonal antibody and then with $^{125}$I-Protein A and visualized by autoradiography. A band is observed for FGF2 (lane 5) and for the Fab-FGF2 conjugate (lane 7), but not for Fab antibody alone (lane 6).

Integrity of the conjugate is confirmed by SDS-PAGE analysis (FIG. 5A, Lane 4) in which the Coomassie stain showed bands corresponding to the Fab-FGF2 conjugate and did not show the presence of free FGF2. In addition, Western analysis using an antibody generated against FGF2 showed bands corresponding to the size of the Fab-FGF2 conjugates (FIG. 5B, lane 7) and did not show the presence of free FGF2. Thus, it is confirmed that FGF2 is conjugated to the Fab and that excess FGF2 had been removed.

2. Functional Validation of Fab-FGF2 Coniugate

The Fab-FGF2 conjugate is compared with unconjugated FGF2 in an endothelial cell proliferation assay. The results of the endothelial cell proliferation assay showed the conjugation of the Fab to FGF2 did not interfere with the ability of FGF2 to bind to its cognate receptor and stimulate proliferation (FIG. 6A).

To determine if the Fab-FGF2 conjugate still retained knob-binding ability, an ELISA assay is performed. The plates are probed using an anti-FGF2 primary antibody and then with a goat anti-rabbit secondary antibody prior to addition of the substrate for visualization. The Fab-FGF2 conjugate had an absorbance of 3.70±0.13 when added to wells containing Ad5 knob, compared to 0.35±0.04 in wells without the Ad5 knob (FIG. 6B). In addition, the absorbance of the conjugate is significantly greater than when FGF2 alone is added (1.55±0.03) (p<0.002). Therefore, we are able to show that the Fab portion of the Fab-FGF2 conjugate bound to Ad5 knob after conjugation and that the FGF2 portion of the conjugate is still functional as evidenced by the endothelial cell proliferation assay.

Figure 6A:
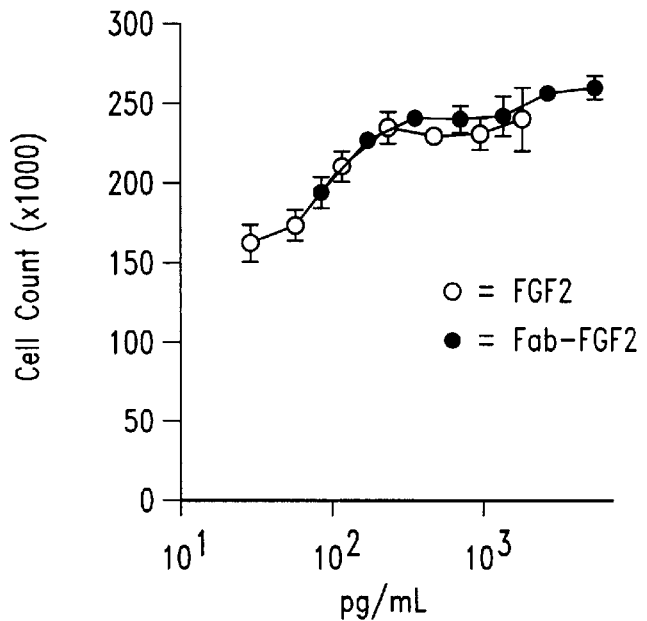
In FIG. 6A, stimulation of endothelial cell proliferation by FGF2 and the Fab-FGF2 conjugate is shown. Bovine aortic endothelial cells were treated with various concentrations of FGF2 or Fab-FGF2 (30 pg/mL to 6 ng/mL) and the cell number determined. Cell count (×1000) is plotted on the vertical axis, while pg/mL are plotted on the horizontal axis. Open circles represent FGF2, while closed circles represent Fab-FGF2.
Figure 6B:
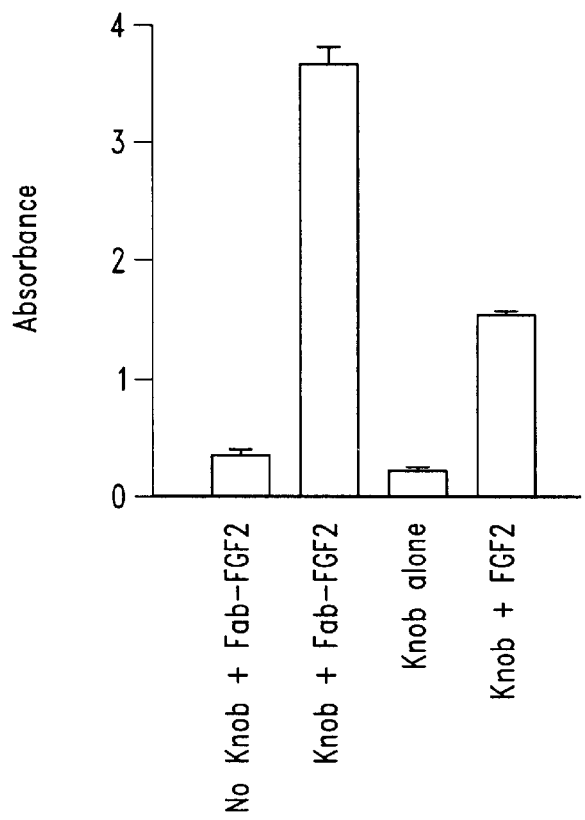
In FIG. 6B, Fab-FGF2 binding to Ad5 knob in an ELISA is illustrated. Recombinant Ad5 knob was probed with either Fab-FGF2, a blank control, or FGF2. As a control, Fab-FGF2 was added to plates that did not contain Ad5 knob. Absorbance is plotted on the vertical axis, while the following are shown on the horizontal axis of the bar graph, proceeding from left to right: No knob+Fab-FGF2; Knob+Fab-FGF2; Knob alone; and Knob+FGF2.

As summarized briefly above, the results of the assays are illustrated in FIGS. 6A and 6B. FIG. 6 shows functional validation of the Fab-FGF2 conjugate. In FIG. 6A, stimulation of endothelial cell proliferation by FGF2 and the Fab-FGF2 conjugate is shown. Bovine aortic endothelial cells are treated with various concentrations of FGF2 or Fab-FGF2 (30 pg/mL to 6 ng/mL) and the cell number determined. Cell count (×1000) is plotted on the vertical axis, while pg/mL are plotted on the horizontal axis. Open circles represent FGF2, while closed circles represent Fab-FGF2.

In FIG. 6B, Fab-FGF2 binding to Ad5 knob in an ELISA is illustrated. Recombinant Ad5 knob is probed with either Fab-FGF2, a blank control, or FGF2. As a control, Fab-FGF2 is added to plates that did not contain Ad5 knob. Absorbance is plotted on the vertical axis, while the following are shown on the horizontal axis of the bar graph, proceeding from left to right: No knob+Fab-FGF2; Knob+Fab-FGF2; Knob alone; and Knob+FGF2.

3. In Vitro Infection Using Fab-FGF2 Coniugate

Having shown that the Fab-FGF2 conjugate stimulated endothelial cell proliferation and bound to the adenoviral fiber knob, the conjugate is then used to show targeting of AdCMVLuc to high-affinity FGF receptors in vitro. Four cell lines—3T3, PANC-1, SKOV3.ip1, and D54MG—are infected with either AdCMVLuc alone, AdCMVLuc premixed with the Fab, AdCMVLuc premixed with the Fab-FGF2, or AdCMVLuc premixed with the Fab-FGF2 and the anti-FGF2 antibody.

Twenty-four hours post-infection, a luciferase assay is performed. The 3T3, PANC-1, SKOV3.ip1, and D54 MG cells infected with AdCMVLuc alone resulted in luciferase activity of $3.7 \times 10^4$, $5.8 \times 10^4$, $8.4 \times 10^4$, and $2.0 \times 10^6$ RLU/ug of protein, respectively (FIG. 7).

Figure 7A:
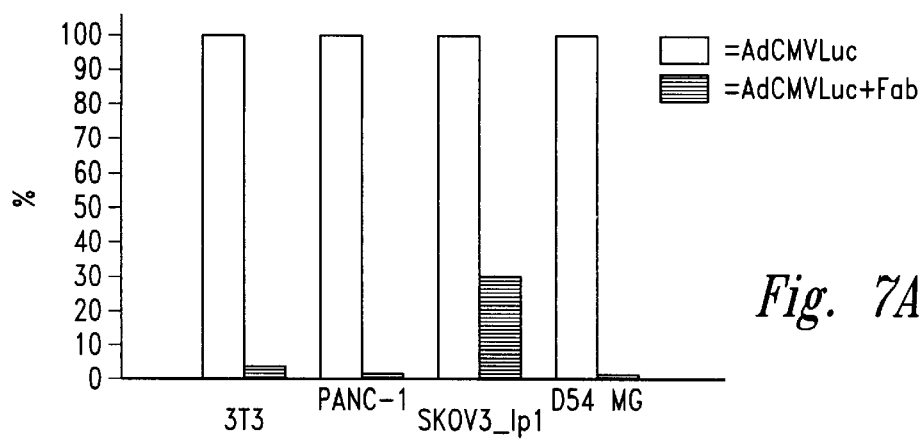
In FIG. 7A, inhibition of luciferase expression by the Fab is shown. The four cell lines were infected with either the AdCMVLuc or the AdCMVLuc premixed with the Fab as described in the text. The data are expressed as a percentage of the luciferase expression when AdCMVLuc alone was used for each cell line. Percentage is plotted on the vertical axis; cell lines 3T3, PANC-1, SKOV3.ip1, and D54 MG are illustrated along the horizontal axis. Open bars represent AdCMVLuc, while closed bars represent AdCMVLuc+Fab.

FIG. 7 illustrates the results of in vitro infection of a panel of cell lines using the Fab-FGF2 conjugate. In FIG. 7A, inhibition of luciferase expression by the Fab is shown. The four cell lines are infected with either the AdCMVLuc or the AdCMVLuc premixed with the Fab as described in the text. The data are expressed as a percentage of the luciferase expression when AdCMVLuc alone is used for each cell line. Percentage is plotted on the vertical axis; cell lines 3T3, PANC-1, SKOV3.ip1, and D54 MG are illustrated along the horizontal axis. Open bars represent AdCMVLuc, while closed bars represent AdCMVLuc+Fab.

Figure 7B:
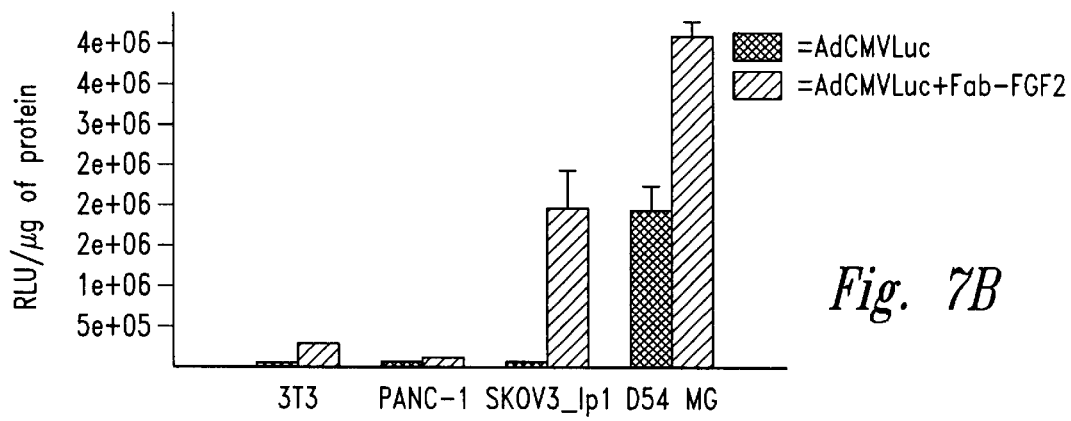
In FIG. 7B, luciferase expression in the four cell lines when infected with either AdCMVLuc or the AdCMVLuc-Fab-FGF2 conjugate is shown. The bars illustrate the luciferase expression in relative light units (RLU) per microgram of protein and represent triplicate measurements±standard deviation. RLU/ug of protein is plotted on the vertical axis. On the horizontal axis, cell lines 3T3, PANC-1, SKOV3.ip1, and D54 MG are illustrated. Closed bars represent AdCMVLuc, while cross-hatched bars represent AdCMVLuc+Fab-FGF2.

In FIG. 7B, luciferase expression in the four cell lines when infected with either AdCMVLuc or the AdCMVLuc-Fab-FGF2 conjugate is shown. The bars illustrate the luciferase expression in relative light units (RLU) per microgram of protein and represent triplicate measurements±standard deviation. RLU/ug of protein is plotted on the vertical axis. On the horizontal axis, cell lines 3T3, PANC-1, SKOV3.ip1, and D54 MG are illustrated. Closed bars represent AdCMVLuc, while cross-hatched bars represent AdCMVLuc+Fab-FGF2.

Figure 7C:
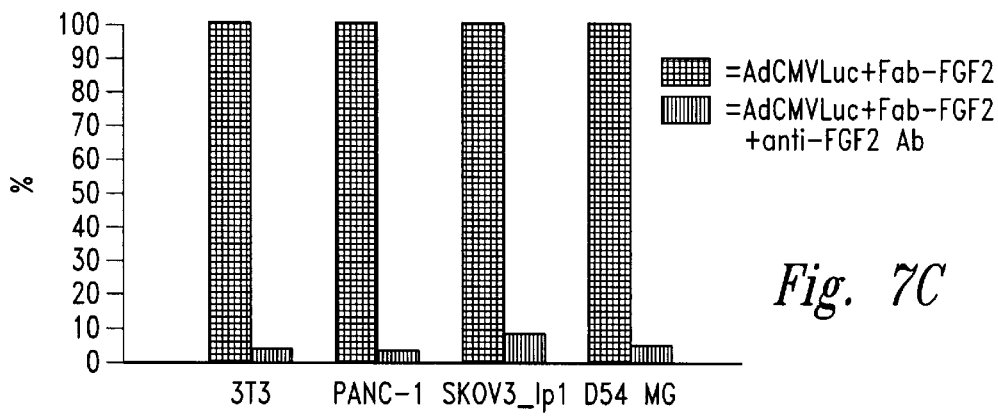
In FIG. 7C, inhibition of luciferase expression by the anti-FGF2 antibody is shown. The four cell lines were infected with either AdCMVLuc premixed with the Fab-FGF2 conjugate or AdCMVLuc premixed with the Fab-FGF2 conjugate and the anti-FGF2 antibody as described above. The data are expressed as a percentage of the luciferase expression seen when the ADCMVLuc-Fab-FGF2 complex was used for each cell line. Percentages are plotted on the vertical axis; cell lines 3T3, PANC-1, SKOV3.ip1, and D54 MG are illustrated along the horizontal axis. Lightly shaded bars represent AdCMVLuc+Fab-FGF2, while the dark, closed bars represent AdCMVLuc+Fab-FGF2+anti-FGF2 Ab.

In FIG. 7C, inhibition of luciferase expression by the anti-FGF2 antibody is shown. The four cell lines are infected with either AdCMVLuc premixed with the Fab-FGF2 conjugate or AdCMVLuc premixed with the Fab-FGF2 conjugate and the anti-FGF2 antibody as described above. The data are expressed as a percentage of the luciferase expression seen when the ADCMVLuc-Fab-FGF2 complex is used for each cell line. Percentages are plotted on the vertical axis; cell lines 3T3, PANC-1, SKOV3.ip1, and D54 MG are illustrated along the horizontal axis. Lightly shaded bars represent AdCMVLuc+Fab-FGF2, while the dark, closed bars represent AdCMVLuc+Fab-FGF2+anti-FGF2 Ab.

The infection is inhibited in each of the cell lines by 97.0, 98.8, 69.3, and 98.3%, respectively, when AdCMVLuc is premixed with the Fab antibody (FIG. 7A). Interestingly, each of the cell lines exhibited a higher level of luciferase activity ($2.9 \times 10^5$, $1.3 \times 10^5$, $2.0 \times 10^6$, and $4.1 \times 10^6$ RLU/ug of protein, respectively) when infected with AdCMVLuc premixed with the Fab-FGF2 conjugate than when infected with AdCMVLuc alone (FIG. 7B). The anti-FGF2 antibody inhibited cell infection by the Ad-Fab-FGF2 complex by 96.1, 96.3, 90.1, and 94%, respectively (FIG. 7C). These results demonstrated that the complex specifically re-targeted Ad to high-affinity FGF receptors. By re-targeting through this pathway, higher levels of gene transfer are achieved than when Ad is routed through its native receptor pathway.

4. In Vivo Infection Using Fab-FGF2 Conjugate

Therapeutic index in gene therapy approaches is frequently dictated by the differential between tumor and non-tumor cell transduction. We thus explored the capacity to achieve tumor-specific delivery in a murine model of ovarian carcinoma. Luciferase activity in the tumor and dorsal mesothelial lining in athymic nude mice bearing SKOV3.ip1 tumors in the peritoneum is determined 48 hr after i.p. administration of AdCMVLuc alone, AdCMVLuc premixed with Fab, AdCMV Luc premixed with Fab-FGF2, or AdCMVLuc premixed with Fab-FGF2 and the anti-FGF2 antibody (Table 1). Table 1 shows luciferase expression (RLU/ug) in the tumor and dorsal mesothelial lining 48 hr after administration of the various AdCMVLuc complexes for each athymic nude mouse.

TABLE 1

| Animal # | adCMVLuc | | AdCMVLuc + Fab | | AdCMVLuc + Fab-FGF2 | | AdCMVLuc + Fab-FGF2 + anti-FGF2 | |
|---|---|---|---|---|---|---|---|---|
| | Tumor | Lining | Tumor | Lining | Tumor | Lining | Tumor | Lining |
| 1 | 98.2 | 10.3 | 180 | 8.9 | 5557 | 1098 | 1853 | 26.8 |
| 2 | 36.8 | 24.2 | 7.0 | 8.3 | 25,843 | 452 | 5578 | 108 |
| 3 | 133 | 21.2 | 11.0 | 4.5 | 5633 | 212 | 1132 | 153 |
| 4 | 255 | 4.5 | 177 | 7.1 | 7587 | 201 | 294 | 56.4 |
| 5 | — | — | 34.2 | 33.0 | 1628 | 55.0 | 2648 | 208 |
| Mean | 131 | 15.1 | 81.8 | 12.4 | 9250 | 404 | 2301 | 110 |
| std dev | ±92 | ±9.2 | ±88.9 | ±11.7 | ±9525 | ±413 | ±2028 | ±72.9 |

The results illustrated in Table 1 indicate that the tumor is more susceptible to Ad transduction than the dorsal mesothelial lining (131 vs. 15.1 RLU/ug protein, respectively) and both organs showed a reduction in luciferase activity when the Ad-Fab complex is administered to mice (37.6% inhibition in tumor and 17.9% inhibition in abdominal lining). However, when the mice are administered Ad-Fab-FGF2, both the tumor and the abdominal lining exhibited higher luciferase activity (9250 and 404 RLU/ug protein, respectively) than when administered the Ad alone. The ratios of luciferase activity in the tumor to the luciferase activity in the dorsal mesothelial lining when AdCMVLuc alone or AdCMVLuc targeted with Fab-FGF2 are administered are 18.5 and 31.2, respectively. These results demonstrate that the Fab-FGF2 conjugate targets AdCMVLuc preferentially to the FGF receptor-positive tumor cells in this in vivo model of ovarian cancer.

Example 3

Preparation of FGF Muteins

As disclosed above, FGF-related molecules, including analogs, derivatives, fragments, and mimics thereof, are useful in conjugates, compositions, systems and methods of the present invention. Procedures for the preparation of FGF muteins are provided hereinbelow for purposes of example and illustration of some of the molecules that are useful as disclosed herein.

E. Materials and Methods

1. Reagents

Plasmid pFC80, containing the FGF2 coding sequence, is a gift of Drs. Paolo Sarmientos and Antonella Isacchi of Farmitalia Cargo Erba (Milan, Italy). Plasmid pFC80, has been described in the PCT Application Serial No. WO 90/02800 and PCT Application Serial No. PCT/US93/05702. The sequence of DNA encoding FGF2 in pFC80 is that set forth in PCT Application Serial No. PCT/US93/05702.

Plasmid isolation, production of competent cells, transformation and M13 manipulations are carried out according to published procedures (Sambrook et al., *Molecular Cloning, a Laboratory Manual*, Cold Spring Harbor Laboratory Press, Cold Spring Harbor, N.Y., 1989). Purification of DNA fragments is achieved using the GENECLEAN II kit, purchased from Bio 101 (LaJolla, Calif.). Sequencing of the different constructions is performed using the SEQUENASE kit (version 2.0) of USB (Cleveland, Ohio).

2. Sodium Dodecyl Sulfate (SDS) Gel Electrophoresis and Western Blotting

SDS gel electrophoresis is performed on a PhastSystem utilizing 20% gels (Pharmacia). Western blotting is accomplished by transfer of electrophoresed protein to nitrocellulose using the PhastTransfer system (Pharmacia), as described by the manufacturer. The antisera to SAP and basic FGF are used at a dilution of 1:1000. Horseradish peroxidase labeled anti-IgG is used as the second antibody.

F. Preparation of the mutagenized FGF by site-directed mutagenesis

Cysteine to serine substitutions are made by oligonucleotide-directed mutagenesis using the Amersham (Arlington Heights, Ill.) in vitro-mutagenesis system 2.1. Oligonucleotides encoding the new amino acid are synthesized using a 380B automatic DNA synthesizer (Applied Biosystems, Foster City, Calif.).

1. Mutagenesis

The oligonucleotide used for in vitro mutagenesis of cysteine 78 is AGGAGTGTCTGCTAACC (SEQ ID NO: 3), which spans nucleotides 225–241 of FGF2. The oligonucleotide for mutagenesis of cysteine 96 is TYCTAAATCGGTTACCGATGACTG (SEQ ID NO: 4), which spans nucleotides 279–302. The mutated replicative form DNA is transformed into *E. coli* strain JM109 and single plaques are picked and sequenced for verification of the mutation. The FGF mutated gene is then cut out of M13, ligated into the expression vector pFC80, which had the non-mutated form of the gene removed, and transformed into *E. coli* strain JM109. Single colonies are picked and the plasmids sequenced to verify the mutation is present. Plasmids with correct mutation are then transformed into the *E. coli* strain FICE 2 and single colonies from these transformations are used to obtain the mutant basic FGFs. Approximately 20 mg protein per liter of fermentation broth is obtained.

2. Purification of Mutagenized FGF

Cells are grown overnight in 20 ml of LB broth containing 100 $\mu$g/ml ampicillin. The next morning the cells are pelleted and transferred to 500 ml of M9 medium with 100 $\mu$g/ml ampicillin and grown for 7 hours. The cells are pelleted and resuspended in lysis solution (10 mM TRIS, pH 7.4, 150 mM NaCl, lysozyme, 10 $\mu$g/mL, aprotinin, 10 $\mu$g/mL, leupeptin, 10 $\mu$g/mL, pepstatin A, 10 $\mu$g/mL and 1 mM PMSF; 45–60 ml per 16 g of pellet) and incubated while stirring for 1 hour at room temperature. The solution is frozen and thawed three times and sonicated for 2.5 minutes. The suspension is centrifuged; the supernatant saved and the pellet resuspended in another volume of lysis solution without lysozyme, centrifuged again and the supernatants pooled. Extract volumes (40 ml) are diluted to 50 ml with 10 mM TRIS, pH 7.4 (buffer A). Pools are loaded onto a 5 ml Hi-Trap heparin-Sepharose column (Pharmacia, Uppsala, Sweden) equilibrated in 150 mM sodium chloride in buffer A. The column is washed with 0.6 M sodium chloride and 1 M sodium chloride in buffer A and then eluted with 2 M sodium chloride in buffer A. Peak fractions of the 2 M elution, as determined by optical density at 280 nm, are pooled and purity determined by gel electrophoresis. Yields are 10.5 mg of purified protein for the $Cys^{78}$ mutant and 10.9 mg for the $Cys^{96}$ mutant.

The biological activity of [C78S]FGF and [C96S]FGF is measured on adrenal capillary endothelial cells in culture. Cells are plated at 3,000 per well in a 24 well plate in 1 ml of 10% calf serum-HDMEM. Cells are allowed to attach, and samples are added in triplicate at the indicated concentration and incubated for 48 h at 37° C. An equal quantity of samples is added and further incubated for 48 hr. Medium is aspirated; cells are treated with trypsin (1 ml volume) to remove cells to 9 ml of Hematall diluent and counted in a Coulter Counter. The results show that the two mutants that retain virtually complete proliferative activity of native basic FGF as judged by the ability to stimulate endothelial cell proliferation in culture.

Example 4

Efficacy and Toxicity of FGF-Ad

As disclosed above, viral vectors re-targeted with polypeptides that target the FGF receptor—including derivatives and fragments of FGF and polypeptide portions thereof—are useful in conjugates, compositions, systems and methods of the present invention. Procedures and exemplary data illustrating some of the novel and unexpected advantages of the use of the constructs of the present invention are provided hereinbelow for purposes of example and illustration.

A. Methods

1. Toxicity Assessment In Vivo

Toxicity of FGF Ad βgal and Ad βgal is assessed in female C57B1/6 mice (n=5/group). For preparation of FGF Ad βgal or Ad βgal, 77 μg of FGF-Fab, or an equivalent volume of 0.9% NaCl is incubated for 30 minutes at room temperature with $2 \times 10^{10}$ pfu of Ad βgal. $2 \times 10^{10}$ pfu of either Ad βgal or FGF-Ad βgal are injected intravenously per mouse (over a 30 second period) in a final volume of 0.32 ml. Control mice received 0.32 ml of excipient (25 mM Tris pH 7.5, 100 mM NaCl, 10 mg/ml lactose). On day 4 post injection, 2 mice per group are sacrificed. Serum is collected for analysis of serum transaminases and alkaline phosphatase. The liver, lungs, spleen, and kidneys are removed and weighed. A portion of liver and lung are immediately snap frozen in liquid nitrogen, stored at −80° C. and then processed for quantitative analysis of β-galactosidase activity. Portions of each organ are snap frozen in OCT using isopentane precooled with dry ice and stored at −80° C. Another portion of each organ is fixed for 4 hours at 4° C. in 10% neutral buffered formalin and then embedded in paraffin. On day 7, three mice per group are sacrificed and tissues and serum are processed in the same manner.

2. β-Galactosidase Activity Measurement

β-gal activity is quantitated in mouse liver homogenates according to standard techniques. Briefly, frozen tissues are minced with razor blades and homogenized on ice in cold lysis buffer by hand using glass douncers. 0.1 g of organ weight is added per mL of 0.2% Triton, 100 mM Potassium Phosphate lysis buffer, pH 7.8. Homogenates are clarified by two centrifugation steps of 20 minutes each at 4° C. in a microfuge at 12,000×g. Supernatants are treated with Chelex-100 resin (BioRad catalog #142–2842) by adding 0.25×volume chelator to each sample. Homogenates are then vortexed briefly, incubated at room temperature for 2–5 minutes, and centrifuged for 30 seconds in a microfuge at 12K×g. A two-fold dilution series of each supernatant is assayed using the Clontech Luminescent β-gal Detection Kit II (catalog #K2048-1). 10 μl of each sample dilution is incubated with 75 μl Clontech β-gal Reagent in 96-well plates at room temperature for 1 hour and read in a Dynatech Laboratories ML3000 Microtiter plate luminometer. The activity of each sample is determined by extrapolation from a standard curve of β-gal enzyme supplied with the Clontech kit, and is expressed in mU/g organ weight.

3. Histological Determination of β-Galactosidase Activity

Eight micron cryostat sections are fixed in 2% PFA, 0.5% GA in PBS pH 7.4 for 30 min. at room temperature. Tissue sections are then rinsed in PBS containing 0.03% NP-40 and 2 mM $MgCl_2$ and incubated in X-Gal solution for 16 hr. at 37° C. (1 mg/ml X-Gal, 5 mM $K_3Fe(CN)_6$, 3 mM $K_4Fe(CN)_6$ in PBS pH 7.4 containing 2 mM $MgCl_2$ and 0.03% NP-40). Slides are rinsed in PBS, postfixed in 10% buffered formalin, counterstained for 15 sec. with Nuclear Fast Red, dehydrated and mounted. For morphological studies, routine hematoxylin and eosin staining is performed on paraffin embedded tissues.

4. In Vivo Tumor Model

FGF-$Ad_{HSVTK}$ is prepared by mixing 0.3 μg of FGF-Fab with $1 \times 10^8$ pfu of FGF-$Ad_{HSVTK}$ and incubating for 30 minutes at room temperature. Either FGF-$Ad_{HSVTK}$, $Ad_{HSVTK}$, or 20 mM HEPES buffer are then mixed with B16 melanoma cells in suspension at an MOI of 50. This mixture is incubated at room temperature for one hour. Female BDF1 mice (n=8/group) had $2 \times 10^6$ B16 cells, treated with either FGF-$Ad_{HSVTK}$, $Ad_{HSVTK}$, or 20 mM HEPES buffer implanted intraperitoneally on day 0. Mice are then treated with ganciclovir (or $H_2O$) beginning on day 1, qd×14, at a dose of 100 mg/kg. Mice are then followed for survival. Statistical analysis is performed using Kaplan-Meier and a Logrank (Mantel-Cox) post-hoc analysis.

B. Results

I. Toxicity analysis To accomplish retargeting of Ad, we have made a bi-functional molecule by conjugating FGF-2 to a blocking anti-adenoviral knob Fab. This molecule is then incubated with Ad prior to transduction of cells in vitro or use in vivo. To determine if FGF-2 retargeted Ad blocks the native tropism of Ad for the liver, FGF-2Adβgal and Adβgal are injected intravenously into mice and expression of βgal in hepatocytes is assessed.

FIGS. 8A–C illustrate the expression of β-galactosidase in the liver of mice after treatment with Adβgal or FGF2-Adβgal. In FIG. A, no Xgal stained cells in the liver of C57B1/6 mice treated with excipient are seen. In FIG. 8B, numerous Xgal stained hepatocytes are present in the liver of C57B1/6 mice treated with Adβgal at a dosage of $2 \times 10^{10}$ pfu per mouse, i.v. In FIG. 8C, treatment with FGF2-Adβgal at $2 \times 10^{10}$ pfu per mouse, i.v. transduces very few hepatocytes.

On day 4 post-administration, numerous Xgal stained hepatocytes are present in the livers of mice treated with Adβgal (see FIG. 8B). In the livers of mice treated with FGF-2Adβgal, there is a demonstrable decrease in Xgal stained hepatocytes (FIG. 8C). Quantitation of β-galactosidase activity in liver (Table 2) demonstrated 30-fold less βgal in the FGF-2Adβgal treated group than the in Adβgal treated group. Results are similar on day 7 post-administration for both Xgal staining and quantitation of β-galactosidase activity (Xgal staining omitted, quantitation in Table 2).

TABLE 2

Quantitation of β-Galactosidase in the Liver
of Mice Treated with AdβGal or FGF-AdβGal

| Treatment | Mean βGalactosidase Activity (mU/gram)* | |
|---|---|---|
| | Day 4 | Day 7 |
| AdβGal | 2008, 6542 | 1719, 50, 91 |
| FGF-AdβGal | 157, 126 | 5, 7, 4 |

*Activity measurements from individual animals.

Figure 9:
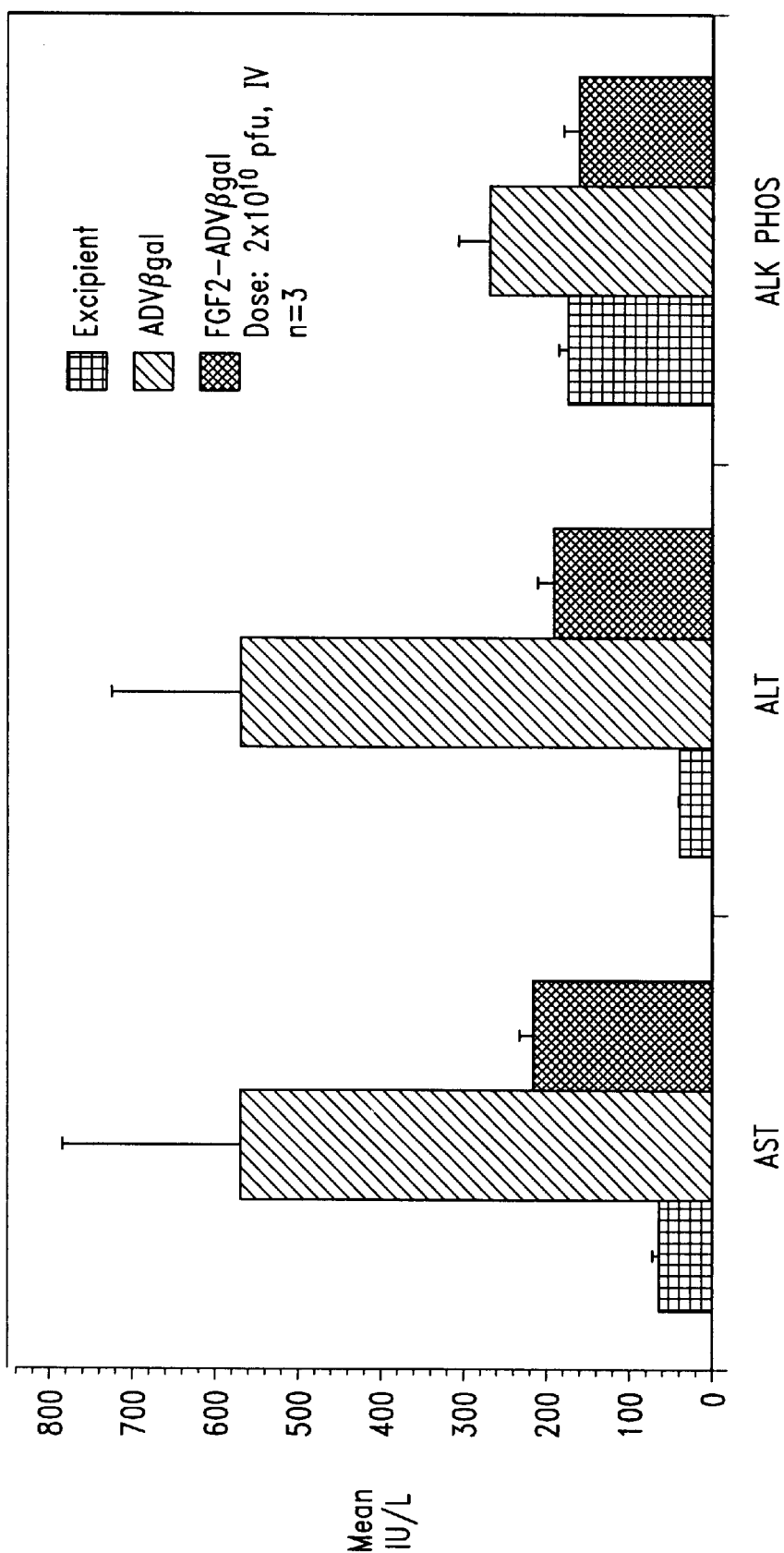
FIG. 9 shows the serum transaminase and alkaline phosphatase levels in mice treated with Adβgal or FGF2-Adβgal. Serum transaminases (AST, ALT) and alkaline phosphatase were measured on day 7 in C57B1/6 mice after treatment with either excipient; Adβgal, 2×10e10 pfu, i.v.; or FGF2-Adβgal, 2×10e10 pfu, i.v.

FIG. 9 shows the serum transaminase and alkaline phosphatase levels in mice treated with Adβgal or FGF2-Adβgal. Serum transaminases (AST, ALT) and alkaline phosphatase are measured on day 7 in C57B1/6 mice after treatment with either excipient; Adβgal, $2 \times 10^{10}$ pfu, i.v.; or FGF2-Adβgal, $2 \times 10^{10}$ pfu, i.v.

On day 7 post-administration, serum transaminase levels are elevated 8.2 to 13.6-fold in the Adβgal treated group but only a moderate 3.2 to 4.7-fold in the FGF-2Adβgal treated group (see FIG. 9). Serum alkaline phosphatase is also elevated in the serum of Adβgal treated mice but is normal in FGF-2Adβgal treated mice.

FIGS. 10A and 10B illustrate the histopathology of the liver of mice after treatment with Adβgal or FGF2-Adβgal. Hematoxylin and eosin stained paraffin sections of the liver of C57B1/6 mice treated with either Adβgal, $2 \times 10^{10}$ pfu, i.v. (FIG. 10A); or FGF2-Adβgal, $2 \times 10^{10}$ pfu, i.v. (FIG. 10B). Extensive hepatocellular necrosis and inflammatory infiltrate present in the liver of mice treated with Adβgal. There is nearly complete abrogation of hepatocellular necrosis in the liver of mice treated with FGF-2Adβgal. Also, very little inflammatory infiltrate is observed.

Histopathology on day 7 also revealed evidence of significant hepatocellular necrosis and inflammatory infiltrate in the liver of mice treated with Adβgal but analysis of livers from the FGF-2 Adβgal treated group revealed that the hepatocellular necrosis is almost completely abrogated and no inflammatory infiltrate is present (FIG. 10).

2. Ex vivo Transduction of B16 Melanoma

To determine whether FGF-Ad can transduce cells which are insensitive to Ad, the B16 murine melanoma cell line is chosen as the target. B16 cells are incubated for 1 hour ex vivo with either Adtk or FGF-2Adtk prior to implantation intraperitoneally in BDF1 mice. Ganciclovir therapy is initiated in vivo, one day post tumor cell inoculation.

Figure 11:
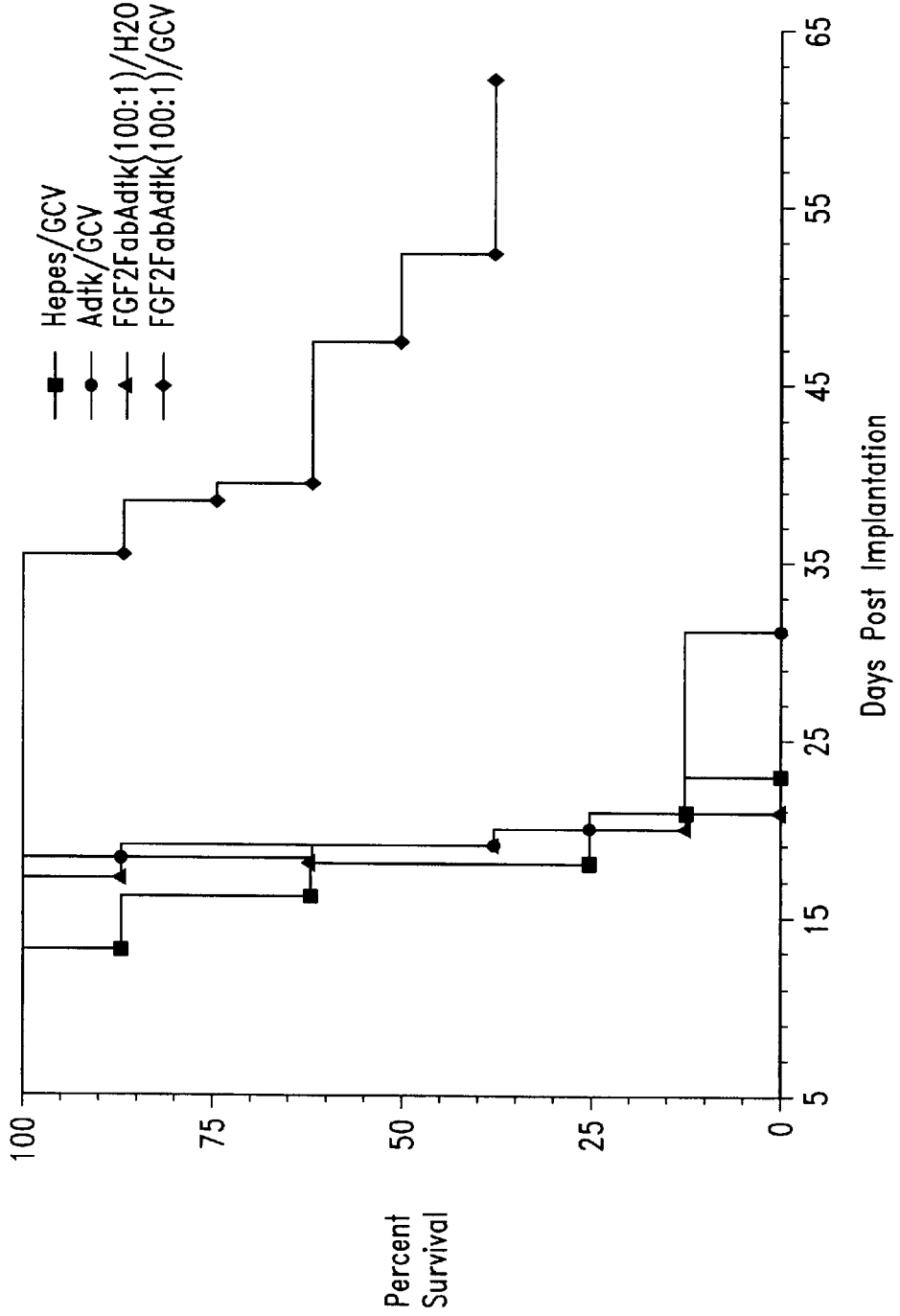
FIG. 11 shows a survival analysis of tumor bearing mice treated with either Adtk or FGF2-Adtk. B16 melanoma cells were treated ex vivo for one hour with either Adtk or FGF2-Adtk and then implanted intraperitoneally into BDF1 mice at 2×10e6 cells per mouse. Mice were then treated with either ganciclovir (GCV) or H$_2$O (as a control) for 14 days, i.p. Survival of tumor bearing mice treated with FGF2-Adtk and then administered ganciclovir was prolonged; such mice have a statistically prolonged survival compared to all other groups (p<0.001).

FIG. 11 shows a survival analysis of tumor bearing mice treated with either Adtk or FGF2-Adtk. B16 melanoma cells are treated ex vivo for one hour with either Adtk or FGF2-Adtk and then implanted intraperitoneally into BDF1 mice at $2 \times 10^6$ cells per mouse. Mice are then treated with either ganciclovir (GCV) or $H_2O$ (as a control) for 14 days, i.p. Survival of tumor bearing mice treated with FGF2-Adtk and then administered ganciclovir is prolonged; such mice have a statistically prolonged survival compared to all other groups ($p<0.001$).

The survival of mice bearing B16 melanoma treated with Adtk plus ganciclovir is indistinguishable from the control mice which received untreated B16 tumor cells plus the ganciclovir regimen (FIG. 11). In striking contrast, mice which received B16 melanoma treated with FGF2-Adtk demonstrated a 247% increase in median survival compared with control mice (FIG. 11).

Example 5

FGF2 Enhancement of Ad-Mediated Delivery of the HSVTK Gene in a Murine Model of Ovarian Cancer In a murine model of human ovarian carcinoma, an FGF2-redirected adenoviral vector carrying the gene for herpes simplex virus thymidine kinase (AdCMVHSV-TK) is shown to result in a significant prolongation of survival compared with the same number of particles of unmodified AdCMVHSV-TK. In addition, equivalent survival rates are achieved with a tenfold lower dose of the FGF2-redirected AdCMVHSV-TK compared with the unmodified vector. These findings suggest that strategies to enhance the efficiency of infection of adenoviral vectors may be of great clinical utility.

As described in previous examples, efficient gene delivery can be achieved via the use of tropism-modified Ad vectors specifically retargeted to receptors other than the primary receptor recognized by the knob domain of the Ad fiber. By complexing an Ad5 vector with a bispecific conjugate (Fab-FGF2), significant enhancement of gene delivery in four Kaposi's sarcoma cell lines has been demonstrated (see Example 1 above). To further delineate the therapeutic benefit to this approach, conjugates are constructed and utilized in a murine model of human ovarian cancer, as further described herein.

A. Methods

1. Cells and Viruses

The human ovarian carcinoma cell line SKOV3.ip1 is readily available from a variety of sources. Our supply is obtained from Janet Price (Baylor University, Houston, Tex.) and maintained in Dulbecco's modification of Eagle's medium (DMEM). 293 cells are purchased from the American Type Culture Collection, Rockville, Md. and maintained in DMEM/Ham's F-12 medium. (See also Graham, et al., *J. General Virol.* 36: 59–72 (1977).) The media are supplemented with 10% heat-inactivated fetal calf serum (FCS), glutamine (2 mM), penicillin (100 units/ml) and streptomycin (100 µg/ml) and the cells are propagated at 30° C. in a 5% $CO_2$ atmosphere. FCS is purchased from HyClone Laboratories, Logan, Utah and media and supplements are from Mediatech, Herndon, Va.

AdCMVLuc, an E1-, E3-deleted Ad5 vector which expresses firefly luciferase under the control of the CMV promoter, is provided by R. D. Gerard, University of Texas Southwestern medical Center, Dallas, Tex. (see Herz and Gerard, *PNAS USA* 90:2812–2816 (1993)). AdCMVlacZ, an E1-deleted Ad5 vector which expresses *E. coli* β-galactosidase from the CMV promoter is obtained from De-chu Tang (University of Alabama at Birmingham, Ala.). AdCMVHSV-TK has been described previously and is an E1-deleted Ad5 vector which expresses HSV-TK from the CMV promoter (see Rosenfeld et al., *Clin. Cancer Res.* 1:1571–1580 (1995)). The recombinant adenoviral vectors are propagated on the permissive 293 cell line and purified according to standard techniques (Graham and Prevec, "Manipulation of Ad Vectors," in *Methods in Molecular Biology Vol 7, Gene Transfer and Expression Techniques,* Murray and Walker (eds.), Humana Press, Clifton, 1991, pp. 109–128).

2. Generation and Characterization of Fab-FGF2 Conjugate

The Fab-FGF2 conjugate is constructed by conjugating the Fab fragment of 1D6.14, a neutralizing monoclonal antibody directed against the Ad5 knob, with an FGF2 mutein as described elsewhere herein. Analysis by mass spectrometry indicated that the conjugate contained a single molecule of FGF2 linked to a Fab fragment. The FGF2 component of the Fab-FGF2 conjugate retained the ability to bind its cognate receptor and stimulate endothelial cell proliferation. The Fab component of the Fab-FGF2 conjugate retained the ability to recognize trimeric Ad5 knob, as determined in an ELISA.

3. Assays of Adenoviral Infection in vitro

Preliminary experiments are performed as previously described herein to determine the optimal neutralizing dose of the 1D6.14 Fab fragment. Sixteen hours prior to infection, SKOV3.ip1 cells are seeded in 24-well plates at a density of 24,000 cells per well. Increasing dilutions of the Fab fragment are incubated with $10^8$ PFU of AdCMVLuc for 30 min at room temperature in a total volume of 20 µl HEPES-buffered saline (HBS). The vector is then diluted with DMEM/F-12+2% FCS (infecting medium) and 100 µl of the complexes are added at an MOI of 50 PFU per cell to the SKOV3.ip1 cells. After incubation for 1 h at 30° C., the infecting medium is aspirated and replaced with 1 ml of DMEM/F-12+10% FCS (complete medium). Following incubation for a further 24 h at 37° C., the cells are lysed and extracts are assayed for luciferase activity by a chemiluminescent assay (Promega, Madison, Wis.). The protein concentration of the lysates is determined in order to permit normalization of the data. The lowest dose of Fab which blocked infection is used in subsequent experiments. In addition, since the molar ratio of Fab to FGF2 in the conjugate is known to be 1:1, this value is used to calculate the optimal dose of Fab-FGF2 to be employed in subsequent retargeting experiments.

To determine the ability of the Fab-FGF2 conjugate to enhance adenovirus-mediated gene delivery, AdCMVLuc ($5 \times 10^7$ PFU) is preincubated with the optimal dose of the Fab fragment (1.44 µg) or Fab-FGF2 conjugate (1.94 µg) in 20 µl HBS for 30 min at room temperature. The vector or vector complexes are then diluted in infecting medium and 24,000 SKOV3.ip1 cells in 24 well plates are infected at an MOI of 50 PFU per cell in a final volume of 100 µl. Inhibition experiments are performed by adding a polyclonal anti-FGF2 antibody (Sigma, St. Louis, Mo.) to the AdCMVLuc-Fab-FGF2 complex prior to infection. Cell lysates are assayed for luciferase activity 24 h post-infection. The protein concentration of the lysates is determined in order to permit normalization of the data. Statistical analysis is performed using the Student t-test.

In order to quantitate the number of transduced cells, SKOV3.ip1 cells are infected with AdCMVLacZ. Sixteen hours prior to infection, SKOV3.ip1 cells are seeded in 6-well plates at a density of $3 \times 10^5$ cells per well. AdCMV-LacZ ($5 \times 10^7$ PFU) is preincubated with or without Fab-FGF2 (1.94 µg) in 20 µl HBS for 30 min at room temperature. The vector or vector-Fab-FGF2 complexes are then diluted in infecting medium and incubated with the SKOV3.ip1 cells at an MOI of either 5 or 50 PFU per cell in a final volume of 200 µl. After 1 h at 30° C., the infecting medium is aspirated, the cells are washed with PBS and 3 ml of complete medium are added to each well. Expression of β-galactosidase is determined 24 h post-infection by staining with the chromogenic substrate X-gal according to standard techniques. The cells are rinsed twice with PBS and fixed with 0.5% glutaraldehyde for 10 min at 37° C. Cells are then washed twice for 15 min with PBS containing 1 mM $MgCl_2$, after which they are stained with a PBS solution containing 5 mM $K_3Fe(CN)_6$, 5 mM $K_4Fe(CN)_6$, 1 mM $MgCl_2$ and 1 mg/ml X-gal (5-bromo-4 chloro-3-indolyl-beta-D-galactoside; Sigma). After removal of the X-gal solution, the cells are overlaid with 70% glycerol, and stored at 4° C.

4. In vivo Survival Experiment

Female SCID mice aged 6–8 weeks are obtained from the National Cancer Animal Program (Frederick, Md.), and received an intraperitoneal injection of $2 \times 10^7$ SKOV3.ip1 cells on day 0. In order to study the effects on survival, the mice are separated into 10 groups of 10 animals, except that the control group with tumor cells only contained 5 mice. On day 5, the treated groups are injected intraperitoneally with $2 \times 10^8$ or $2 \times 10^9$ PFU of AdCMVHSV-TK alone or AdCMVHSV-TK complexed with FGF2. Forty-eight hours later, half of the groups are treated with an intraperitoneal injection of ganciclovir (50 mg/kg bodyweight) for 14 days. The mice are monitored daily for survival. Survival differences between control and experimental groups are then compared and the statistical significance analyzed using the log-rank test.

B. Results and Discussion

Binding studies with $^{125}$I-labeled FGF are first performed in order to confirm that the target ovarian cancer cell line, SKOV3.ip1, possessed FGF receptors (data not shown). AdCMVLuc, an E1-, E3-deleted Ad5 vector which expresses firefly luciferase (Herz, et al., *PNAS USA* 90:2812–16 (1993)), is then premixed with the unconjugated anti-knob Fab fragment or the Fab-FGF2 conjugate prior to infection of SKOV3.ip1 call monolayers at a multiplicity of infection (MOI) of 50 plaque-forming units (pfu) per cell. Expression of luciferase activity in infected cells is determined 24 hours post-infection; this value is directly proportional to the number of infecting virus particles.

Figure 12:
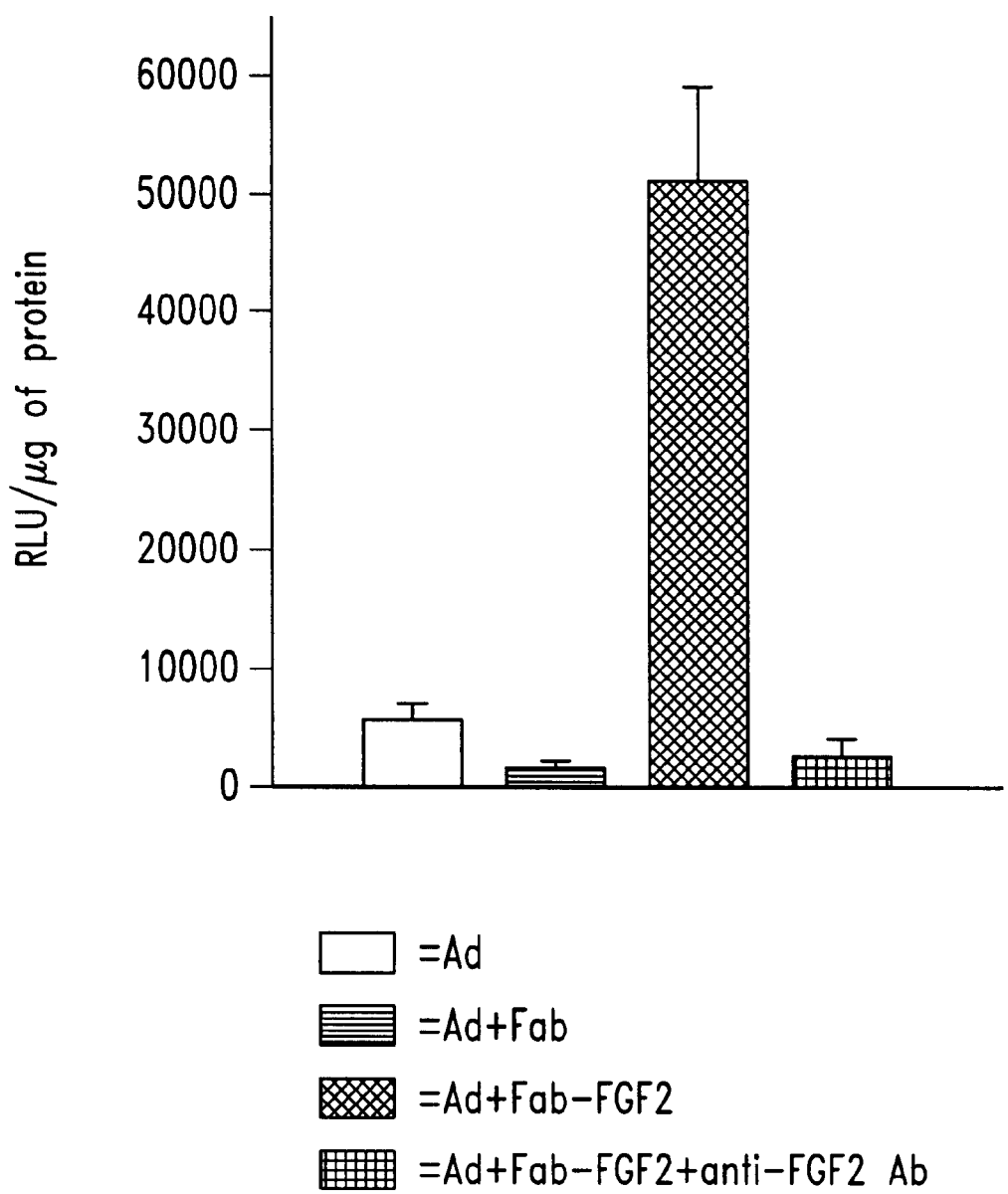
FIG. 12 illustrates the enhancement of Ad-mediated gene delivery by the Fab-FGF2 conjugate. AdCMVLuc (5×10$^7$ pfu) as preincubated with the optimal dose of the Fab fragment (1.44 μg) or Fab-FGF2 conjugate (1.94 μg) in 20 μL HBS for 30 min at room temperature. The vector or vector complexes were then diluted in DMEM/F-12+2% FCS and 24,000 SKOV3.ip1 cells in 24-well plates were infected at an MOI of 50 pfu/cell. Inhibition experiments were performed by adding a polyclonal anti-FGF2 antibody (Sigma, St. Louis, Mo.) to the Ad CMVLuc-Fab-FGF2 complex prior to infection. Cell lysates were assayed for luciferase activity 24 hours post-infection. The protein concentration of the lysates was determined to permit normalization of the data, which are expressed as relative light units (RLU) per microgram of cellular protein. Results are the mean±SD of triplicate experiments.

FIG. 12 illustrates the enhancement of Ad-mediated gene delivery by the Fab-FGF2 conjugate. AdCNVLuc ($5 \times 10^7$ pfu) as preincubated with the optimal dose of the Fab fragment (1.44 µg) or Fab-FGF2 conjugate (1.94 µg) in 20 µL HBS for 30 min at room temperature. The vector or vector complexes are then diluted in DMEM/F-12+2% FCS and 24,000 SKOV3.ip1 cells in 24-well plates are infected at an MOI of 50 pfu/cell. Inhibition experiments are performed by adding a polyclonal anti-FGF2 antibody (Sigma, St. Louis, Mo.) to the Ad CMVLuc-Fab-FGF2 complex prior to infection. Cell lysates are assayed for luciferase activity 24 hours post-infection. The protein concentration of the lysates is determined to permit normalization of the data, which are expressed as relative light units (RLU) per microgram of cellular protein. Results are the mean±SD of triplicate experiments.

As shown in FIG. 12, when AdCMVLuc is premixed with the Fab-FGF2 conjugate the level of luciferase activity is more than 9-fold greater than that achieved by the unmodified vector (p<0.0007). This enhancement of infection is specifically mediated by FGF2; gene delivery by the Ad-Fab-FGF2 complex is inhibited by anti-FGF2 antibody.

We next sought to investigate whether this FGF2-mediated enhancement in gene expression is due to infection of a greater percentage of target cells or to more gene copies per transduced cell. SKOV3.ip1 cell monolayers are infected at different MOIs with an E1-deleted Ad5 vector carrying the β-galactosidase reporter gene, AdCMVLacZ, in the presence or absence of Fab-FGF2.

Histological data indicate that FGF-2 mediated enhancement of Ad gene expression is the result of infection of a greater percentage of target cells. AdCMVLacZ ($5 \times 10^7$ pfu) is preincubated with or without Fab-FGF2 (1.94 µg) in 20 µL HBS for 30 min at room temperature. The vector or vector-Fab-FGF2 complexes are then diluted in DMDM/F-12+2% FCS and SKOV3.ip1 cells are infected at an MOI of 5 or 50 pfu/cell. Expression of β-galactosidase is determined 24 hours post-infection by staining with the chromogenic substrate X-gal. Tissues are examined from the following four groups: A: AdCMVLacZ, MOI=5; B: AdCMVLacZ-FGF2, MOI=5; C: AdCMVLacZ, MOI=50; and D: AdCMVLacZ-FGF2, MOI=50 (results not shown).

Twenty-four hours post-infection, the cells are stained with X-gal in order to demonstrate the expression of β-galactosidase. It is found that the Fab-FGF2 conjugate mediated Ad infection of a greater percentage of target cells than the native virus, permitting the transduction of a given number of target cells to be achieved by a lower dose of virus (results not shown).

It is well recognized that adenoviral vectors produce a dose-dependent inflammatory response in rodents and primates. Vector-associated toxicity has also been observed in human clinical trials and threatens to prevent the adenovirus from realizing its full potential as a vector for human gene therapy. This suggests that it would be advantageous to reduce the number of Ad particles required for a given level of gene transfer in vivo. Therefore, we sought to determine whether Fab-FGF2-mediated enhancement of Ad infection could be exploited for therapeutic advantage.

A murine model of human ovarian cancer is established as described previously by intraperitoneal injection of SCID mice with SKOV3.ip1 cells (Yu, et al., *Cancer Research* 53:891–8 (1993); Rosenfeld, et al., *J. Molec. Med.* 74:455–462 91996)). Five days later, the treated mice are injected intraperitoneally at two MOIs ($2 \times 10^8$ or $2 \times 10^9$ pfu) either with AdCMVHSV-TK, an E1-deleted Ad5 vector which expresses the prodrug-activating HSV-TK gene, or with AdCMVHSV-TK premixed with the Fab-FGF2 conjugate. Mice are then treated for 14 days with 50 mg/kg of the prodrug ganciclovir (GCV) or with an equivalent volume of serum-free medium. Ten animals are studied in each group. These animals are monitored daily and the length of survival of each mouse is recorded (FIG. 13).

Figure 13:
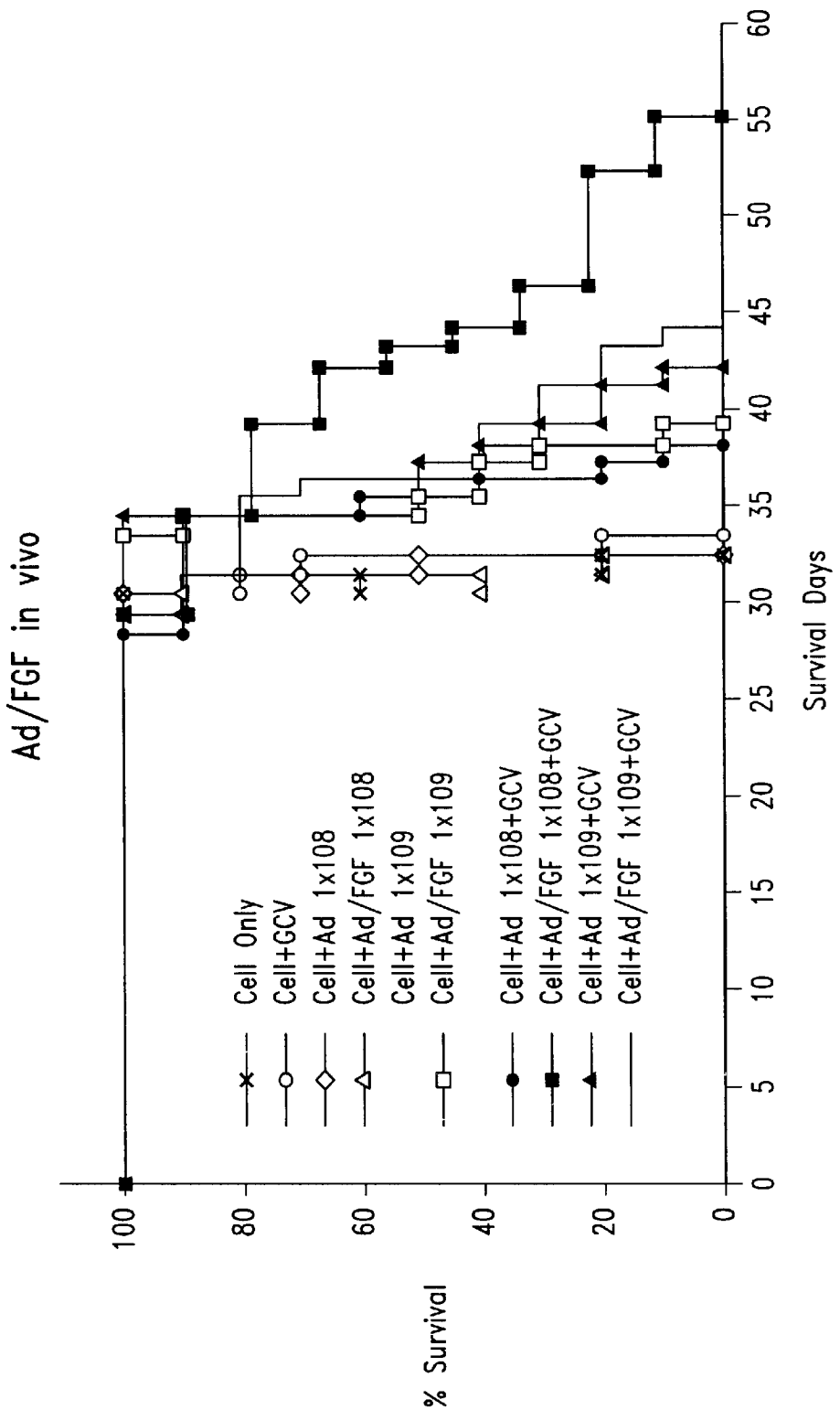
FIG. 13 illustrates the results of FGF2-enhancement of Ad-mediated expression of the HSV-TK gene, which augments therapeutic benefit in a survival experiment. A total of 95 female SCID mice aged 6–8weeks were inoculated intraperitoneally with 2×107 SKOV3.ip1 cells on day 0. On day 5, some mice were injected intraperitoneally with 2×108 or 2×109 pfu of AdCMVHSV-TK alone or AdCMVHSV-TK complexed with FGF2 (n=20 mice per group). Forty-eight hours later, half of the mice in each group (n=10) were treated daily with an intraperitoneal injection of ganciclovir (50 mg/kg bodyweight) for 14 days. Control groups consisted of mice which received no virus or GCV (n=5) or mice which were treated with GCV only (n=10). The mice were monitored daily for survival. The percentage of animals surviving is plotted against the number of days post tumor cell inoculation.

FIG. 13 illustrates the results of FGF2-enhancement of Ad-mediated expression of the HSV-TK gene, which augments therapeutic benefit in a survival experiment. A total of 95 female SCID mice aged 6–8weeks are inoculated intraperitoneally with $2 \times 107$ SKOV3.ip1 cells on day 0. On day 5, some mice are injected intraperitoneally with $2 \times 10^8$ or $2 \times 10^9$ pfu of AdCMVHSV-TK alone or AdCMVHSV-TK complexed with FGF2 (n=20 mice per group). Forty-eight hours later, half of the mice in each group (n=10) are treated daily with an intraperitoneal injection of ganciclovir (50 mg/kg bodyweight) for 14 days. Control groups consisted of mice which received no virus or GCV (n=5) or mice which are treated with GCV only (n=10). The mice are monitored daily for survival. The percentage of animals surviving is plotted against the number of days post tumor cell inoculation.

As expected, no significant increase in duration of survival over the group of untreated mice with tumors is observed for those animals treated with GCV alone (median survival=32 days). Nor is a survival advantage conferred in the absence of GCV by injection of either AdCMVHSV-TK or AdCMVHSV-TK premixed with Fab-FGF2. However, when considering treatment with ganciclovir, injection of the mice with AdCMVHSV-TK premixed with Fab-FGF2 is shown to result in a significant prolongation of survival time compared to injection with the same number of particles of unmodified AdCMVHSV-TK. Thus, when a viral dose of $10^8$ pfu is employed, the median survival of mice injected with AdCMVHSV-TK premixed with Fab-FGF2 is 37 days, compared with 35 days observed for the native virus (p=0.0025).

Similarly, at a viral dose of $10^9$ pfu, median survival is increased from 36 to 44 days when the efficiency of adenoviral infection is enhanced by Fab-FGF2 (p=0.0070). Of note, equivalent survival rates are achieved with a ten-fold lower dose of the redirected AdCMVHSV-TK compared to the unmodified vector (37 days for $10^8$ pfu AdCMVHSV-TK complexed with Fab-FGF2 vs. 36 days for $10^9$ pfu AdCMVHSV-TK; p=0.3760).

The fact that the Fab-FGF2 conjugate enhanced Ad infection by permitting infection of a greater percentage of cells rather than by producing more copies of the gene per cells is an important feature of this therapeutic modality. It has been reported that the antitumor effect of the HSV-TK/GCV cannot be augmented simply by increasing the HSV-TK enzyme levels per cell (Elshami, et al., *Cancer Gene Therapy* 4: 213–221 (1997)). In a study by Yee et al. exploring Ad-mediated gene delivery of HSV-TK in a murine ascites model of human breast cancer, a three-fold higher viral dose is employed in an attempt to increase survival (*Human Gene Therapy* 7: 1251–7 (1996)). However, they instead found that the higher dose led to substantial toxicity and more deaths.

In contrast, we have been able to augment the efficiency of the HSV-TK/GCV system by increasing the number of cells expressing the enzyme. These results thus demonstrate that the Fab-FGF2-mediated enhancement in Ad infection observed in vitro yielded a significant therapeutic benefit in vivo. Enhanced Ad delivery of the HSV-TK gene to the ovarian tumor cells resulted in an increase in host survival compared to an equal does of native vector. Moreover, the enhanced Ad infection permitted an equivalent therapeutic effect using a ten-fold lower dose of AdCMVHSV-TK. Thus, by permitting therapeutically significant levels of gene transfer while minimizing the toxicity associated with high numbers of virus particles, the foregoing example suggests that strategies to enhance the efficiency of infection of recombinant Ad vectors may be of general clinical utility.

Example 6

Assessment of Immunogenicity of Retargeted FGF2-ADV Complexes Compared to ADV

Adenoviral vectors have been shown to activate specific immune response. The host immune response is specific to adenoviral protein including the fiber knob protein. FGF2-retargeted Ad will be used as a strategy to blunt or block the antiviral immune response.

To evaluate adenoviral immunogenicity, mice are treated with $1 \times 10^9$ pfu of adenovirus alone or FGF2-retargeted adenovirus. The ratio of FGF-Fab to adenovirus is also varied in this experiment. A total of four groups with the total of number of animals in each group at 10 or 13. Group 1 animals received 200 μL of excipient (25 nM Tris pH 7.5, 100 mM NaCl, 10 mg/ml lactose) given by i.p. administration. Group 2 received adenovirus alone at $1 \times 10^9$ pfu in 200 μl i.p. Group 3 received FGF2-retargeted adenovirus at $1 \times 10^9$ pfu/200 μl i.p. injection with FGF2-Fab to adenovirus knob ratio of 30:1. Group 4 received FGF2-retargeted adenovirus at $1 \times 10^9$ pfu per 300 μl given i.p. with a FGF2-Fab to adenovirus knob ratio of 2000:1. Mice are checked and body weights are measured twice weekly.

On day 21 post i.p. injection, blood samples are collected from 5 of the animals from each of the four groups. The blood samples are put into an Eppendorf tube and allowed to clot. The samples are centrifuged and the serum is collected. Serum samples are assayed by ELISA for production of antibodies to adenoviral proteins and specifically to adenoviral knob protein.

A. ELISA Assays

1 Adenoviral ELISA Microtiter plates (96 well) are coated with adenovirus ($3 \times 10^8$ pfu in 100 μl per well) and incubated overnight at room temperature. The wells are rinse 3 times with PBS and then blocked with PBS+10% goat serum for 2 hours at room temperature. The wells are rinsed 3 times followed by addition of primary antibody at a dilution of 1:50. After 30 minutes at room temperature the wells are rinsed 3 times with PBS followed by addition of alkaline phosphatase anti-mouse Ig secondary. After 30 minutes the wells are rinsed with TBS (Tris buffered saline) followed by addition of PNPP substrate. Color reaction is allowed to occur for 60 minutes.

2. Adenoviral Knob Protein ELISA

Microtiter plates (96 well) are coated with 100 ng of knob protein in 100 ul per well and incubated overnight at room temperature. The wells are rinsed 3 times with PBS and then blocked with PBS+10% BSA for 2 hours at room temperature. The wells are rinsed 3 times followed by addition of primary antibody at a dilution of 1:50. After 30 minutes at room temperature the wells are rinsed 3 times with PBS followed by addition of alkaline phosphatase anti-mouse Ig secondary. After 30 minutes the wells are rinsed with TBS followed by addition of PNPP substrate. Color reaction is allowed to occur for 60 minutes.

B. Results

Figure 14:
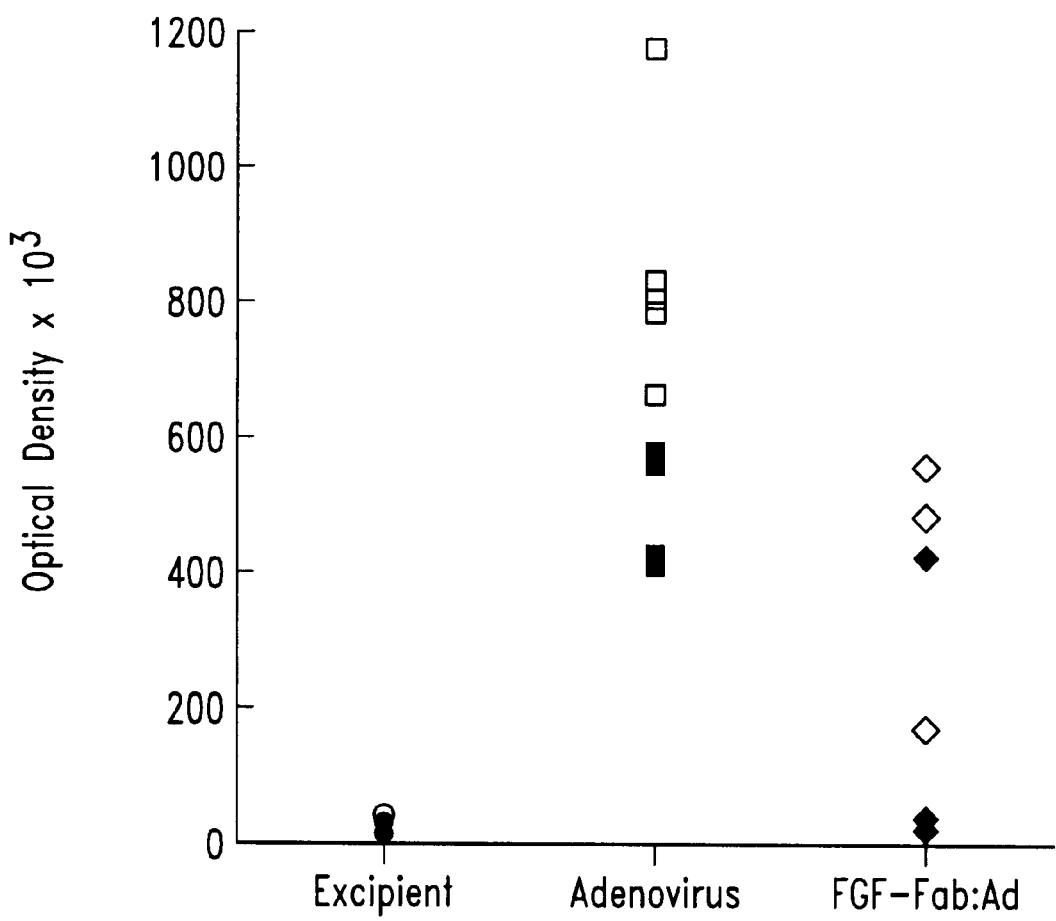
FIG. 14 illustrates antibody responses at day 21 following a single injection of excipient, adenovirus or FGF-Fab:Ad conjugate. Optical density (O.D.)×$10^3$ is plotted on the vertical axis, while data points corresponding to single injections of excipient, Ad, or FGF-Fab:Ad conjugate are identified on the horizontal axis. Open squares, circles and diamonds correspond to anti-adenovirus protein responses, while closed squares, circles and diamonds correspond to anti-knob protein responses.

FIG. 14 illustrates antibody responses at day 21 following a single injection of excipient, adenovirus or FGF-Fab:Ad conjugate. Optical density (O.D.)×$10^3$ is plotted on the vertical axis, while data points corresponding to single injections of excipient, Ad, or FGF-Fab:Ad conjugate are identified on the horizontal axis. Open squares, circles and diamonds correspond to anti-adenovirus protein responses, while closed squares, circles and diamonds correspond to anti-knob protein responses.

As shown, animals treated with excipient had a background response ranging from 14 to 43 with a median response of 33 optical density units. Animals treated with adenovirus developed a robust response to adenovirus proteins. Response varied from 1180 to 667 with a median response of 808 optical density units (see FIG. 14). Antibody response generated from the FGF2-retargeted adenovirus (at an FGF2-Fab:Ad ratio of 2000:1) is significantly reduced. Response varied from 556 to 38 with a median of 175 optical density units.

To determine the percentage of response derived from knob protein the antisera generated from all the treated groups are analyzed by knob ELISA. Animals treated with excipient had background responses varying from 28 to 21 with a median response of 24 optical density units. FIG. 14 also shows that animals treated with adenovirus had a significant response to knob protein ranging from 582 to 412 with a median response of 559 optical density units. Antibody response generated from the FGF2-retargeted adenovirus (at a FGF2-Fab: adenovirus ratio of 2000:1) is significantly reduced. Response varied from 422 to 24 with a median of 34 optical density units.

Therefore, it seems clear that retargeting of viral vectors using polypeptides reactive with the FGF receptor is a viable strategy, not only in the context of enhancing delivery and expression of a gene of choice, but in reducing the immunogenicity of the viral vector. Such retargeted vectors may well be more useful in producing systemic therapeutic effects in view of their reduced potential for stimulating an antibody response in an individual to which such vectors are administered in a therapeutic context.

Example 7

Enhanced Gene Delivery to Vascular Endothelial and Smooth Muscle Cells

Based on the rapidly expanding knowledge of the molecular bases of vascular pathology, delivery of therapeutic genes to the vasculature is a rational approach to the treatment of many diseases. Particular applications which have been suggested include atherosclerosis, coronary artery restenosis following angioplasty, peripheral vascular disease and primary pulmonary hypertension, as well as the neovascularization associated with tumor growth (Finkel T, et al., FASEB J. 1995; 9(10):843–851; Gibbons G H, et al., Science. 1996; 272(5262):689–693; Nabel E G, Circulation. 1995; 91(2):541–548; Isner J M, et al., Hum Gene Ther. 1996; 7(8):989–1011; Isner J M, et al., Lancet. 1996; 348 (9024):370–374; Rios C D, et al., Arterioscl Thromb Vasc Biol. 1995; 15(12):2241–2245; Rodman D M, et al., Am J Respir Cell Mol Biol. 1997; 16(6):640–649; Muller D W, et al., Circ Res. 1994; 75(6):1039–1049).

The nature of these disorders requires that effective gene therapy strategies must be based on direct in situ gene delivery. Thus, any proposed approach is dependent on a vector vehicle which is capable of achieving adequate gene delivery to target cells in vivo. Of the currently available vector systems, the adenovirus has a number of properties which make it a promising vector for in vivo applications (Brody S L, et al., Ann N Y Acad Sci. 1994; 716:90–101) and a number of gene therapy approaches for vascular diseases have been developed in model systems employing these vectors (Rios C D, et al., Arterioscl Thromb Vasc Biol. 1995; 15(12):2241–2245; Rodman D M, et al., Am J Respir Cell Mol Biol. 1997; 16(6):640–649; Muller D W, et al., Circ Res. 1994; 75(6):1039–1049; Harrell R L, et al., Circulation. 1997; 96(2):621–627; Lemarchand P, et al., Circ Res. 1993; 72(5):1132–1138; Steg P G, et al., Circulation. 1994; 90(4) :1648–1656; Rade J J, et al., Nat Med. 1996; 2(3):293–298; Feldman L J, et al., J Clin Invest. 1995; 95(6):2662–2671). In the vasculature however, where there are relatively low levels of cellular receptors for the adenovirus (Wickham T J, et al., J Virol. 1996; 70(10):6831–683), the concentration of viral particles required to achieve high levels of gene delivery is associated with a direct cytotoxic effect (Schulick A H, et al., Circ Res. 1995; 77(3):475–485; Schulick A H, et al., Circulation. 1995; 91(9):2407–2414).

Because viral toxicity is directly related to the dose of virus used (Schulick A H, et al., Circ Res. 1995; 77(3) :475–485; Crystal R G, et al., Nat Genet. 1994; 8(1):42–51), it would therefore be advantageous to achieve an adequate level of transfection with a lower dose of virus. Targeting adenoviral infection to an alternate receptor, which is highly expressed on vascular cells, thus appears to be an appropriate method for achieving this goal.

It has been demonstrated hereinabove that the tropism of the adenovirus can be altered using a retargeting strategy. As proof of concept, the Fab fragment of a neutralizing antibody against the adenoviral fiber knob domain (Louis N, et al., J Virol. 1994; 68(6):4104–4106; Henry L J, et al., J Virol. 1994; 68(8):5239–5246) (which binds to the recently identified cellular adenoviral receptor (Bergelson J M, et al., Science. 1997; 275(5304):1320–1323, Tomko R P, et al., Proc Natl Acad Sci USA. 1997; 94(7):3352–3356; Hong S S, et al., EMBO J. 1997; 16(9):2294–2306)) is conjugated to folate (Douglas J T, et al., Nat Biotech. 1996; 14:1574–1578). This conjugate is then used to retarget adenoviral infection specifically via the folate receptor (Douglas J T, et al., Nat Biotech. 1996; 14:1574–1578).

A similar strategy is then employed to direct adenoviral infection to the fibroblast growth factor (FGF) receptor using basic FGF (FGF2) as the targeting ligand (Goldman C K, et al., Cancer Res. 1997; 57(8):1447–1451). Using this approach, the transfectability of Kaposi's sarcoma cells, which possess low levels of adenoviral fiber receptors but high levels of FGF receptors, is greatly enhanced. As a rational extension of this approach, in the present study we chose to use FGF2 as our targeting ligand for vascular gene delivery, taking advantage of the knowledge that vascular cells express FGF receptors (Asahara T, et al., *Circulation*. 1995; 92(9 Suppl):II365–371; Sosnowski B A, et al., *J Biol Chem*. 1996; 271(52):33647–33653). In this way, we are able to achieve significant enhancement of gene delivery to vascular endothelial and smooth muscle cells, thus enabling a given level of gene expression to be achieved with a lower concentration of virus particles. Therefore, this strategy may ultimately improve the clinical utility of adenoviral vectors by allowing effective gene delivery in vivo at viral concentrations below those that result in toxicity.

A. Methods

1. Cell Culture

Primary cultures of human umbilical vein endothelial cells (HUVECs) are obtained from the laboratory of Dr F. M. Booyse, (University of Alabama at Birmingham, Birmingham, Ala.). These cells are obtained from umbilical cords as previously described (Booyse F M, et al., *Blood*. 1981; 58:788–796.) and grown on a 1% gelatin coating in Media 199 (Cellgro, Herndon, Va.) containing 10% heat inactivated fetal bovine serum (FBS; Hyclone Laboratories, Logan, Utah), penicillin (100 I.U./mL; Cellgro), streptomycin (69 mmol/L; 100 mg/mL; Cellgro), glutamine (2 mmol/L; Cellgro), heparin (10 U/mL; Elkins-Sinn Incorporated, Cherry Hill, N.J.), insulin (1.4 mmol/L; 10 mg/mL), transferrin (0.13 mmol/L; 10 mg/mL) and sodium selenite (0.06 mmol/L; 10 ng/mL) (purchased from Becton Dickson Labware (Bedford, Mass.) as ITS stock) and endothelial mitogen (0.1 mg/mL; Biomedical Technologies, Stoughton, Mass.).

Primary cultures of human coronary artery endothelial cells (HCAECs) are purchased from Clonetics Corporation (Walkersville, Md.) and grown on 1% gelatin coating in EBM-2 media (Clonetics Corporation) containing EGM-2 MV supplements—FBS (5%), hydrocortisone, human fibroblast growth factor, vascular endothelial growth factor, R3-insulin growth factor-1, ascorbic acid, human endothelial growth factor, gentamycin and amphotericin.

Primary cultures of human aortic smooth muscle cells (HASMCs) are obtained from the American Type Culture Collection (Rockville, Md.) and grown on uncoated flasks in Ham's F12 media (Cellgro) containing 10% heat inactivated FBS (Hyclone), glutamine (2 mmol/L), endothelial mitogen (0.02 mg/mL, Biomedical Technologies), insulin (1.4 mmol/L; 10 mg/mL), transferrin (0.13 mmol/L,10 mg/mL) and sodium selenite (0.06 mmol/L, 10 ng/mL) (Becton Dickson Labware).

All cells are maintained at 37° C. in a humidified atmosphere containing 5% $CO_2$.

2. Adenoviral Vectors A recombinant E1A-deleted adenovirus expressing firefly luciferase under the control of the cytomegalovirus (CMV) promoter (AdCMVLuc (Herz J, et al., Proc Natl Acad Sci USA. 1993; 90(7):2812–2816)) is propagated in the permissive 293 cell line, purified by centrifugation through two cesium chloride gradients and plaque titered on 293 cells by standard techniques (Graham F, et al., *Methods in Molecular Biology*. Vol. 7—Gene Transfer and Expression Techniques. Clifton, N.J.: Humana Press; 1991:pp. 109–129). A recombinant E1A-deleted adenovirus expressing the *Escherichia coli* β galactosidase gene under the control of the cytomegalovirus promoter (AdCMVLacZ) is prepared as above. An irrelevant virus (AdAmpg, which encodes the genes for retroviral packaging functions) is used as a control in the galactosidase experiments.

3. 1D6.14 Fab-FGF2 Conjugate

The Fab-FGF2 is constructed by conjugating recombinant FGF2 (Lappi D A, et al., *Anal Biochem*. 1993; 212(2):446–451) with the Fab fragment of a neutralizing monoclonal antibody (1D6.14) generated against the adenovirus serotype 5 knob region (Douglas J T, et al., *Nat Biotech*. 1996; 14:1574–1578). The conjugation procedure and subsequent confirmation of the activity of the Fab and FGF2 components of the conjugate have been described elsewhere (Goldman C K, et al., *Cancer Res*. 1997; 57(8):1447–1451). Briefly, conjugation is performed using N-succinimidyl 3-(2-pyridyldithio)propionate (SPDP; Pharmacia, Uppsala, Sweden) followed by purification using heparin-Sepharose and Sepharose S-100 column chromatography (Pharmacia). Mass spectrometry of the resulting conjugate indicated a 1:1 molar ratio of Fab to FGF2. Activity of the Fab and FGF2 components is confirmed by enzyme-linked immunoassay and cellular proliferation assay. In brief, ELISA plates are coated with recombinant adenovirus knob protein, Fab-FGF2 conjugate is applied to the plates, then bound conjugate is detected using an anti-FGF antibody. FGF activity of the conjugate is confirmed with a proliferation assay using bovine endothelial cells.

4. Adenoviral Infections

To properly evaluate the effects of FGF2 retargeting, we aimed to concurrently ablate native viral tropism and redirect infection via FGF2. Therefore, preliminary experiments are conducted to determine the optimal Fab-FGF2 to adenovirus ratio which would achieve this. Firstly, the dose of Fab required to block infection via the native receptor is determined by titration. The lowest dose of Fab which maximally blocked infection (implying all Fab binding sites on the virus are occupied) is determined by luciferase assay (see below) and chosen as the basis for subsequent calculations (data not shown). We then used the same molar ratio of Fab-FGF2 to virus as the optimized Fab to virus ratio, based on the fact that the conjugate contained a 1:1 ratio of Fab: FGF2. For analysis of transfection, cells are harvested by trypsinization, assessed for viability by trypan blue exclusion and plated into 24 well plates at a density of 24,000 cells per well.

Twenty four hours later, cells are infected with adenoviral vector. AdCMVLuc ($5 \times 10^6$ plaque forming units (pfu) in 1 ml, diluted from stock in HEPES-buffered saline(HBS; 150 mmol/L HEPES, 20 mmol/L NaCl, pH 7.8) is mixed with Fab (0.2 mg) or Fab-FGF2 (0.27 mg) in 1.5 mL polypropylene microcentrifuge tubes and incubated at room temperature for 30 minutes in a total volume of 5 ml. For experiments in which different concentrations of virus are used, the amount of Fab or Fab-FGF2 is adjusted to keep the proportions constant. For blocking studies, 2 ml of a rabbit polyclonal anti-FGF antibody (Sigma Chemical Co) or 10 mg of soluble recombinant FGF receptor extracellular domain (Austral Biologicals, San Ramon, Calif.), are added to the tube and followed by a further incubation of 30 min at room temperature.

Just prior to infection, the volume of each mixture is brought to 350 ml with warmed (37° C.) DMEM/F12 (50:50) media (Cellgro) containing 2% FBS, glutamine, penicillin and streptomycin. Blocking with excess FGF2 is performed by preincubating cells for 30 min with a 100 fold excess of free FGF2 (compared to the amount in the conjugate) as well as including this amount of FGF2 in the infecting media. Blocking with heparin is performed by using a concentration of 500 U/ml in the infecting media (i.e. 50-fold excess compared to the concentration of heparin in the HUVEC propagation medium). Complete media are removed from the cells and replaced with the virus-containing media, 100 ml per well in triplicate. Trays are incubated at 37° C. in 5% $CO_2$ atmosphere for 1 hour, then the infecting media are aspirated, cells are gently washed once with Dulbecco's phosphate buffered saline (D-PBS, Cellgro) and 500 ml of the appropriate complete media are added to the wells. Cells are incubated a further 24 hours, then luciferase reporter gene expression is assayed.

5. Luciferase Assay

Luciferase expression is analyzed using a Luciferase Assay System kit (Promega, Madison Wis.), according to the manufacturer's instructions. Briefly, media are aspirated from cells, cells are washed with PBS, then lysed in Promega cell lysis buffer (100 ml per well). Twenty microliters of lysate are added to 100 ml of Promega luciferase assay reagent and determinations of relative light units (RLU) are made using a Berthold luminometer calibrated to ensure the RLU readout is within the linear range of the system.

6. β-galactosidase Assay

For analysis of β galactosidase gene expression, AdCMVLacZ is complexed with Fab or Fab-FGF2 in the manner described for AdCMVLuc, then cells are infected as above. Beta-galactosidase activity is assessed 48 hours later. Media are removed from cells and cells are washed once with PBS, then fixed in 0.5% glutaraldehyde for 10 mins. Following 2 washes with 10 mM magnesium chloride, cells are stained overnight at room temperature in the dark with a solution containing 1 mg/mL X-gal (GibcoBRL, Grand Island N.Y.). Negative controls included staining of uninfected cells and staining of cells infected with an irrelevant virus (AdAmpg). The number of stained versus total cells are counted in three random high power (100×) fields.

Beta-galactosidase expression is also assessed by fluorescent activated cell sorting (FACS) analysis. For these experiments, cells are plated at 100,000 cells per well in six well plates, then infected with adenovirus alone or adenovirus-Fab-FGF2 complexes, prepared as above. After 48 hours, cells are harvested by trypsinization, resuspended in a solution of 10 mmol/L HEPES, 4% FCS in D-PBS (referred to as staining medium) at 100,000 cells in 100 ml in 6 mL FACS tubes. Cell suspensions are warmed for 10 minutes at 37° C., 100 ml of 2 mmol/L fluorescein di-galactopyranoside (FDG; Sigma Chemical Company) is added, then the reaction stopped after one minute with the addition of 500 ml of ice cold staining medium, then 500 ml cold 2% paraformaldehyde, followed by analysis using a Becton-Dickson FACScaliber machine.

7. Tritiated Adenovirus Binding Assay

A binding assay using $^3$H labeled adenovirus is performed as described (Wickham T J, et al., *J Virol*. 1996; 70(10) :6831–6838). Briefly, cells are harvested from confluent 80 $cm^2$ flasks with Versene (GibcoBRL) and resuspended at a density of $10^7$ cells per mL. $^3$H-AdCMVLuc (10,000 cpm, specific activity $1.5 \times 10^{-5}$ counts per particle) is incubated with Fab, Fab-FGF2 or Fab-FGF2+anti FGF antibody, as described above, then added to $10^6$ cells in a final volume of 200 ml of Dulbecco's Modified Eagle's Media (DMEM; Cellgro), 10 mmol/L HEPES, 1 mmol/L magnesium chloride. Cell suspensions are shaken at 4° C. for 1 hour, washed with 4 mL cold D-PBS/0.1% bovine serum albumen then centrifuged at 1500 rpm for 10 minutes The cell pellet is resuspended in 200 ml D-PBS/0.1% bovine serum albumen and transferred into 5 mL scintillation fluid for counting in a scintillation counter (Packard, 1900TR liquid scintillation analyzer).

8. FACS Analysis for FGF Receptors

HUVECs are harvested by trypsinization, washed twice with cold (5° C.) D-PBS, then fixed with 1% paraformaldehyde for 30 minutes on ice. Following two washes with cold D-PBS, cells are resuspended in D-PBS (200,000 cells in 100 ml), then a monoclonal antibody against FGF receptors (EcR6, PRIZM Pharmaceuticals, San Diego Calif.) is added to a final concentration of 50 mg/mL and incubated for 30 minutes on ice. This antibody is chosen because the epitope it recognizes has been mapped to a region shared by all four described FGF receptors. Controls consisted of mouse IgG (Sigma) and no primary antibody. Following two D-PBS washes, goat anti-mouse FITC labeled secondary antibody (Jackson Immunoresearch Laboratories Inc., West Grove Pa.) is applied at 1:100 dilution in D-PBS, for 30 minutes on ice, then cells are washed twice with D-PBS, resuspended in 1% paraformaldehyde and analyzed using a Becton-Dickson FACScaliber machine.

9. Statistical Analysis

Comparisons between different vector groups are made using single factor ANOVA and Student's t-test, with significance accepted at $p<0.05$.

B. Results and Discussion

1. FGF2 Retargeting of Adenovirus Enhances Gene Expression in HUVECs

Figure 15A:
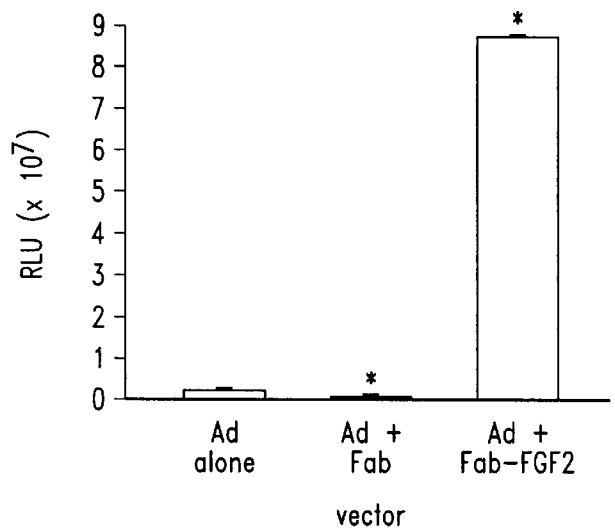
FIG. 15A shows that FGF2 retargeting of adenoviral infection results in increased transgene expression. HUVECs were infected with AdCMVLuc alone, AdCMVLuc+Fab, or AdCMVLuc+Fab-FGF2, and luciferase expression was measured 24 hours later. A representative graph of 3 separate experiments is shown. Data is mean+/−SD. * $p<0.001$ vs. Ad alone.

The adenovirus is a promising vector for in situ gene delivery to the vasculature. However, the achievement of high levels of transduction of vascular cells in vivo is limited by target cell cytotoxicity at high concentrations of virus. Therefore, we aimed to develop a strategy which would enable a reduction in the concentration of adenoviral vector necessary to achieve a given level of transfection. Because the level of native adenoviral receptors on vascular cells is relatively low, it is hypothesized that enhanced gene delivery could be achieved by targeting adenoviral infection to an alternate receptor, the FGF receptor, which is expressed on vascular cells. To explore this possibility, HUVECs are transfected with AdCMVLuc alone or following incubation of the virus with a retargeting conjugate, which is formed by linking FGF2 to the Fab fragment of a neutralizing antibody directed against the adenoviral fiber knob domain. As a control to confirm binding of the Fab to the virus, cells are also infected with virus which had been incubated with Fab alone. Twenty four hours later, luciferase reporter gene expression, which is proportional to the number of infecting virus particles, is assessed. Transfection with AdCMVLuc is inhibited 87±3% (mean±SD of three experiments) by 1D6.14 Fab, thus confirming the stability of Fab binding to adenoviral knob in these experiments. Transfection with the adenovirus-Fab-FGF2 complex resulted in a significant 32.4±6.6 fold enhancement of luciferase expression compared to infection with virus alone (mean±SD of three experiments. FIG. 15A). The substantial improvement in gene expression supported our hypothesis that adenovirally mediated gene delivery could be enhanced by targeting via FGF2. Further experiments to confirm that this effect resulted from genuine retargeting mediated by FGF2 are then conducted.

2. Enhanced Gene Expression is Mediated by Increased Binding of Ad to Cells

Figure 15B:
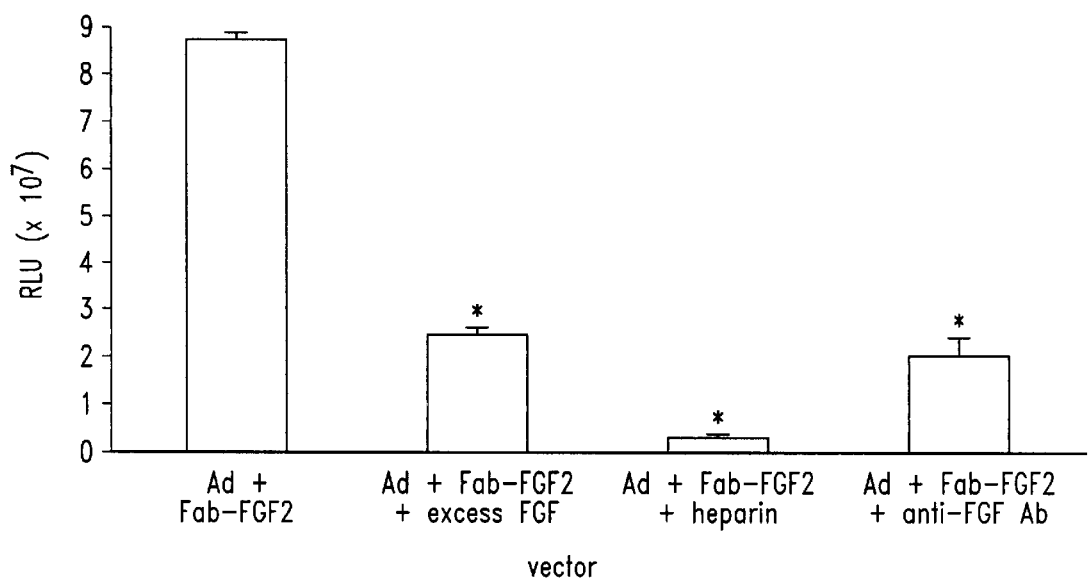
FIG. 15B shows the blocking of FGF2 retargeting. HUVECs were infected with AdCMVLuc+Fab-FGF2 alone or blocked with an anti-FGF antibody, heparin or excess free FGF. * $p<0.001$ vs. Ad+Fab-FGF2.

To investigate whether the enhancement in adenovirus mediated gene delivery is specifically mediated by FGF2, the Fab-FGF2 retargeted virus is incubated with a polyclonal antibody against FGF, an excess of free FGF2, or with heparin (which binds to FGF) prior to infection of HUVECs. Transfection is inhibited by each of these reagents; 82±4%, 41±29%, and 97±0.6% respectively (means±SD of three experiments), confirming that the enhancement is specifically mediated via FGF2 (FIG. 15B).

In a separate experiment, inhibition of 77%±4% (mean±SD of triplicate determinations) is also seen by incubating the adenovirus-Fab-FGF2 complex with soluble FGF receptor (data not shown). Importantly, neither heparin nor excess FGF2 had any effect on transfection by adenovirus alone. It is theoretically possible that the enhancement seen with the adenovirus-Fab-FGF2 complex could have been due to either a change in adenoviral binding, as we proposed, or due to a stimulatory effect of FGF2 per se, although the lack of enhancement with excess free FGF2 suggested the latter is not the case.

Figure 15C:
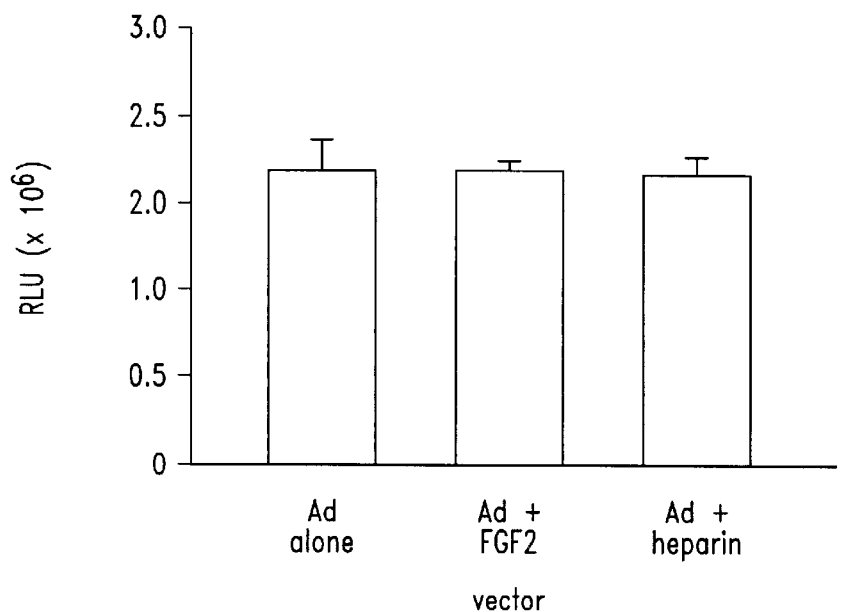
FIG. 15C shows that enhanced gene expression is seen with FGF2. HUVECs infected with Ad alone or in the presence of heparin or FGF2 at an equimolar concentration to that used for Fab-FGF2 retargeting.
Figure 15D:
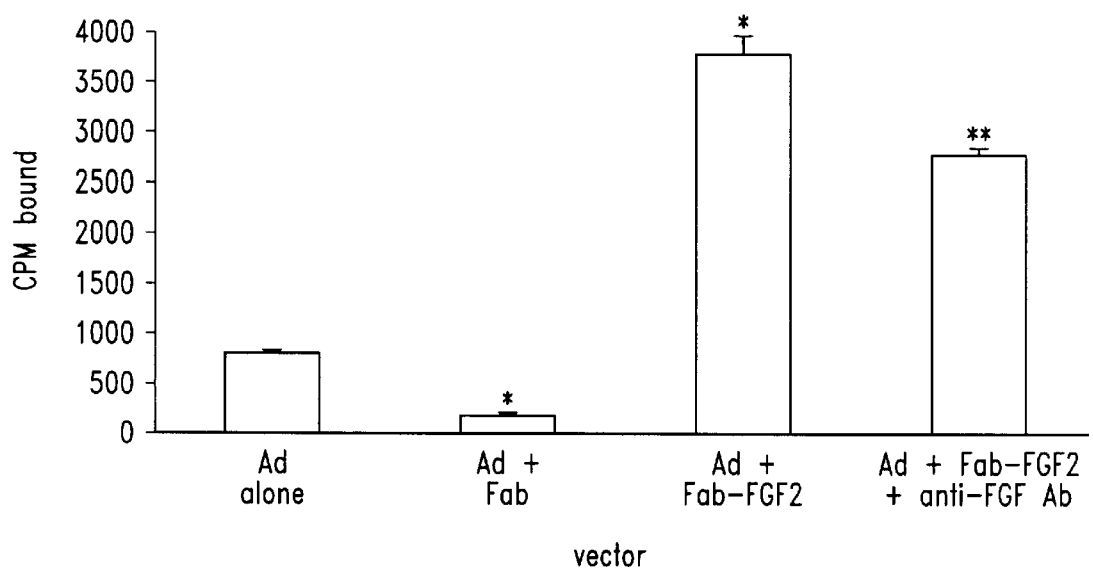
FIG. 15D illustrates the results of a tritiated binding assay. Tritiated AdCMVLuc alone or following incubation with Fab, Fab-FGF2 or Fab-FGF2+antiFGF antibody was bound to cells at 4 degrees for 1 hr. Following washing, residual bound radioactivity (counts per minute, cpm) was measured in a scintillation counter. * $p<0.001$ vs. Ad alone, ** $p<0.001$ vs. Ad+Fab-FGF2.

However, to answer this question more specifically, cells are infected with adenovirus alone or in the presence of an equimolar amount of free FGF2 to that contained in the dose of conjugate used for retargeting. Results show that this dose of free FGF2 alone had no effect on adenoviral transduction (FIG. 15C). Therefore, the enhancement seen is not due to a stimulatory effect of FGF2. To confirm that the enhancement of transduction seen with Fab-FGF2 is due to enhanced adenoviral binding, a binding assay using $^3$H-labeled adenovirus is performed. This assay is performed using HUVECs harvested from confluent 75 cm$^2$ flasks. Results show an enhancement of binding of radiolabeled virus to HUVECs when the virus is complexed to Fab-FGF2 as compared to virus alone (FIG. 15D). Taken together, these results confirm that the enhancement in gene expression observed is likely due to increased binding of adenovirus when retargeted via FGF2. Thus, these findings support the hypothesis that the transduction of endothelial cells can be improved by targeting Ad via a heterologous receptor.

3. FGF2 Retargeting Enhances Ad-mediated Gene Expression in Coronary Artery Endothelial and Vascular Smooth Muscle Cells To further explore the potential of FGF2 retargeting of adenovirus for enhanced vascular gene delivery, and to ensure the effects we noted are not peculiar to HUVECs, we investigated the effect of FGF2 retargeting on gene delivery to primary cultures of human coronary artery endothelial cells and human aortic smooth muscle cells. Cells are infected in triplicate as previously described, and three experiments are performed for each.

Figure 16A:
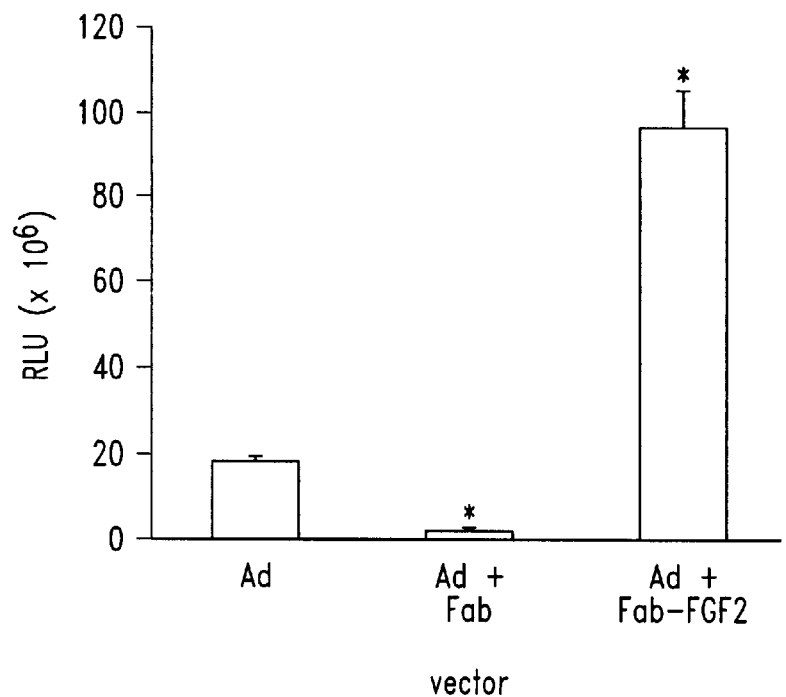
FIGS. 16A–B illustrate that Fab-FGF2 retargeting enhances gene expression in HCAECs and HASMCs. HCAECs (FIG. 16A) and HASMCs (FIG. 16B) were infected with AdCMVLuc alone, AdCMVLuc+Fab, or AdCMVLuc+Fab-FGF2, and luciferase expression was measured 24 hours later. A representative graph of three experiments is shown. Data is mean+/−SD. * $p<0.001$ FIG. 17 describes the determination of the enhancing effect of FGF2 retargeting at different viral doses. HUVECs were infected with AdCMVLuc at a dose of 10, 50 or 100 pfu/cell with or without Fab-FGF2 retargeting. Luciferase assay was performed 24 hours later. Results are mean+/−SD.
Figure 16B:
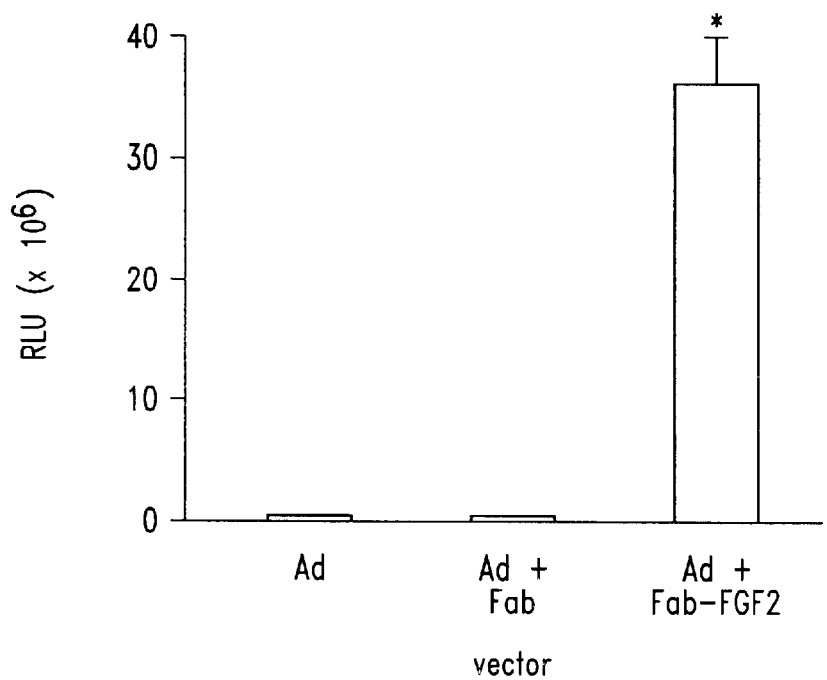

Transduction of these cells is significantly enhanced by Fab-FGF2. Results in the endothelial cells showed an enhancement of 4.55+/−1.3 fold (mean+/−SD, p<0.01) compared to adenovirus alone and an even greater enhancement of 92.6+/−2.6 fold (mean+/−SD, p<0.01) in the smooth muscle cells. (FIGS. 16A–B). These findings provide additional evidence that FGF2 retargeting of adenoviral infection is a useful strategy to enhance gene delivery to relevant vascular cells.

4. FGF2 Retargeting of Adenovirus Allows a Reduction in Adenoviral Dose

Because our primary goal is to provide a means to reduce adenoviral dose as a way of avoiding cytotoxicity, we next sought evidence that the enhancement in gene expression seen with FGF2 retargeting would enable a reduction in the dose of virus necessary to achieve the same level of transgene expression. HUVECs are infected with AdCMVLuc at a dose of 10, 50 or 100 pfu/cell with or without Fab-FGF2.

Figure 17:
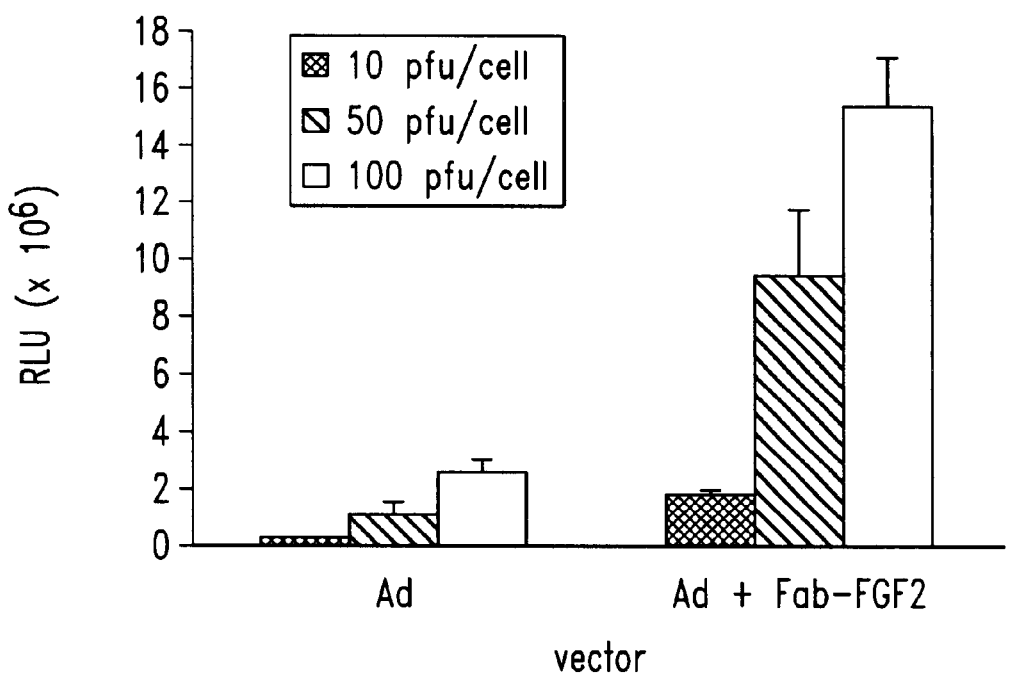
Figure 19:
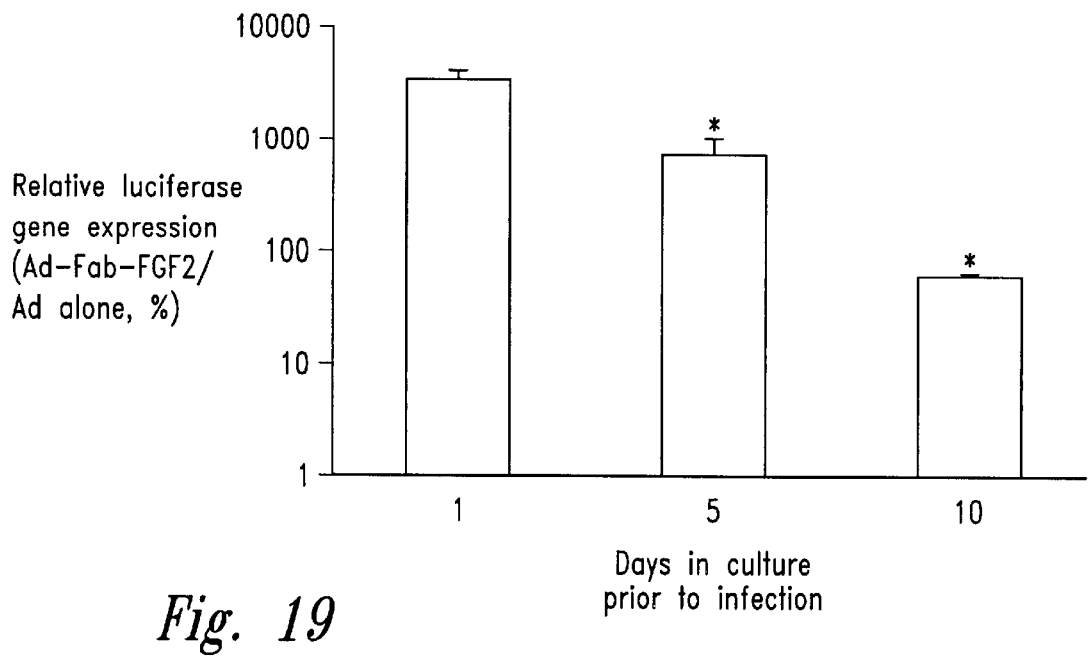
FIG. 19 illustrates the reduction of FGF2 enhancement of gene delivery in quiescent cells. HUVECs were plated and maintained in culture for 1, 5 or 10 days. Cells were then infected with AdCMVLuc (50 pfu/cell) or AdCMVLuc+Fab-FGF2 and luciferase assay was performed 24 hours later. Data are expressed as the ratio of luciferase expression in the cells infected using Fab-FGF2 retargeting, compared to corresponding cells plated at the same time and infected with AdCMVLuc alone. Bars represent mean±SD of three experiments. *=$p <0.01$ vs. 1 day in culture.

A luciferase assay performed 24 hours later showed an approximately equivalent level of transduction using 10 pfu/cell with FGF2 retargeting as is seen with 100 pfu/cell when virus alone is used (FIG. 17). We recognized however, that the enhanced luciferase reporter gene expression seen with FGF2 retargeting could potentially either be due to greater expression per cell, or to a greater number of transduced cells, or both. Therefore the number of transduced cells is determined by infection with AdCMVLacZ with or without Fab-FGF2 and assessing β-galactosidase expression by staining and counting of cells.

These experiments demonstrate a greater number of transduced cells for the same dose of virus when using Fab-FGF2 retargeting (not shown). Data gathered using HUVECs indicated that transfection with unmodified adenovirus at a dose of 50 pfu/cell led to a transfection efficiency of 10% which is increased to 100% with FGF2 retargeting at the same concentration of virus. For smooth muscle cells, the relative enhancement is even greater, with a transfection efficiency of <1% by the unmodified virus increasing to 100% with FGF retargeting.

Analysis is also performed by assessing transduction with AdCMVLacZ at 10, 50 or 100 pfu/cell with or without Fab-FGF2 followed by FDG staining and FACS analysis. This analysis confirms that FGF2 retargeting resulted in both an increase in the number of transduced cells as well as an increase in the amount of expression per cell, even if 100% transduction had been achieved with adenovirus alone (data not shown). These experiments confirm that a lower dose of virus can achieve the same degree of reporter gene expression when retargeted via FGF2 and illustrate that the effect occurs across a range of viral doses.

5. Enhancement of Gene Delivery by FGF Retargeting is Greater in Proliferating Cells Because we are retargeting to a receptor which is known to be upregulated in the context of proliferation and tissue injury in vivo (Casscells W, et al., *Proc Natl Acad Sci USA*. 1992; 89(15):7159–7163; Yamada K, et al., Acta Neurochirurgica—Supplementum. 1994; 60:261–264; Lindner V, et al., *Circ Res*. 1993; 73(3):589–595) and organ culture in vitro (Daley S J, et al., *Am J Pathol*. 1996; 148(4):1193–1202), we wished to assess whether there is any detectable difference between the relative enhancement in gene transfer with FGF2 retargeting in proliferating versus quiescent cells in vitro and whether any differences correlated with levels of FGF receptor expression. We therefore attempted to downregulate FGF receptor expression by maintaining HUVECs in confluent culture for 5 or 10 days, then compared the effect of FGF2 retargeting in these cells to the results seen with cells which had been in non-confluent culture for 24 hours only (as described above).

Confluent cultures are prepared by plating cells at 24,000 per well in 24 well plates, then allowing them to reach confluence with no further feeding (to day 5) or with one change of media only (on day 5 for those cells maintained for 10 days). Under these conditions, at 5 and 10 days the cells appeared relatively quiescent as evidenced by a total lack of mitotic figures, but good viability is maintained (good morphology, no evidence of cell death). Cells are then infected with AdCMVLuc with or without FGF2 retargeting and fresh complete media is added to the wells.

A luciferase assay is performed 24 hours later. Results are expressed as a ratio of the gene expression seen in the cells infected with retargeted adenovirus, compared with cells plated at the same time which are infected with unmodified virus (data not shown). In this way we corrected for any factors which might impact on adenoviral transduction per se with extended time in culture (e.g. cellular metabolic rate).

The data indicate that with progressively longer time in culture, the enhancing effect of FGF2 retargeting is reduced, such that by day 10, FGF2 retargeting actually led to a relative reduction of 54+/−6% in gene expression compared to adenovirus alone. Even at this time point however, the level of transduction with Fab-FGF2 retargeting is still greater than that seen when infection is blocked with Fab (data not shown), indicating that a degree of FGF2 retargeted infection is still taking place.

Once it became apparent that the FGF2 retargeting strategy is mediated by FGF2 binding to cells, we sought to investigate whether the reduction in enhancement we saw in the confluent cells could be explained at least in part by a relative reduction in FGF receptor expression in these cells, as has been reported for quiescent cells in vivo (Casscells W, et al., *Proc Natl Acad Sci USA*. 1992; 89(15):7159–7163; Lindner V, et al., *Circ Res*. 1993; 73(3): 589–595).

To investigate this, FACS analysis for FGF receptors is performed using rapidly proliferating cells and cells maintained in confluent culture as above. We used a monoclonal anti-FGF receptor antibody (EcR6) which recognizes a common epitope shared between all four described FGF receptor subtypes, and negative controls consisting of cells incubated with mouse IgG or no primary antibody. Using this technique we are able to detect a 60% reduction in the proportion of cells staining positively for FGF receptors in the cells maintained at confluence for 10 days compared to the non-confluent cells (data not shown). These data thus show a trend which is consistent with the published in vivo reports and provide evidence for a correlation between retargeted gene transfer and the level of expression of the targeted receptor.

6. Discussion

Our established retargeting strategy has been further expanded to achieve an increase in adenoviral mediated gene delivery to vascular cells. The goal of reducing the concentration of virus required for a given level of transduction has now been achieved. These findings are relevant to the clinical implementation of gene therapy because adenoviral vectors can cause direct cytotoxic effects at high doses (Crystal R G, et al., *Nat Genet*. 1994; 8(1):42–51). This effect is especially apparent in the vasculature, where a dramatic fall in transduction efficiency and loss of vascular cells is seen over a fairly narrow range of viral concentrations (Schulick A H, et al., *Circ Res*. 1995; 77(3):475–485; Schulick A H, et al., *Circulation*. 1995; 91(9):2407–2414). Thus, the approach described in the present example holds promise as a means to achieve high transfection efficiencies in vivo while avoiding the high doses of virus associated with cytotoxic effects.

In addition to showing enhancement of gene expression, we have investigated the mechanism by which this occurred. Enhancement of gene delivery is blocked by an anti-FGF antibody, excess FGF2, soluble FGF receptor and by heparin. These findings clearly indicate that the response is mediated by FGF2. In addition, our results show that the effect on gene expression is due to an enhancement of binding of virus to cells in the context of FGF2 retargeting, as opposed to any potential stimulatory effect of FGF2 per se. The results are thus in keeping with our goal of retargeting infection through an alternate receptor. This finding has important practical implications for the potential in vivo utility of this approach. A true retargeting mechanism is much more likely to be effective in vivo than a mechanism based on FGF2 stimulation because FGF2 has an extremely short half life in vivo and generally must be given by infusion or in a sustained release formulation for stimulatory effects to be seen (Edelman ER, et al., *J Clin Invest*. 1992; 89(2):465–473).

The binding of FGF2 to cellular receptors is a complex process involving high affinity tyrosine kinase receptors (of which four have been described) as well as binding to low affinity binding sites (heparan sulfates) on the cell surface (Yayon A, et al., *Cell*. 1991; 64(4):841–848). There is evidence that the biological responses of FGF2 are mediated by binding to heparan sulfates initially, then also to the high affinity receptor, thus forming a trimeric complex (Roghani M, et al., *J Biol Chem*. 1992; 267(31):22156–22162). The exact mechanism of increased binding of virus to cells with FGF2 retargeting is not immediately apparent. While a degree of blocking of transduction is seen with excess free FGF competition, which implies high affinity binding (Roghani M, et al., *J Biol Chem*. 1992; 267(31):22156–22162), we observed the most dramatic blocking effect with heparin, which impacts on the interaction of FGF2 with both high and low affinity binding sites (Guimond S, et al., *J Biol Chem*. 1993; 268(32):23906–23914). Thus, although the enhanced viral binding is due to FGF2, the relative contribution of high and low affinity binding sites to this effect is unresolved.

As with many growth factor receptors, FGF receptors are differentially expressed in quiescent versus proliferating or injured cells, with upregulation in the latter group (Casscells W, et al., *Proc Natl Acad Sci USA*. 1992; 89(15):7159–7163; Brothers T E, et al., *J Surg Res*. 1995; 58(1):28–32; Speir E, et al., *J Cell Physiol*. 1991; 147(2):362–373). Thus, we examined the effect of FGF2 retargeting on cells maintained at confluence for a prolonged period, as well as rapidly proliferating cells. Interestingly, we found that the relative enhancement seen with FGF2 retargeting decreased with prolonged time in culture, as did the expression of FGF receptors as measured by FACS analysis. These findings raise the prospect that FGF2 retargeting may permit a degree of adenoviral vector selectivity for proliferating or injured cells in vivo. This would be advantageous in a number of therapeutic situations relevant to cardiovascular medicine as well as the angiogenesis associated with neoplasia. There is in fact some precedent for suggesting FGF2 as a selective targeting ligand for sites of vascular pathology in a study by Casscells et al, where a conjugate between FGF and the toxin saporin is used to selectively eliminate proliferating smooth muscle cells in a model of angioplasty restenosis (Casscells W, et al., *Proc Natl Acad Sci USA*. 1992; 89(15):7159–7163). In this setting, the surrounding quiescent cells are unaffected and the effects seen correlated with the distribution of FGF receptors as demonstrated by radioligand binding. FGF2-saporin is subsequently shown to inhibit neointimal formation in an angioplasty model (Farb A, et al., *Circ Res*. 1997; 80(4):542–550), and selective targeting has also been demonstrated in a model of arteriovenous grafts (Chen C, et al., *Circulation*. 1996; 94(8):1989–1995). Whether such selectivity will be seen in the context of adenoviral targeting however, awaits in vivo investigation.

The many advantages of the adenovirus vector for in vivo use which make it attractive for retargeting strategies have also been recognized by other investigators. Wickham et al recently demonstrated enhanced (7–9 fold) luciferase gene delivery to endothelial and smooth muscle cells in culture using a bispecific anti-FLAG/anti-integrin antibody conjugate and an adenoviral vector with a short fiber and a FLAG epitope engineered into the penton base (Wickham T J, et al., *J Virol*. 1996; 70(10):6831–6838). Another strategy developed by this group targeted infection to cell surface heparan sulfates using a genetically modified virus with polylysine residues at the C-terminal of the knob (Wickham T J, et al., *Nat Biotech*. 1996; 14(11):1570–1573). These strategies also hold promise for vascular gene delivery, but in vivo studies are awaited. We have previously co-developed a strategy using polylysine in the context of targeted adenovirus-polylysine-DNA complexes which achieved efficient targeted gene delivery in vitro (Curiel D T, et al., *Hum Gene Ther*. 1992; 3(2):147–154). However, the in vivo application is limited by complement mediated inactivation of the polylysine component (Gao L, et al., *Hum Gene Ther*. 1993; 4(1):17–24).

The strategy we present herein offers the flexibility to be applied to any adenoviral serotype 5 vector. In addition, our findings indicate the possibility of selectivity for proliferating cells based on the level of FGF receptor expression. In regard to potential in vivo application, we have evidence that the binding of adenoviral knob to Fab is stable in the bloodstream (unpublished observations, 1997) and that Fab-FGF2 retargeting can enhance adenovirally mediated gene delivery to peritoneal tumors in a murine model of ovarian carcinoma, which results in an enhanced therapeutic effect of a herpes simplex thymidine kinase transgene (unpublished observations, 1997). Thus, FGF retargeting of adenoviral vectors holds significant promise for in vivo application.

Over the last several years, strategies have been described for gene delivery to the vasculature that include the use of specialized catheters and chemical enhancers (Feldman L J, et al., *Gene Ther*. 1997; 4(3):189–198). The strategy we describe here complements these approaches and suggests the possibility of eliciting high levels of gene expression and transduction efficiency while avoiding direct adenoviral cytotoxicity. This finding has significant implications for cardiovascular disease. In particular, high transduction efficiencies will be especially useful for the cytostatic strategies currently being proposed for angioplasty restenosis and other proliferative vascular disorders. Our approach may also facilitate targeted angiogenic therapy for myocardial ischemia and peripheral vascular disease, particularly as there is evidence for upregulation of FGF receptors in the context of ischemia (Yamada K, et al., *Acta Neurochirurgica*—Supplementum. 1994; 60:261–264). Thus, this strategy may have a major impact on common clinical problems.

Example 8

Gene Expression is Enhanced in Ad-Infection-Sensitive and Ad-infection-Resistant Cell Lines When Retarfeted Ad are Used to Deliver Therapeutic Nucleotide Sequences As demonstrated in the foregoing Examples and in those to follow, gene expression is enhanced in cell lines to which the retargeted adenoviral vectors of the present invention are administered. Surprisingly, enhanced gene expression was observed not only in those cell lines understood to be sensitive to adenoviral infection; enhanced expression was also observed in cell lines that are normally resistant to Ad infection.

For example, enhanced gene expression is observed when retargeted Ad vectors are used in the following cell lines. In each instance, the abbreviation and cell type of each cell line is indicated.

| Ad-Sensitive Cell Lines | |
|---|---|
| Panc-1 | Pancreatic carcinoma |
| PaCa-2 | Pancreatic carcinoma |
| ASPC-1 | Pancreatic carcinoma |
| BxPC-3 | Pancreatic carcinoma |

| -continued | |
|---|---|
| Sk-Cha-1 | Cholangiocarcinoma |
| SKOV3* | Ovarian Carcinoma |
| D54MG | Glioma |
| ZR-75-1 | Breast Carcinoma |
| RW376 | Kaposi's Sarcoma |
| CVU-1 | Kaposi's Sarcoma |
| Ad-Resistant Cell Lines | |
| Swiss 3T3 | Fibroblast |
| HASMC | Smooth Muscle Cells |
| HUVEC | Endothelial |
| KSY-1 | Kaposi's Sarcoma |
| KS-SLK | Kaposi's Sarcoma |
| KS-1085-1 | Kaposi's Sarcoma |
| KS-1085-B | Kaposi's Sarcoma |
| B16FO* | Melanoma |
| KM12 | Colon Carcinoma |
| CT26 | Colon Carcinoma |
| OVCAR5 | Ovarian Carcinoma |
| K562 | Myeloid Leukemia |

*In vitro and in vivo

Example 9

Retargeted Ad Has Diminished Toxicity and Immunogenicity, and Confers Enhanced Servival in Mice Challenged With Ad-Resistant Tumors Adenoviruses (Ad) have been used as vectors to deliver genes to a wide variety of tissues. Despite achieving high expression levels in vivo, Ad vectors display limitations such as anti-vector immune responses, transient expression, and normal tissue toxicity, which limit therapeutic potential. Targeting strategies to abrogate native tropism and redirect Ad uptake through defined receptors should decrease vector-related toxicities, increase transduction efficiency, and thus allow for systemic administration.

By retargeting Ad using basic fibroblast growth factor (FGF-2) as a targeting ligand, Ad cellular uptake is redirected through FGF receptors, which are upregulated on diseased or injured cells. FGF-retargeted Ad demonstrates markedly decreased hepatic toxicity, liver transgene expression, and immunogenicity. FGF-retargeting is established by conferring sensitivity to tumors that are highly resistant to Ad infection, resulting in enhanced survival of Ad-resistant tumor-bearing mice. This broadly useful method to redirect native Ad tropism may offer significant therapeutic advantages.

Replication-deficient human adenoviruses, mainly serotypes 2 and 5, have been used as vectors for gene delivery in a wide variety of cell types. Despite achieving high expression levels using adenoviral vectors, the toxicity, short-term transgene expression, and immunogenicity limit the usefulness of adenoviral vectors and have prevented demonstration of clinical efficacy (Goldman, et al., *Cancer Res* 57, 1447–1451 (1997); Wagner, et al., *Annu Rev Med* 48, 203–216 (1997)). Several approaches are under investigation to either block the native tropism of adenovirus, decrease its immunogenicity via deletion of parts of its genome, or target the virus to cell types of interest, with mixed success. (See, e.g., Wickham, et al., *J Virol* 71, 8221–8229 (1997); Yang, et al., *Proc Natl Acad Sci USA* 91, 4407–4411 (1994); Morral, et al., *Human Gene Therapy* 8, 1275–1286 (1997); Graham and Prevec, *Methods in Molecular Biology* 109–128 Humana Press, Clifton, N.J., (1991); and Rosenfeld, et al., 1571–1580 (1995).)

A. Materials and Methods

1. Materials

The FGF2-anti-knob fiber Fab conjugate is made as described herein (see also Goldman, et al., Cancer Res 57, 1447–1451 (1997)). FGF2-Fab (0.34 mg/mL) is stored at −80° C. in Dulbecco's phosphate-buffered saline (Gibco BRL, Grand Island, N.Y.). AdCMVHSV-TK has been previously described and is an E1-deleted Ad5 vector which expresses HSV-TK from the CMV promoter. Ad5β-gal is obtained from Molecular Medicine LLC (La Jolla, Calif.). Ad5β-gal is an E1-deleted, E3-mutated vector which expresses β-gal from the CMV promoter. AC2 cells are derived from a clone of 293 cells that had been selected for higher virus production levels (Molecular Medicine, LLC).

Viruses are plaque purified and individual isolates used to infect AC2 cultures. Virus is purified using chromatographic methods to generate infectious virus equivalent to CsCl preparation. Particle number and plaque titering assays are performed using standard methods[2]. Plaque forming units (pfu) for Ad5HSV-TK and Adβ-gal are determined to be $4 \times 10^{10}$ per mL and $9 \times 10^{10}$ per mL, respectively. Particle to pfu ratios for Ad5HSVtk and Ad5β-gal are determined to be 22.5 and 18.9, respectively.

2. Assessment of Hepatic Tropism

Targeting FGF2-Adβ-gal and Adβ-gal is assessed in female C57Bl/6 mice. For preparation of FGF2-Adβ-gal or Adβ-gal, 77 µg of FGF2-Fab, or an equivalent volume of 0.9% NaCl, is incubated for 30 minutes at room temperature with $2 \times 10^{10}$ pfu of Adβ-gal. On day 0, $2 \times 10^{10}$ pfu of either Adβ-gal or FGF2-Adβ-gal are injected intravenously per mouse (over a 30 second period) in a final volume of 0.32 mL. This amounts to a 50:1 molar ratio of FGF2-Fab to fiber molecules. Control mice received 0.32 mL of excipient (25 mM Tris pH 7.5, 100 mM NaCl, 10 mg/mL lactose). On days 2, 4, 7 and 12 post injection, 3 to 6 mice per group are sacrificed. Serum is collected for analysis of transaminases and alkaline phosphatase. The liver is removed, weighed, and immediately snap frozen in liquid nitrogen, stored at −80° C. and then processed for quantitative analysis of β-galactosidase activity. A portion of liver is either fixed for 4 hours at 4° C. in 10% neutral buffered formalin and then embedded in paraffin, or snap frozen in OCT using isopentane precooled with dry ice and stored at −80° C.

3. Histological Determination of β-Galactosidase Activity

Eight micron cryostat sections are fixed in 2% paraformaldehyde, 0.5% glutaraldehyde in PBS pH 7.4 for 30 min. at room temperature. Tissue sections are then rinsed in PBS containing 0.03% NP-40 and 2 mM $MgCl_2$ and incubated for 16 hours at 37° C. in 1 mg/mL 5-bromo-4-chloro-3-indolylb-D-galactopyranoside (X-Gal) (Fischer), 5 mM $K_3Fe(CN)_6$, and 5 mM $K_4Fe(CN)_6$ in PBS pH 7.4 containing 2 mM $MgCl_2$ and 0.03% NP-40. Slides are rinsed in PBS, postfixed in 10% buffered formalin, counterstained for 15 seconds with Nuclear Fast Red, dehydrated and mounted. For morphological studies, routine hematoxylin and eosin staining is performed on paraffin-embedded tissues.

4. Quantitation of β-Galactosidase Activity

β-gal activity is quantitated in mouse liver homogenates according to standard techniques. Briefly, frozen tissues are minced and homogenized on ice in cold lysis buffer by hand using a glass tissue grinder. 100 mg of liver weight is added per mL of 0.2% Triton-X, 100 mM potassium phosphate lysis buffer, pH 7.8. Homogenates are clarified by two centrifugation steps of 20 minutes each at 4° C. in a microfuge at 12,000 g. Supernatants are treated with Chelex-100 resin (BioRad catalog #142–2842) by adding 0.25× volume chelator to each sample. Homogenates are then vortexed briefly, incubated at room temperature for 2 to 5 minutes, and centrifuged for 30 seconds in a microfuge at 12,000 g. A two-fold dilution series of each supernatant is assayed using the Clontech Luminescent β-gal Detection Kit II (catalog #K2048-1). 10 µl of each sample dilution is incubated with 75 µl Clontech β-gal Reagent in 96-well plates at room temperature for 1 hour and read in a Dynatech Laboratories ML3000 Microtiter plate luminometer. The activity of each sample is determined by extrapolation from a standard curve of β-gal enzyme supplied with the Clontech kit, and is expressed in mU/g organ weight. Statistical analysis of the data is performed using an unpaired t-test.

5. Immunogenicity Study

Female BDF1 mice (n=5/group) are treated intraperitoneally on day 0 with $1 \times 10^9$ pfu of Adβ-gal or FGF2 Adβ-gal (at a 2000:1 ratio of FGF2-Fab to knob monomer). Control mice received 200 µL of PBS. On day 21, blood samples are collected and assayed for antibodies by ELISA.

6. ELISA Procedures

Ninety-six well cluster plates (Costar catalog #3590) are coated overnight with 100 µl per well of either Ad5 ($3 \times 10^8$ PFU/well) or purified fiber protein (0.1 µg/well) diluted in PBS. Plates are then rinsed three times with PBS and blocked for 2 hours with PBS containing 10% goat serum (GIBCO, Grand Island N.Y.). Following three additional rinses, sera diluted 1:50 in PBS are added as 100 µl volumes and incubated for 30 min. Wells are again rinsed three times with PBS, and 100 µl of an optimal dilution of F(ab')2 fragments of alkaline phosphatase-labeled goat anti-mouse Ig are added per well. Following three rinses in Tris buffered saline (TBS), bound antibody is detected by the addition of 100 µl of p-nitrophenyl phosphate (Sigma Chemicals, St. Louis Mo.).

Following a 60 min incubation, substrate reactions are determined using a microplate reader set at a wavelength of 490 nm for reference and 405 nm for detection. All wells are blanked against six wells that had not received primary antibody, and the mean of three triplicate wells determined for each serum sample. Data are expressed as $OD405 \times 10^3$.

B. B 16 Melanoma Tumor Model

FGF2-AdHSVTK is prepared by mixing 0.3 or 0.03 µg of FGF2-Fab with $1 \times 10^8$ pfu of FGF2-AdHSVTK (molar ratio of 3:1 or 30:1 FGF2-Fab to knob) and incubating for 30 minutes at room temperature. Either FGF2-AdHSVTK, AdHSVTK, or 20 mM HEPES buffer are then mixed with B16 melanoma cells in suspension at a multiplicity of infection of 50:1. This mixture is incubated at room temperature for one hour.

Female BDF1 mice (n=8/group) received $2 \times 10^6$ B16F0 cells (Lou Weiner, Fox Chase Cancer Center), treated with either FGF2-AdHSVTK, AdHSVTK, or 20 mM HEPES buffer, implanted intraperitoneally on day 0. Mice are then administered ganciclovir (Cytovene, Roche) (or $H_2O$) intraperitoneally beginning on day 1, qd×14, at a dose of 100 mg/kg. Mice are then followed for survival. Statistical analysis is performed using Kaplan-Meier and a Logrank (Mantel-Cox) post-hoc analysis.

C. Results and Discussion

In rodent models, the majority of Ad vector delivered extravenously is cleared rapidly, within the first 24 hours, in the liver. Concomitantly, there is considerable transduction of liver hepatocytes and associated transgene expression. This is in part due to a high concentration of the Ad cellular receptor, Coxsackie-adenovirus receptor (CAR), in the rodent liver. Ad transgene expression rapidly declines over the first 7 days after Ad vector administration but is associated with significant liver toxicity as manifest by increased serum transaminases, necrosis, and inflammation (Yang, et al., Id. (1994); Gao, et al., *J Virol* 12, 8934–8943 (1996); Hwang, et al., *Am J Respir Cell Mol Biol* 13, 7–16 (1995)). Retargeting of Ad away from its native tropism for CAR may abrogate this liver toxicity.

We have developed a broadly useful method which retargets Ad by using a neutralizing Fab to the knob region of the Ad fiber protein. The fiber protein is used by adenovirus for binding to CAR. By attaching FGF2 (basic fibroblast growth factor) as a targeting ligand to this Fab, this bifunctional molecule targets and redirects adenovirus cellular entry via high affinity FGF receptors. FGF2 binds FGF receptors with unusually high affinity ($Kd \approx 10^{-12}$ M) compared to other ligand-receptor interactions. FGF receptors are upregulated in a number of diseases characterized by unwanted cellular proliferation, and many human malignancies contain elevated levels of one or more of the four recognized FGF receptors.

We have previously demonstrated that FGF2 targets DNA both in vitro and in vivo. Recently, we have demonstrated up to a 12-fold increase in gene expression using FGF2-retargeted Ad compared to Ad in delivering reporter genes or the HSV thymidine kinase (TK) gene to human Kaposi's sarcoma cell lines in vitro and human ovarian carcinoma cells both in vitro and in vivo (Sosnowski, et al., *J Biol Chem* 271: 33647–33653 (1996)). We reasoned that the enhanced in vivo potency implied greater specificity, thus it is appropriate to assess whether FGF2-Ad shows diminished toxicity and immunogenicity by altering its native tropism. Redirected tropism may be further evaluated in mice challenged with tumor cells resistant to native Ad infection.

1. Redirection of Hepatic Tropism

To accomplish retargeting of Ad, a bifunctional molecule is made by conjugating FGF2 to a blocking anti-fiber Fab. This molecule is then incubated with Ad prior to transduction of cultured cells or use in vivo. The high-affinity interaction of this Fab with the knob domain of the Ad fiber protein has been measured at $2.1 \times 10^{-9}$ M using Biacore analysis. This value is comparable or greater than commercially available therapeutic antibodies.

To determine if FGF2 retargeted Ad blocks the native tropism of Ad for the liver, FGF2-Adβ-galactosidase (β-gal) and Adβ-gal are injected intravenously into mice and expression of β-gal in the liver is assessed. Mice are sacrificed on days 2, 4, and 7 post injection of either excipient, Adβ-gal ($2 \times 10^{10}$ pfu, i.v.) or FGF2-Adβ-gal ($2 \times 10^{10}$ pfu, i.v.). Liver tissue is processed and stained with Xgal as described above.

On days 1, 2, 4, 7, and 12 post administration, markedly greater numbers of Xgal-stained hepatocytes are present in the livers of mice treated with Adβ-gal compared to the livers of mice treated with FGF2-Adβ-gal, which had a profound decrease in X-gal-stained hepatocytes (not shown). No X-gal⁺ hepatocytes are observed in control mice (data not shown).

Quantitation of β-galactosidase activity in the liver (Table 3) parallels the histochemical results and demonstrated 12- to 20-fold less β-gal in the livers of FGF2-Adβ-gal-treated mice than in the livers of Adβ-gal-treated mice. By day 12, a modest level of β-galactosidase is still present in the liver of Adβ-gal-treated mice (259 mU/gram) but is undetectable in the liver of FGF2-Adβ-gal-treated mice.

TABLE 3

Quantitation of β-galactosidase in the Liver
of Mice Treated with Adβ-gal or FGF-Adβ-gal

| Treatment | Mean β-galactosidase Activity (mU/gram) | | |
|---|---|---|---|
| | Day 2* | Day 4 | Day 7 |
| Adβ-gal | 5151* | 2668** | 804*** |
| FGF2-Adβ-gal | 365 | 217 | 41 |

*p = 0.003 compared to FGF2-Adβ-gal
**p = 0.005 compared to FGF2-Adβ-gal
***p = 0.02 compared to FGF2-Adβ-gal FIG. 9 shows the serum transaminase and alkaline phosphatase levels in mice treated with Adβ-gal or FGF2-Adβ-gal. On day 7 post injection of either excipient, Adβ-gal ($2 \times 10^{10}$ pfu, i.v.) or FGF2-Adβ-gal ($2 \times 10^{10}$ pfu, i.v.) serum is prepared and transaminases (ALT, AST) and alkaline phosphatase (Alk Phos) are measured. The data are presented as mean+/–S.E.

On day 7 post administration, serum transaminase levels are elevated 8- to 16-fold in the Adβ-gal treated group but only 3- to 5-fold in the FGF2-Adβ-gal-treated group (see FIG. 9). Serum alkaline phosphatase is also elevated in the serum of Adβ-gal-treated mice but is within normal limits in FGF2-Adβ-gal-treated mice.

Histopathology on day 7 revealed evidence of severe hepatocellular necrosis and a marked inflammatory infiltrate in the liver of mice treated with Adβ-gal (Adβ-gal, $2 \times 10^{10}$ pfu, i.v.), but analysis of livers from the FGF2-Adβ-gal-treated group (FGF2-Adβ-gal, $2 \times 10^{10}$ pfu, i.v.) revealed that the hepatocellular necrosis is almost completely abrogated and only a minimal inflammatory infiltrate is observed (data not shown).

2. Immunogenicity

We hypothesized that blocking a potential immunodominant epitope, the fiber protein knob domain, would diminish the antibody response to Ad. Accordingly, the humoral response to either FGF2-Ad or Ad following a single intraperitoneal injection is evaluated. Serum antibodies directed against total adenovirus or purified fiber protein are measured by ELISA on day 21.

FIG. 14 illustrates serum antibody levels of antiadenovirus and anti-knob protein antibodies in mice treated with either excipient, Adβ-gal, or FGF2-Adβ-gal. On day 21 post injection of either excipient, Adβ-gal ($1 \times 10^9$ PFU, i.p.), or FGF2-Adβ-gal, sera are prepared and assayed by ELISA for specific antibody levels directed against either total adenovirus or purified knob protein. Data are presented as the mean $OD_{405} \times 10^3$ value of three triplicate wells as determined for each serum sample. In addition, the arithmetic mean (dashed line) are compared using one-way analysis of variance and Fisher's procedure for least significant differences for a posteriori contrasts. For antiadenovirus responses, the adenovirus group differs from both the excipient and FGF2-Ad groups by p<0.0001. For anti-knob protein responses, the adenovirus group differs from the excipient group by p<0.0001 and from FGF2-Ad group by p=0.0003.

Compared to Ad alone, FGF2-Ad induces a lower mean anti-Ad antibody response and 2/5 mice had no anti-Ad antibody in the FGF2-Ad treated group. Similarly, mean titers are less, and 3/5 mice generated no antibody response to the knob domain of fiber protein in the FGF2-Ad-treated group compared to the Ad-treated group. The data, which demonstrate that the mean anti-knob antibody response is >50% of the anti-Ad response, supports the hypothesis that knob is an immunodominant epitope (see FIG. 14).

3. Ex Vivo Transduction of B16 Melanoma

To determine whether FGF2-Ad can transduce cells which are insensitive to native Ad infection, the B16 murine melanoma cell line is chosen as the target. B16 tumor cells express FGFR1 and FGFR3 mRNA and are sensitive to FGF2-targeted DNA and protein toxins. B16 cells are incubated for 1 hour ex vivo with either Ad containing the herpes simplex virus thymidine kinase gene (AdHSVTK) or FGF2-AdHSVTK prior to implantation intraperitoneally in BDF1 mice. Ganciclovir prodrug therapy is initiated in vivo, one day post tumor cell inoculation.

FIG. 11 shows survival analysis of mice treated with either B16F0 tumor cells incubated ex vivo with AdHSVTK or FGF2-AdHSVTK. B16 melanoma cells are treated ex vivo for one hour with either AdHSVTK or FGF2-AdHSVTK and then implanted intraperitoneally into BDF1 mice at $2 \times 10^6$ cells per mouse. Mice are then treated with either Ganciclovir or H20 (as a control) for 14 days, i.p. Survival of tumor bearing mice treated with FGF2-AdHSVTK and then administered ganciclovir have a statistically prolonged survival compared to all other groups ($p=0.001$).

The survival of mice bearing B16 melanoma treated with AdHSVTK plus ganciclovir is indistinguishable from the control mice which received untreated B16 tumor cells plus the ganciclovir regimen (median survival 18–19 days; see FIG. 11). In striking contrast, mice which received B16 melanoma treated with FGF2-AdTK, at two different FGF2-Fab to knob molar ratios, demonstrated a2.6-fold increase in median survival compared with the control groups (FIG. 11).

There are several significant obstacles to the use of adenoviral vectors for cytotoxic gene therapy of cancer. First, the transduction of normal, non-tumor cells by adenovirus can lead to toxicity which has limited preclinical studies and initial clinical trials to direct injection into tumors or locoregional delivery to a compartment containing tumor cells (Goldman, et al., Id. (1997); Mazue, et al., *Toxicol Lett* 64–65, 329–338 (1992); Ying, et al., *Cancer* 74, 848–853 (1994)).

Additionally, the immunogenicity of adenoviruses is a potential hurdle to repeat dosing. We have developed a method to abrogate the native tropism of adenovirus and redirect its cellular uptake through FGF receptors. Because there are few normal tissues responsive to administration of exogenous FGF2 (Wagner, et al., *Proc Natl Acad Sci USA* 89, 6099–6103 (1992); Tomko, et al., *Proc Natl Acad Sci USA* 94, 3352–3356 (1997); Worgall, et al., *Human Gene Therapy* 8, 37–44 (1997)), transduction of normal tissues with FGF2-Ad should be limited (data not shown).

Further, redirecting Ad with FGF2 should abrogate the liver tropism of adenovirus and decrease its toxicity. Indeed, FGF2-Ad induced 12- to 20-fold less transgene expression (β-gal) in the liver than non-retargeted Ad and had only a modest effect on serum transaminase levels compared to the robust increase of serum transaminases in the mice receiving Ad. When the humoral responses to Ad and FGF2-Ad are compared, FGF2-Ad displayed reduced immunogenicity, as anti-Ad and anti-fiber protein antibodies are not found in all treated mice, unlike the Ad-treated group. Although it might be expected that FGF2-anti-fiber Fab could block the antibody response to the fiber protein, the blunting of the response to other epitopes on the virion surface is unexpected. Whether FGF2-Fab is masking these other epitopes through steric hindrance, or whether it directs the clearance of virus through less immunogenic pathways, is unknown.

Multiple doses of the re-engineered vectors of the present invention may be administered in vivo without an appreciable level of humoral response resulting therefrom. Thus, the modified vectors of the present invention are significantly less immunogenic than other vectors described in the art.

Furthermore, to demonstrate that native Ad tropism can be fully redirected to cells bearing FGF receptors, we have shown that an Ad-resistant tumor line (B16 murine melanoma) can be made sensitive to FGF2-AdHSVTK transduction. Mice challenged with FGF2-AdHSVTK-treated B16 melanoma cells have greatly prolonged survival when compared to mice bearing control or AdHSVTK-treated B16 melanoma cells.

We have also demonstrated FGF2-AdHSVTK to be at least 10-fold more potent than AdHSVTK in vivo in a human ovarian cancer model which is sensitive to Ad (Rancourt, et al., *Nat Med* (1997)). Because of the enhanced efficacy and decreased toxicity of FGF2-retargeted Ad in comparison to Ad, the therapeutic index in vivo is greatly enhanced. FGF2 retargeting of viral vectors thus provides a useful approach to targeted gene delivery, which will be required for successful clinical oncology applications.

Example 10

Efficacy of Intraperitoneal Delivery of FGF2FabAd21 in a Her-2/neu Overexpressing Human Ovarian Carcinoma Model (SKOV3IP1)

An Ad vector that produces an intracellular single-chain antibody to the Her-2/neu receptor (i.e., an "intrabody") is evaluated for activity in vivo. In various cell culture experiments, this Ad (Ad21) has been shown to induce apoptosis in cell lines overexpressing the Her-2/neu receptor. The efficacy of Ad21 and FGF2FabAd21 is tested in the SKOV3ip1 model.

Methods for the construction of antibodies, including single-chain antibodies, which may be useful as "payloads," as well as suitable antibodies and fragments thereof that may be used in such a therapeutic context, are available in the art. For example, see U.S. Pat. No. 5,587,458, which describes single-chain antibodies to the Her-2/neu (also known as erbB-2) receptor. The generation and use of intrabodies is also disclosed in published International App. No. WO 96/07321. The disclosures of those documents are incorporated by reference as though fully set forth herein.

SKOV3ip1 cells are implanted ip on day 0. On day 5, mice receive a single ip dose of either Ad21 or FGF2FabAd21 at either of two dose levels and then they are followed for survival. For example, dosages of Ad21 and FGF2FabAd21 administered are $1 \times 10^9$ pfu and $5 \times 10^9$ pfu.

Figure 21:
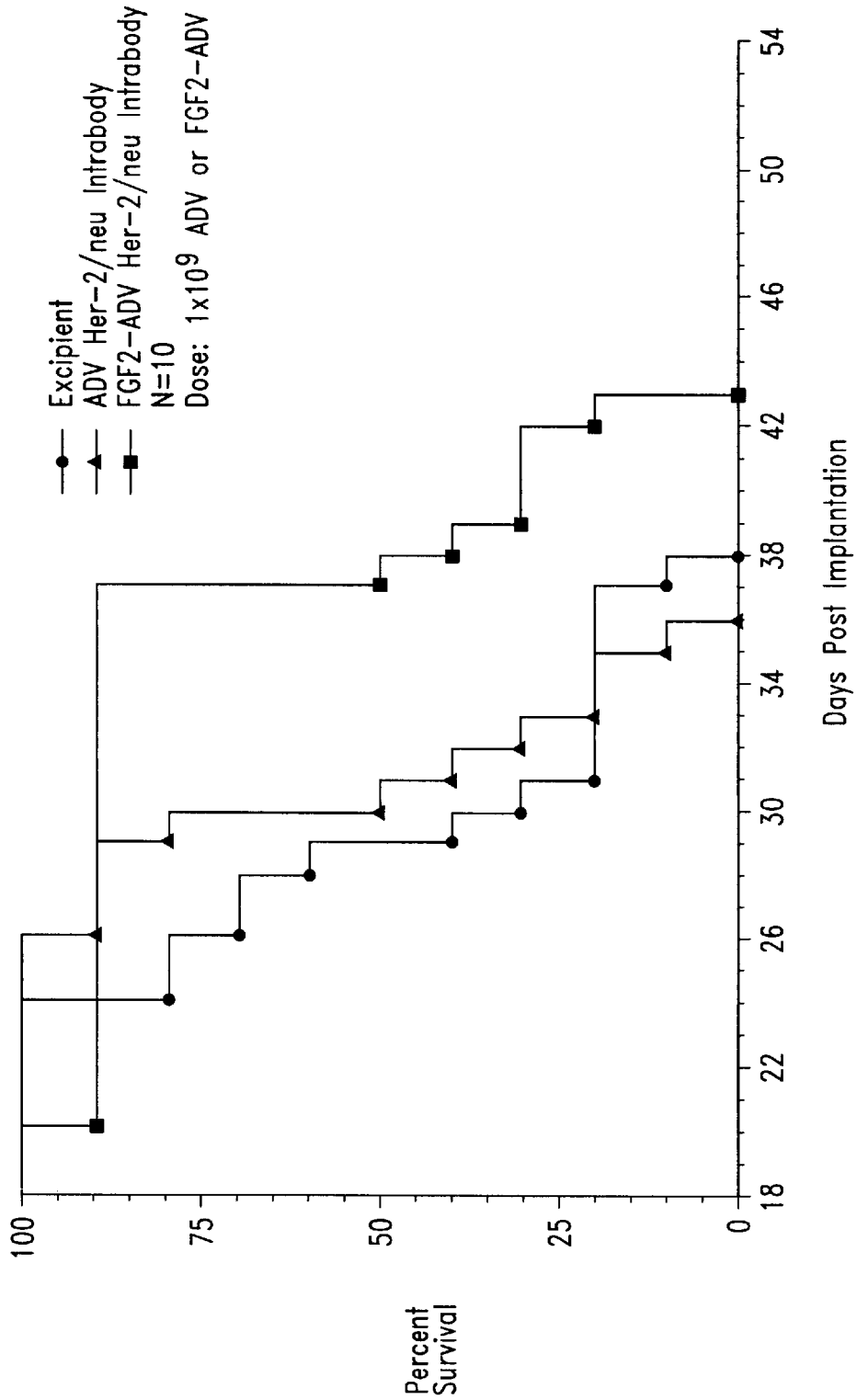
FIG. 21 illustrates the increased survival time seen in an in vivo murine tumor model when an Ad vector re-targeted with FGF2 and delivering an intrabody payload is administered to SKOV3 tumor-bearing mice. Percent survival is plotted on the vertical axis; post-implantation survival (in days) is plotted on the horizontal axis. Closed circles represent mice receiving excipient alone (control); closed triangles represent mice receiving non-retargeted Ad delivering Her-2/neu intrabody; and closed squares represent mice receiving FGF2-retargeted Ad delivering Her-2/neu intrabody. As indicated, N=10; the dose administered was 1×$10^9$ ADV or FGF-2 ADV.

FIG. 21 illustrates the increased survival time seen in an in vivo murine tumor model when an Ad vector re-targeted with FGF2 and delivering an intrabody payload is administered to SKOV3 tumor-bearing mice. Percent survival is plotted on the vertical axis; post-implantation survival (in days) is plotted on the horizontal axis. Closed circles represent mice receiving Excipient alone (control); closed triangles represent mice receiving non-retargeted Ad delivering Her-2/neu intrabody; and closed squares represent mice receiving FGF2-retargeted Ad delivering Her-2/neu intrabody. As indicated, N=10; the dose administered was $1 \times 10^9$ ADV or FGF-2 ADV.

While non-retargeted Ad2l has a minimal effect on survival, in the high dose FGF2FabAd21 treated group, median survival is significantly increased (%ILS=128; data not shown). Again, FGF2 retargeting of viral vectors shows itself to be useful in both positive and negative gene therapy contexts and underscores the likelihood that viral retargeting using polypeptides reactive with pre-selected receptors not normally targeted by viral vectors retaining their native tropism enhances the likelihood of success in a variety of therapeutic contexts, including clinical oncology applications.

Example 11

Successful Retargeting of Adenoviral Vectors Using KGF and 11A8

In order to demonstrate that a variety of receptor-binding and internalizing ligands are useful in the retargeting of adenoviral vectors, conjugates of anti-knob Fab and KGF, as well as conjugates of anti-knob Fab and 11A8 antibody, are constructed as described below. Administration of conjugates retargeted using the aforementioned polypeptides reactive with FGF receptor demonstrate successful modification of Ad tropism as well as a concomitant increase in gene expression, as described.

KGF is particularly useful in targeting epithelial cells, hepatocytes, and type II pneumocytes of the lung, which makes it ideal for a variety of gene targeting and delivery applications, as discussed previously. Therefore, its incorporation into a ligand-Fab construct and its use as an Ad-retargeting agent provides additional treatment options, particularly when one is addressing disease conditions that involve the cells and receptors specifically targeted by KGF—e.g. hepatocytes and type II pneumocytes.

A method of generating and purifying Ad knob antigen, which is used to generate anti-knob antibody (from which Fab and other fragments are readily prepared) is also described as exemplary.

A. Purification of Knob Antigen

A fed-batch fermentation generated approximately 1.4 kg paste and knob is purified using two sequential chromatography steps: cation-exchange followed by immobilized metal ion affinity chromatography (IMAC). Cation-exchange chromatography (CEC) is used as a capture and primary recovery step following lysis and clarification. The CEC-purified product is then purified by IMAC (charged with nickel) based on the affinity of the poly-histidine n-terminus of knob for nickel. The knob product has been fully characterized (data not shown).

In the native state, the knob antigen has been shown to exist as homotrimer. The theoretical molecular weight based on the cDNA which codes for knob monomer is 22,539 Da. Based on the analyses to date, the purified product appears to exist principally as a trimeric molecule with binding characteristics equivalent to the reference standard. Knob antigen is also useful as an affinity ligand immobilized to a chromatographic resin for in-process testing and use in purifying preparative quantities of FGF-Fab, KGF-Fab, EGF-Fab and 11A8-Fab.

B. Preparation of Hybridoma Secreting 11A8 Antibody

Female Balb/C mice were injected subcutaneously with $10^7$ SK-HEP-1 cells in 0.2 ml Dulbecco's PBS to generate the antibody 11A8. The animals were reimmunized 14 and 28 days later with $10^7$ cells injected intraperitoneally. The fusion was done 4 days after the final immunization.

Spleen cells taken from an immunized mouse were fused with NS-0 cells using PEG-1500. Hybridoma cells were selected in RPMI-1640 containing HAT and 0.005% 2-mercaptoethanol followed by RPMI-1640 containing HT.

An ELISA was used for screening the hybridomas. Briefly, plates were coated with 50 ul of ECDR 1 (100 ng/ml) overnight at 4° C. After washing, conditioned media samples were added. A second antibody conjugated to horseradish peroxidase (Bio-Rad, 1:1000 dilution) was used to detect hybridomas. Cells in positive wells were cloned by limiting dilution.

Antibodies were purified by ammonium sulfate precipitation and Affi-Gel Protein A agarose column (Bio-Rad, Richmond, Calif.) chromatography according to the manufacturer's protocol. The purity of the antibody was checked by a 7.5% PhastGel (Pharmacia, Uppsala, Sweden) under non-reducing conditions with Coomassie blue stain.

C. KGF-Fab and 11A8-Fab

A preliminary small-scale study is performed in which KGF is conjugated to Fab (anti-knob). The conjugate is purified using procedures analogous to those used for the conjugation and purification of FGF-Fab as described hereinabove (i.e., Heparin-Sepharose affinity chromatography followed by size exclusion chromatography), with minor modifications. In particular, KGF and 11A8 are derivatized with SPDP (monoderivatized) according to the manufacturer's instructions (Pharmacia, Piscataway, N.J.); isolated and then conjugated to Fab. The final bulk conjugate is analyzed by SE-HPLC, and the molar ratios of KGF to Fab are determined by SDS-PAGE/Coomassie (results not shown).

SE-HPLC demonstrates that the conjugate is heterogeneous but does not contain detectable levels of free KGF or free Fab. The molar ratios of Fab to KGF are estimated at 1:1, based on scanning densitometry of SDS-PAGE/Coomassie stained gels under reducing conditions (data not shown).

Biological activity of the KGF component of the conjugate is assessed by a proliferation assay performed on Balb/MK cells. The conjugate is equipotent to the derivatized KGF and underivatized KGF standard (not shown). The knob-binding activity and transduction activity are readily evaluated using standard assays and procedures, as those of skill in the relevant art will readily appreciate.

Figure 20:
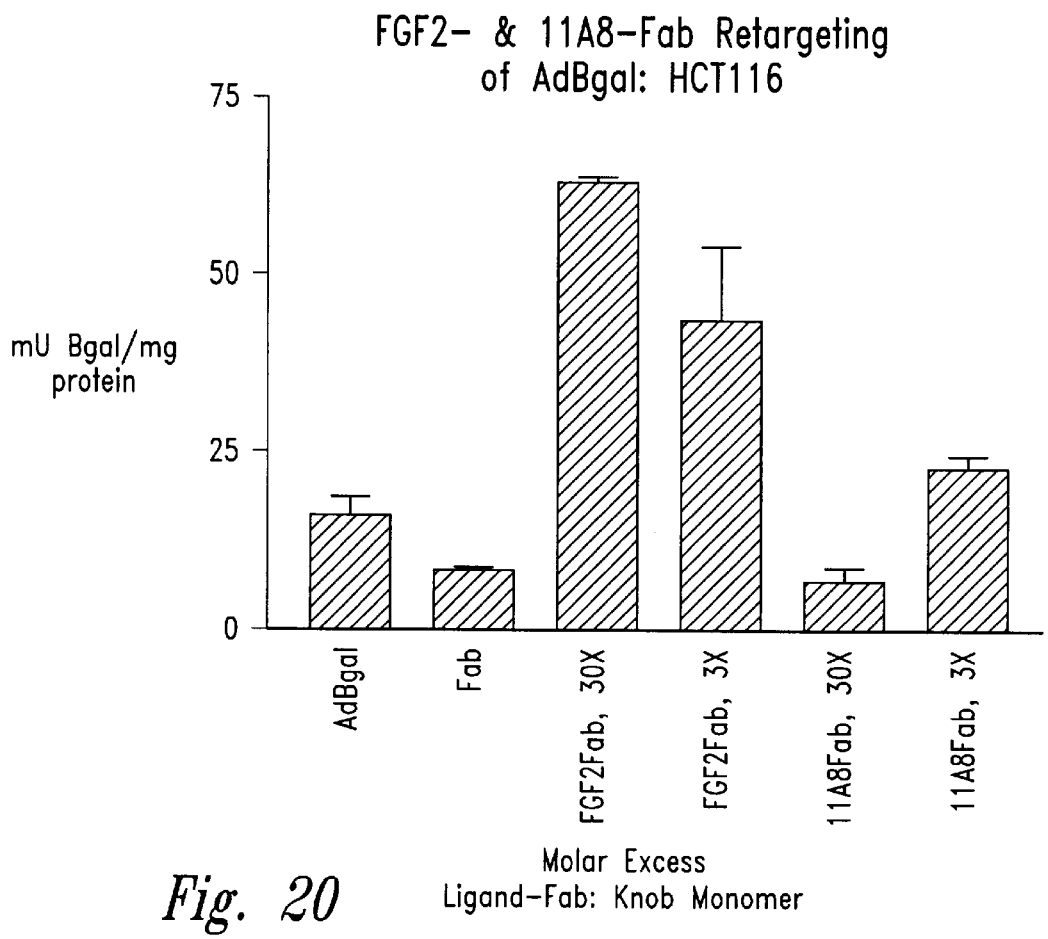
FIG. 20 illustrates the successful retargeting of an Ad vector linked to a marker (Adβgal) using either FGF2 or 11A8-Fab and the successful delivery of the marker sequence in HCT116 cells. From left to right, the shaded bars represent Adβgal; Fab; FGF2Fab, 30×; FGF2Fab, 3×; 11A8Fab, 30×; and 11A8Fab, 3×. Molar excess of Ligand-Fab:Knob Monomer is indicated in the latter four categories. On the vertical axis, mU βgal/mg protein is indicated. (Conditions: 25K; 72 hr; 300 MOI.)

FIG. 20 illustrates the successful retargeting of an Ad vector linked to a marker (Adβgal) using either FGF2 or 11A8-Fab and the successful delivery of the marker sequence in HCT116 cells. From left to right, the shaded bars represent Adβgal; Fab; FGF2Fab, 30×; FGF2Fab, 3×; 11A8Fab, 30×; and 11A8Fab, 3×. Molar excess of Ligand-Fab:Knob Monomer is indicated in the latter four categories. On the vertical axis, mU βgal/mg protein is indicated. (25K, 72 hr; 300 MOI.)

The foregoing specification, including the specific embodiments and examples, is intended to be illustrative of the present invention and is not to be taken as limiting. Numerous other variations and modifications can be effected without departing from the true spirit and scope of the present invention.

We claim:

1. A tropism-modified adenoviral vector system that specifically targets cells expressing a preselected receptor, comprising:
   an antibody or fragment thereof that binds an adenoviral capsid protein;
   a targeting ligand that binds the preselected receptor; and
   an adenovirus containing a nucleic acid molecule that encodes a gene product under the control of a promoter;
   wherein the ligand is a fibroblast growth factor (FGF) polypeptide that is conjugated to the antibody or fragment thereof and is reactive with a fibroblast growth factor (FGF) receptor, and wherein the antibody or fragment thereof is bound to the adenovirus.

2. The vector of claim 1, wherein said promoter is a tissue-specific promoter.

3. The vector of claim 1, wherein said polypeptide reactive with a FGF receptor is selected from the group consisting of FGF-1, FGF-2, FGF-3, FGF-4, FGF-5, FGF-6, FGF-7, FGF-8, FGF-9, FGF-11, FGF-13, FGF-14, and FGF-15.

4. The vector of claim 1, wherein said polypeptide reactive with a FGF receptor is FGF-2.

5. The vector of claim 1, wherein the native tropism of said vector is ablated.

6. The vector of claim 1, wherein the gene product enhances cellular proliferation.

7. The vector of claim 1, wherein the gene product enhances cellular differentiation.

\* \* \* \* \*